United States Patent
Van Der Vossen et al.

(10) Patent No.: US 8,399,737 B2
(45) Date of Patent: Mar. 19, 2013

(54) **FUNCTIONAL R-GENE FROM *SOLANUM BULBOCASTANUM***

(75) Inventors: Edwin Andries Gerard Van Der Vossen, Utrecht (NL); Anoma Akuvi Lokossou, Wageningen (NL); Richard Gerardus Franciscus Visser, Bennekom (NL); Evert Jacobsen, Wageningen (NL)

(73) Assignees: Wageningen Universiteit, Wageningen (NL); Kweek—en Researchbedrijf Agrico B.V., Bant (NL)

( * ) Notice: Subject to any disclaimer, the term of this patent is extended or adjusted under 35 U.S.C. 154(b) by 530 days.

(21) Appl. No.: 12/522,704

(22) PCT Filed: Jan. 28, 2008

(86) PCT No.: PCT/NL2008/050050
§ 371 (c)(1),
(2), (4) Date: Feb. 1, 2010

(87) PCT Pub. No.: WO2008/091153
PCT Pub. Date: Jul. 31, 2008

(65) Prior Publication Data
US 2010/0162437 A1    Jun. 24, 2010

(30) Foreign Application Priority Data
Jan. 26, 2007   (EP) .................................. 07101270

(51) Int. Cl.
*A01H 5/00*     (2006.01)
*C12N 15/09*    (2006.01)
*C12N 15/29*    (2006.01)
*C12N 15/82*    (2006.01)

(52) U.S. Cl. ........ 800/279; 800/278; 800/298; 800/317; 536/23.6; 435/320.1; 435/419; 435/252.2; 435/468; 435/417

(58) Field of Classification Search ...................... None
See application file for complete search history.

(56) References Cited

FOREIGN PATENT DOCUMENTS

| WO | WO-03/066675 | 8/2003 |
|---|---|---|
| WO | WO-2004/020594 | 3/2004 |
| WO | WO-2005/014631 | 2/2005 |

OTHER PUBLICATIONS

Bittner-Eddy et al., Plant Journal (2000) 21(2):177-188.
Database CABA, Accession No. 2005:117239.
Database EMBL, Accession No. CC884779, Aug. 1, 2003.
Hein et al., International Journal of Plant Genomics (2007) 2007:51421.
International Search Report for PCT/NL2008/050050, mailed on Jun. 10, 2008, 4 pages.
International Preliminary Report on Patentability for PCT/NL2008/050050, issued on Jul. 28, 2009, 7 pages.
Li et al., Theoretical and Applied Genetics (1998) 96(8):1121-1128.
Park et al., Molecular Breeding (2005) 16:33-43.
Park et al., Molecular Plant-Microbe Interactions (2005) 18(7):722-729.
Park et al., Theoretical and Applied Genetics (2005) 111(3):591-597.
Vossen et al., Plant Journal (2003) 36(6):867-882.

*Primary Examiner* — Medina A Ibrahim
(74) *Attorney, Agent, or Firm* — Morrison & Foerster LLP

(57) ABSTRACT

The invention relates to a resistance gene and functional homologs or fragments thereof isolated from *Solanum bulbocastanum*. Moreover, the invention relates to the use of this resistance gene, for example, in a method to increase or confer at least partial resistance in a plant to an oomycete infection.

17 Claims, 16 Drawing Sheets

| Informative Polymorphic Site Position | (positions 0000000147, 0000000478, ... through 0000000552) |
|---|---|
| R2-likeGH-3 | CT GGAGAC ATTG AC AGAGAAAC AGTGTT CACC TAGAGT CGC CAC CAAG |
| R2-likeGH-5 | CT GGAGAC ATTG AC AGAGAAAC AGTGTT CACC TAGAGT CGC CAC CAAG |
| R2GH-D3 | CT ACGTCT CTGA AG AGAGAAAT CAGT GCC CGG CACCT GCC CAC TGAG |
| R2 | CT ACGTCT CTGA AG AGAGAAAT CAGT GCC CGG CACCT GCC CAC TGAG |
| R2GH-2 | AAG AGTCC GAAGCG TAAGCG CAGA GCCA GTGT CAGCCTGTTG CAAA ACTT GCT |
| Rpi-abpt | AAG AGTCC GAAGCG TAAGCG CAGA GCCA GTGT CAGCCTGTTG CAAA ACTT GCT |
| R2-like | AAG AGTCC GAAGCG TAAGCG CAGA GCCA GTGT CAGCCTGTTG CAAA ACTT GCT |
| Rpi-blb3 | AAG AGTCC GAAGCG TAAGCG CAGA GCCA GTGT CAGCCTGTTG TCC AACT TGCG |

| Domains | Leucine zipper |  |
|---|---|---|
| Informative Polymorphic Region |  | Region A |

```
   1 GATCAAAAAC GGATTCGGGG AGTGAAAAGC TTACCGTTAG CCTCAAGAAC GATGGAAAAC
  61 TATCAAGAGT CGTCTGGGGT TCGTTCCTTA GCTCTAAAAA TCGAAAAGTG CAGAATAAAG
 121 ACGTTTTGAG GCTTATTTAC GCACTACAAA AAAATCATAT ATTGCTGCAA AATTTGTTGT
 181 AGCTAAATAT GAAAATTTCC ATGGCTAAAC TTCAATATTT TCTTCCTTAG CATTCGTAGC
 241 AAGATATAGC ATGGCTAAAA GTTAGCTACA AACTTTACAT GGTTCATGGC TGAGAACTAA
 301 TATCTATTGC TACAAAATTT TTGAGTTGTA GCTGTACTGA TAAAAAGTTT TTGCCACACA
 361 AAATATATAT ATATATATAG CAAATAACTT TATTCTTTTG CCACGTCAAA AATGATTTAT
 421 AGTTGTCTTT TTAGATGCAG CCACAAAGCT ATTACATTGT AGCAACATAT TTAATTTGGT
 481 TTCCATGTAA ACAGAAATTT GTAGCTATTT GTATAGCTTA GTCACGTGGC AATAGTACTC
 541 GTATTTAGTT ATGACTATTA AAATTCATGG CAATAACATG AAGTATTTAC CACAAGCATT
 601 TTCGAATTAT AGCTAAAATT CATATCTTTA GCCATGAATA TATATAATTT TAGCTAAAAA
 661 TCCATTTGCT ACGAAAGTCA AAATTTATAT ACATGTTTTT TTACGTGATA TATATAGAAA
 721 ATTTGTTGCA TTCAATATAT AATTCCATTA TTATTAGAGA TTTTTTCGCA AGCTTTATTA
 781 GTTCCAAGAG CTACATAATG TAGCTATGAA TTAATTTTA AGATTTCAAA ACACTTCCTA
 841 AATTACGTAT AATTACAATT TACAATTTTA AAAATAGTTC TAATTATATA TAACTCATGT
 901 AATACACTAT CTTGTTGAG TACAAAGCAG TATAGTCTTC TCTTATTTCT CCTTCCACAA
 961 CGTTCAATTG AATCTTAGCT TGATTTACAC CGATCTTGTC ATTTAGATGC TTTAACTCCA
1021 TTGATATACC TATCAAATG ATGAAGTATT TCAACACCAA CAATCATTAC CAACTAATTA
1081 TAGATGAGAG TGTGTGTTAT ATAATATTTC AAGAAGACAA CAAATTTATT TATATATATA
1141 TCATTAGCTA AAAAATTTGA AAGATACAAA CAAAAATATG CAAGAAAAAA AAGTAAACAA
1201 ATCTATAAAC TTTTATTTCT TAAAATAATG TTCACCTCAA TTGTGACATT TTTGGCGGTT
1261 TGCGAATTAT GACTCCTCTC AACACTATTT AAATTTTAAA ATCTTCACAA TCTGCTCATA
1321 AATAAGATGT AATATTTTTT AAAAGATCTA AAATAATCTA AACCCAAAAA TCTAAGTCAA
1381 ATAAGTGAAA CATAAATTCG AAAATTGTAA ATAAGAAGAT ATGAACATGC CTTGAATATA
1441 AAAAAACCAC AAAAAGAAAT TAGCAAAACA TTCTACATTT TGAAATGCCA AAGTCTTCTC
1501 TCTCAACATT TATCTCTTGA GCAAGGAGAT TTCCATGTAA ACTTCATGTC CTTTACTTTA
1561 AGCATTACTT CCGATATTGT TCTTACCTTT GTCAAGGAAC CTAGTCCATT GACCTATGGT
1621 GGACACAGAT AAGCTAACAA CATTTAATAC CCTAACTACC ATTACCACAA CAGGTAGAGT
1681 ACGCTGAATT TTTCTAAGTT GTGTCACCAT TTAAAGGACA AAAATGACTC AAGAGTAAAA
1741 TCAATGAAGC ATTTGCTGCA GGCCTCCAAA AGTTTTATCG ATATATTTTT TTTTAATAAT
1801 TTGCTCGTTC TTCCAAATCA GTTGAAACTT GAGTTGTTAA AATTGATTTG GTACGTCTGG
1861 ATTTTTTTTC AAATAATACC GCTCCATCAA ATTTAGATTA ATATGATGTA ATATGCACAA
1921 TTAGAATTGC GGACAATTGT AACCAATTTA ATGAATTCAA AATTATTTCA TTGTAACAAG
1981 CAAATAGTAA AAAATAAAAT TATTATTATG AACAAATAAA AAGGGACAAG GCATAAGTAC
2041 TCTCCTAGAC TATGACTGAA ATCTCAGAAA CACACATAAA CTTAACTAGG GTCCTATTAC
2101 CCCCTAAACT AATTTAAAAT GGAATAAATA CACCACAAAC GGTGACATGA CATAGAGAGT
2161 GTACACACTC TATTGAAGGC AATTGATTAG TGCACAAATT GGACACATGT CATTTTTTTA
2221 TTGATAACTT TATTATTAGT TAGTACACAT ATTTATTGAT AATAAAAATT ATATATATAT
2281 AATTATTTTT ATTTCTTTCT TTGTAAAATA TTTATTTTAA TTTCTTTTTA CTTTAAACTT
2341 TTTTTTATTT AATTTATTAT GTTTTCACTT TTGATTATTT AAAAAAAATT TATGTGTATT
2401 TTTTAAAAAA GTAATTTTAA AGTGTCCTTT AATTTAATG TTTTAACTTT TTTATGTTTT
2461 ATTTGAATTT CTTCACTTAT TTTAATATCC GTTCAATTTA ATGAATCCTA AATTATTTCA
2521 TTGTAACAAG TAAATAGAAA AAAATAAAT AAGTCTTATG AAGAAATAAA AACAAATATA
2581 TTTTTTCCAC AAGTTGTGTA ATGATTGTTG AAGATGCTTC CATTTTTTAA ATCTTTTCTC
2641 AATATATATT TTCCACAAGT TGTGCAATGA TTGCTGAAGT TGCTTTATTG TTTTAAGACT
2701 TTTCTCTATA TGTGTTTTTC CCCAAGTTGT ATAATGGTTG TTGAAGATGC TTTAATTAAA
2761 AAAAAAAACC TTTTGTTTAG TGGAAAATTT CAAAAAGCTT TAGTACATCT TTGTCGTTTT
2821 ATCCAATCGT AATTCTTTAT TCAGAAACCA CATGTTTTTT TTCTAATCTT ACTTTTATGT
2881 CTATCACCCA TTTTCCAATA TACAGCCTAC TCTTTTTTTC AATCAAACT AGTATTCCTA
2941 AAGatggctg atgcctttct atcatttgca gttcaaaaat tgggtgattt cctaatacag
3001 aaagtttccc tgcgtaaaag tctcagagat gaaattagat ggctgataaa tgagctactc
3061 ttcatacggt ctttcctcag agatgcagaa caaaagcagt gcggagatca aagagttcaa
3121 caatgggtgt ttgagatcaa ctctattgct aatgatgctg ttgctatact cgagacttat
3181 agctttgagg ctggtaaagg tgctagtcgt ctcaaggctt gcacttgcat atgtaggaag
3241 gagaagaaat tctacaatgt tgccgaggag attcaatcac tcaagcaacg aatcatggat
3301 atctctcgca aacgagagac ttatggtatt acaaatatca attataattc aggagaaagg
```

Fig. 8-2

```
3361 ccaagtaatc aggttacaac attgaggaga actacctcat atgtagatga acaggattac
3421 attttgttg gctttcagga tgttgtacaa acattgctag ctcaacttct gaaagcagag
3481 cctcgtcgaa gcgtcctctc catttatgga atgggggtt taggcaagac cactcttgcc
3541 agaaaacttt acaccagtcc tgatatactc aatagctttc ctacacgcgc ttggatatgt
3601 gtctctcaag agtacaacac aatggatctt cttaggacta tcataaaatc catccaaggc
3661 tgcgccaagg aaactctaga tttgttggaa aagatggcag aaatagatct agaaaatcac
3721 cttcgtgatc tattgaaaga atgcaaatac cttgtggtgg ttgatgatgt atggcagaga
3781 gaagcatggg agagtttgaa aagagcattc ccggatggca agaatggaag cagagtcatt
3841 attaccacgc gcaaagagga tgtcgctgaa agagtagacc acagaggttt tgttcataaa
3901 cttcgtttcc taagtcaaga agaaagttgg gatctctttc gtaggaaact acttgatgtt
3961 cgagcaatgg ttccagaaat ggaaagttta gctaaggata tggtggaaaa gtgtagaggc
4021 ttacctcttg caattgttgt attgagcgga ctactttcgc ataaaaaggg gctaaaccaa
4081 tggcaaaagg tgaaagatca cctttggaag aacattaaag aagataaatc tattgaaatc
4141 tctaacatac tatccttaag ctacaatgat ttgtcaactg cgctcaagca gtgttttctc
4201 tactttggta tttttccaga agatcaagtg gtaaaggctg atgacataat acggttgtgg
4261 atggcggagg gtttcatacc cagaggagaa gaaagaatgg aggatgtggc tgacggcttc
4321 ttgaatgaac tgataagacg aagcttggtt caagtagcta aaacattttg ggaaaaagtt
4381 actgactgta gggttcatga tttacttcgt gatcttgcga tacaaaaggc attggaggta
4441 aacttctttg acgtttatgg tccaagaagc cactccatat cctctttatg tatcagacat
4501 ggcattcata gtgaaggaga aaggtacctc tcatcacttg atctttctaa cttgaagttg
4561 aggtcaatta tgttcttcga tccagatttt cgtaagatga gtcatataaa cctcaggagt
4621 gagttccaac atctgtatgt gttgtacttg gatacgaatt ttgggtatgt gtctatggta
4681 cctgatgcca taggaagttt gtaccacctc aagttgttaa gattgagagg tatccatgat
4741 attccgtctt ccattggcaa cctcaagaat ttacaaacac ttgtcgttgt aaatggttac
4801 acatttttt gccaactacc ctgcaagaca gctgacctaa taaatctaag acatttagtt
4861 gttcaatatt cagagccttt aaaatgtata aacaaactca ctagtcttca agttcttgat
4921 ggtgttgctt gtgatcagtg gaaagatgtt gaccctgttg atttagtcaa tcttcgagaa
4981 ttaagcatgg atcgtatcag gagctcttac tccctaaaca acattagcag cttgaaaaac
5041 cttagcactc tcaaattgat ttgtggagaa cgtcaatcat ttgcatccct tgaatttgtt
5101 aattgttgtg aaaagctcca gaattgtgg ttacaaggga gaatagagga actgcctcat
5161 ctgttttcaa actccatcac aatgatggtt ctgagttct cagaactgac agaagatccg
5221 atgcctattt tgggaaggtt tccaaaccta aggaatctca aattagatgg agcttatgaa
5281 ggaaaagaaa taatgtgcag tgataacagc ttcagtcaac tagagttcct tcatcttcgt
5341 gatctttgga agctagaaag atgggatta ggcacaagtg ccatgcctct gattaaaggt
5401 cttggtatcc ataactgtcc aaatttaaag gagattcctg agagaatgaa agacatggag
5461 ctgttgaagc ggaattatat gttgtgaAGC TTTTCTGCCA AGCACATTGG TTATTAATTG
5521 AGTGGTTTTA GTGTTGATTT CTTATTATTG TTTTAAGCTT TTTGAGTGTG TAATTGGTTT
5581 GAACATTATT GTTTTAATTA ATTGGTCTAC TGTATGTTCT CATGCTTATC CACATTTAAG
5641 ACAATGCTTT ATATGTTAAA ATGAAATTAA AAATACTAGT ATATGGTACT CTCTCTTGTC
5701 CACAATTTCG TATATTTTT GTTCCTCTTC ATAAAAAAAA TGGTAAAAAA TACCATTAAA
5761 CTATGTGATA GGAACAAAAA TGTCTTCTAT TATAATTTAA CTTAAAAATG TCTTTACTGT
5821 CAGTACCTTA GTTCAAAATT GCCCTCGAGT CCGTAGTTAC AAAATGTCCT TTTTCGAATA
5881 AATATATATA TTTTTTTAAA CACATCTTCT TCCTAATTAA ATATTATTA AGAAGACTA
5941 TTCTTGTTTT CTTTTTTCTA AAAATCACTT TAACAAATAA AAATGTAGGA ATATTTTGT
6001 TTTCTTCTTA ATCTCACTTT ATCAATTAAA ATAGAATAAC TCCATGTACC CTTTCGACAT
6061 ATAATATATG TCATATATAT ATATAAGATC ATAGTATATG CATCATTAAT TTATATTTAT
6121 ATAACGATAA AAAATAATGA TAATAAAATA AGAATATTTT TTATTTTTA TTTTCTTCTG
6181 AATTGAAGTA ATATAAACAT TTGCTAATTT TAAAAAAAAA TAATACAAAA ATAATGTGTT
6241 AAAAAGAAAA TAATAATATA TTTATTTGGA AAATGAGTAT TTTTGATCCA TTAAATAACA
6301 GTAAGTGTAT TTTTAGACCA AAGTATTGAC AACAAGGGTA TTTTTGGATC AAACGACAAA
6361 CGGAGGGTAC TTTTGCTCCT TTCGCATAAT TTAAGGGTAT TTTTAAACCA AAATATTGAC
6421 GGTAAAGGCA TTTTTGAGTC AAATTATGAA CGAAAGACAT TTTTATTTCT TTCACATAGT
6481 TTAAGGACAT TTTTGACCCA TTTCCCTCCT TTATATAAAT AATATTTATG TTAAATCAAC
```

Fig. 8-3

```
6541 AGAGAAGAAG CTGTCAATTG AAGACATTCA CTTTCATCAA CTTGGCTTCT CCAAGCATCA
6601 ATCAACTTGG ATTATTTCAA CATTCTGTTT TTTCAATGTT TAATTTCTTT CTATTTTTGG
6661 AAACATGTGT TGGAAGAGAA CCTTTTTTCT GGATTTTGTG ATGACCTAAT TAACGAAACA
6721 AAGTTAAAAA TGTTCTTAAA TTATGTAAAA TGAATAAAAA TATCCTCAGT TAATAGTTTG
6781 ATCCAAAAAT ATTGTTGTCT CTAATAATTG ATCTAAAAAT GATATTATTG TTACTTAATA
6841 AGTGAAAACC GTCTTTTTTT CAATTAAATA TATTATTTTT CTTTTTTTAA AACACGCTCT
6901 TTTCCTAATA ATGATTTTTT TTCATTAAAA AATATTCATC CTACTTCAAT TTATAAAAAA
6961 TATTACTAAT AAATAAAAAT GTTTTTTATA TTATTAGAAA GTTTTTTATC GTTATTTAAA
7021 TGAAAATTAA TGACGGGGTT ACTATGAGGA CATATAATGG AAGAAGTTGA GAACTCGCTT
7081 AGTGTGAAGC GAGAATAACT AAAAAAAAAA AAAAAACTTA CAAACTCGCT TGGTGCGGAG
7141 CGATTTTTGG GGGAAAATAG AGAGCAAATC GCTCATAGGT AGCGAGAAAA AAAAGATAAA
7201 ATAAAAGAGA AAATCGCTCG TAAGTCAACA AGATGATCAA TTTTTTTATG CCGTTAACGA
7261 TAGTTATAGC ACAAACATAT CTCGCTCCTT CTCTAGCAAA GTGTCCCTTT TGATTAAACC
7321 AAAAATTGAA AGACCCTTTA TGTATTTTAA AGAAAAAAAG TGATGTTTTT AACTTTGAAT
7381 TCGAAATTTA ATCATCCCAA TATAATTCAT AAACGAATTT TTACATCAAT TTTAAAATAA
7441 AGAATAAAAA AAAGAAAGAT AATATATACT AGCAGGGAAC TACATGTGAT TACTACAAAA
7501 GATAAATTCA ATTTCAGGTG GTATTTGGAT TTGAATTGTC TTACCTTGCT ATCATAACAT
7561 TATTTTTGTT TTTATCCATT AAAAAAATGA TGCATTTATA TATTTATTAC TAGTAAAGTA
7621 ATATCTTTAA TGTGTCAACA CATAAGTATC CCTCAATTAG TAAAATGTTA GGACTTTTTT
7681 CATGTGAGAA ACCCAACCTC ATTGAAAAAG GAAATTAATA CATTTTAACT CAACTTTTAA
7741 TTAATTAATG TCAAGTTTGA TAAAAATAAA TAAAAAAACA ATCGTAGACA ATCTCTAATT
7801 ATTAGAATTT TACAATATGC ATATTTAATG GGTTATATAA ATTTTGAGTT GGCCTTCTTT
7861 TTTTCTTCTT GTGATTCTAA GTCCTCCACT TTATTTTTAT TTTTATATTT ATAATTAAAT
7921 ATTTTTTACT CGATTCACAG ACCGAGTTGG ACCAGTCCAA TCTTGATTAA GCCTCACGAG
7981 TTGACGAGCT TATTTAGGCT TGGCTAAATA ATTTCGTTCT TAAATGAACT TTTAATTTTT
8041 TTTGAGCTCA ATCCTATCAA ATCGCAGATT AGGTTGGATT TGGGTGAAAC AATGGACCAA
8101 AGTCCAAACT AACAGCTCCA AAATCTACGA GGTTTAGAAA TAGAAAGTCT TCTTATATGT
8161 TATGTATATC TAACAAATTA TATGTTATGT ATGATATTGT ATAAATAGTT ATTTAATGTA
8221 TCAATATTGT ATAATAACAT ATAGTTATGT ATTTATAATG TATAACTATA TATGATATTG
8281 TATAAATAGT TATTTAATGT ATCGATATTG TATAGTAGCA TATAGTTATG TATTTATAAT
8341 GTATGTATAA CTATGTATGA TATTGTATAA ATAGATTTTG GACTTGGGAA GTCTGCAGCA
8401 AGCAAAGGAA GAGGTCCAGG TAGCAACACT TTTATCTTAA TGAATACACC AAATGATGAT
8461 C
```

Fig. 9

```
         ATGGCTGATGCCTTTCTATCATTTGCAGTTCAAAAATTGGGTGATTTCCTAATACAGAA
AGTTTCCCTGCGTAAAAGTCTCAGAGACGAAATTAGATGGCTGATCAATGAGCTACTCTTCATACGGT
CTTTCCTCAGAGATGCAGAACAAAAGCAGTGCGGAGATCAAAGAGTTCAACAATGGGTGTTTGAGATC
AACTCTATTGCTAATGATGCTGTTGCTATACTCGAGACTTATAGCTTTGAGGCTGGTAAAGGTGCTAG
TCGTCTCAAGGCTTGCACTTGCATATGTAGGAAGGAGAAGAAATTCTACAATGTTGCCGAGGAGATTC
AATCACTCAAGCAACGAATCATGGATATCTCTCGCAAACGAGAGACTTATGGTATTACAAATATCAAT
AATAATGCAGGAGAAGGGCCAAGTAATCAGGTTACAAAATTGAGGAGAACTACCTCATATGTAGATGA
ACAGGATTACATTTTGTTGGCTTTCAGGATGTTGTACAAACATTTCTAGCTCAACTTCTGAAAGCAG
AGCCTCGTCGAAGCGTCCTCTCCATTTATGGAATGGGGGGTTTAGGCAAGACCACTCTTGCCAGAAAA
CTTTACACCAGTCCTGATATACTCAATAGCTTCCGTACACGCGCTTGGATATGTGTCTCTCAAGAGTA
CAACACAATGGATCTTCTTAGGAATATCATAAAATCCATCCAAGGTCGCACCAAGGAAACTCTAGATT
TGTTGGAAAGGATGACAGAAGGAGATCTTGAAATTTATCTTCGTGATTTATTGAAAGAACGCAAATAC
CTTGTGGTGGTTGATGATGTATGGCAGAGAGAAGCATGGGAGAGTTTGAAAAGATCATTCCCGGATGG
CAAGAATGGCAGCAGAGTCATTATTACCACGCGCAAAGAGGATGTCGCTGAAAGAGCAGACGACAGAG
GTTTTGTTCATAAACTTCGTTTCCTAAGCCAAGAAGAAAGTTGGGATCTCTTTCGTAGGAAACTACTT
GATGTTCGAGCAATGGTTCCAGAAATGGAAAGTCTAGCTAAGGATATGGTGGAAAAGTGTAGAGGCTT
ACCTCTTGCAATTGTTGTATTGAGCGGACTACTTTCGCATAAAAAGGGGCTAAACCAATGGCAAAAGG
TGAAAGATCACCTTTGGAAGAACATTAAAGAAGATAAATCTATTGAAATCTCTAACATACTATCCTTA
AGCTACAATGATTTGTCAACTGCGCTCAAGCAGTGTTTTCTCTACTTTGGTATTTTTCCAGAAGATCA
AGTGGTAAAGGCTGATGACATAATACGGTTGTGGATGGCGGAGGGTTTCATACCCAGAGGAGAAGAAA
GAATGGAGGATGTGGCTGACGGCTTCTTGAATGAACTGATAAGACGAAGCTTGGTTCAAGTAGCTAAA
ACATTTTGGGAAAAGTTACTGACTGTAGGGTTCATGATTTACTTCGTGATCTTGCGATACAAAAGGC
ATTGGAGGTAAACTTCTTTGACATTTATGATCCAAGAAGCCACTCCATATCCTCTTTATGTATCAGAC
ATGGCATTCATAGTGAAGGAGAAAGGTACCTCTCATCACTTGATCTTTCTAACTTGAAGTTGAGGTCA
ATTATGTTCTTCGATCCATATATTTGTAATGTGTTCCAACATATAGATGTGTTTCGACATCTATATGT
GTTGTACTTGGATACGAATTTTGGGTATGTGTCTATGGTACCTGATGCCATAGGAAGTTTGTACCACC
TCAAGTTGTTAAGATTGAGAGGTATCCATGATATTCCGTCTTCCATTGGCAACCTCAAGAATTTACAA
ACACTTGTCGTTGTAAATGGTTACACATTTTTTTGCGAACTACCCTGCAAGACAGCTGACCTAATAAA
TCTAAGACATTTAGTTGTTCAATATACAGAGCCTTTAAAATGTATAAACAAACTCACTAGTCTTCAAG
TTCTTGATGGTGTTGCTTGTGATCAGTGGAAAGATGTTGACCCTGTTGATTTAGTCAATCTTCGAGAA
TTAAGCATGGATCGTATCAGGAGCTCTTACTCCCTAAACAACATTAGCAGCTTGAAAAACCTTAGCAC
TCTCAAATTGATTTGTGGAGAACGTCAATCATTTGCATCCCTTGAATTTGTTAATTGTTGTGAAAAGC
TCCAGAAATTGTGGTTACAAGGGAGAATAGAGGAACTGCCTCATCTGTTTTCAAACTCCATCACAATG
ATGGTTCTGAGTTTCTCAGAACTGACAGAAGATCCGATGCCTATTTTGGGAAGGTTTCCAAACCTAAG
GAATCTCAAATTAGATGGAGCTTACGAAGGAAAAGAAATAATGTGCAGTGATAACAGCTTCAGTCAAC
TAGAGTTCCTTCATCTTCGTGATCTTTGGAAGCTAGAAAGATGGGATTTAGGCACAAGTGCCATGCCT
CTGATTAAAGGTCTTGGTATCCATAACTGTCCAAATTTAAAGGAGATTCCTGAGAGAATGAAAGACGT
GGAGCTGTTGAAGCGGAATTATATGTTGTGA
```

Fig. 10

```
ATGGCTGATGCCTTTCTATCATTTGCAGTTCAAAAATTGGGTGATTTCCTCATTCAACAAGT
TTCTCTGCGTAAAAATCTGAGAAAGGAAATTGAGTGGCTGAGAAATGAGCTACTCTTCATACAGTCTT
TCCTCAGAGATGCAGAACTAAAGCAATATGGAGATCAAAGAGTTCAACAATGGGTGTTTGAGATCAAC
TCTATTGCTAATGATGTTGTTGCTATACTCGAGACTTACACCTTCGAGGCTGGTAAAGGTGCTAGTCG
TCTCAAGGCTTGCGCTTGCATATATACGAAGGAGAAGAAATTCTACAATGTTGCCGAGGAGATCCAAT
CACTCAAGCAACGAATCATGGATATCTCTCGCAAACGAGAGACTTATGGTATTACAAATATCAATAAT
AATTCAGGAGAAGGGCCAAGTAATCAGGTTAGAACATTGAGGAGAACTACCTCATATGTGGATGACCA
GGATTACATTTTTGTTGGACTTCAGGATGTTGTACAAAAATTGCTAGCTCAACTTCTCAAAGCAGAGC
CCCGTCGAACCGTCCTCTCCATTCATGGCATGGGCGGATTGGGCAAGACCACTCTTGCGAGAAAACTT
TACAACAGTTCTGCTATACTCAATAGCTTCCCTACACGCGCTTGGATATGTGTCTCTCAAGAGTACAA
CACAATGGATCTTCTTAGGAATATCATAAAATCCGTCCAAGGTCGCACCAAGGAAACTCTAGATTTGT
TGGAAAGGATGACAGAAGGAGATCTAGAAATCTATCTTCGTGATCTATTAAAAGAACGCAAATACCTT
GTGATGGTTGATGATGTATGGCAGAAAGAAGCATGGGATAGTTTGAAGAGAGCATTCCCGGATAGCAA
GAATGGCAGCAGAGTCATTATTACCACGCGCAAACAGGATGTCGCTGAAAGAGCAGACGACATAGGTT
TTGTTCATAAACTTCGTTTCCTAAGTCAAGAAGAAAGTTGGGATCTCTTTCGTAAGAAACTACTTGAT
GTTCGATCAATGGTTCCAGAAATGGAAAATCTAGCTAAGGATATGGTGGAAAAGTGTAGAGGCTTACC
TCTTGCAATTGTTGTATTGAGCGGACTACTTTCGCATAAAAAGGGGCTAAACCAATGGCAAAAGGTGA
AAGATCACCTTTGGAAGAACATTAAAGAAGATAAATCTATTGAAATCTCTAACATACTATCCTTAAGC
TACAATGATTTGTCAACTGCGCTCAAGCAGTGTTTTCTCTACTTTGGTATTTTTCCAGAAGATCAAGT
GGTAAAGGCTGATGACATAATACGGTTGTGGATGGCGGAGGGTTTCATACCCAGAGGAGAAGAAAGAA
TGGAGGATGTGGCTGACGGCTTCTTGAATGAACTGATAAGACGAAGCTTGGTTCAAGTAGCTAAAACA
TTTTGGGAAAAGTTACTGACTGTAGGGTTCATGATTTACTTCGTGATCTTGCGATACAAAAGGTATT
GGAGGTAAACTTCTTTGACATTTATGATCCAAGAAGCCACTCCATATCCTCTTTATGTATCAGACATG
GCATTCATAGTGAAGGAGAAAGGTACCTCTCATCACTTGATCTTTCTAACTTGAAGTTGAGGTCAATT
ATGTTCTTCGATCCATATATTTGTAATGTGTTCCAACATATAGATGTGTTTCGACATCTATATGTGTT
GTACTTGGATACGAATTTTGGGTATGTGTCTATGGTACCTGATGCCATAGGAAGTTTGTACCACCTCA
AGTTGTTAAGATTGAGAGGTATCCATGATATTCCGTCTTCCATTGGCAACCTCAAGAATTTACAAACA
CTTGTCGTTGTAAATGGTTACACATTTTTTTGCGAACTACCCTGCAAGACAGCTGACCTAATAAATCT
AAGACATTTAGTTGTTCAATATACAGAGCCTTTAAAATGTATAAACAAACTCACTAGTCTTCAAGTTC
TTGATGGTGTTGCTTGTGATCAGTGGAAAGATGTTGACCCTGTTGATTAGTCAATCTTCGAGAATTA
AGCATGGATCGTATCAGGAGCTCTTACTCCCTAAACAACATTAGCAGCTTGAAAAACCTTAGCACTCT
CAAATTGATTTGTGGAGAACGTCAATCATTTGCATCCCTTGAATTTGTTAATTGTTGTGAAAAGCTCC
AGAAATTGTGGTTACAAGGGAGAATAGAGGAACTGCCTCATCTGTTTTCAAACTCCATCACAATGATG
GTTCTGAGTTTCTCAGAACTGACAGAAGATCCGATGCCTATTTTGGGAAGGTTTCCAAACCTAAGGAA
TCTCAAATTAGATGGAGCTTACGAAGGAAAAGAAATAATGTGCAGTGATAACAGCTTCAGTCAACTAG
AGTTCCTTCATCTTCGTGATCTTTGGAAGCTAGAAAGATGGGATTTAGGCACAAGTGCCATGCCTCTG
ATTAAAGGTCTTGGTATCCATAACTGTCCAAATTTAAAGGAGATTCCTGAGAGAATGAAAGACGTGGA
GCTGTTGAAGCGGAATTATATGTTGTGA
```

Fig. 11

```
ATGGCTGATGCCTTTCTATCATTTGCAGTTCAAAAATTGGGTGATTTCCTAATACAGAAAGTTTCCCT
GCGTAAAAGTCTCAGAGATGAAATTAGATGGCTGATCAATGAGCTACTCTTCATACGGTCTTTCCTCA
GAGATGCAGAACAAAAGCAGTGCGGAGATCAAAGAGTTCAACAATGGGTGTTTGAGATCAACTCTATT
GCTAATGATGCTGTTGCTATACTCGAGACTTATAGCTTTGAGGCTGGTAAAGGTGCTAGTCGTCTCAA
GGCTTGCACTTGCATATGTAGGAAGGAGAAGAAATTCTACAATGTTGCCGAGGAGATTCAATCACTCA
AGCAACGAATCATGGATATCTCTCGCAAACGAGAGACTTATGGTATTACAAATATCAATAATAATGCA
GGAGAAGGGCCAAGTAATCAGGTTACAAAATTGAGGAGAACTACCTCATATGTAGATGAACAGGATTA
CATTTTTGTTGGCTTTCAGGATGTTGTACAAACATTTCTAGCTCAACTTCTGAAAGCAGAGCCTCGTC
GAAGCGTCCTCTCCATTTATGGAATGGGGGGTTTAGGCAAGACCACTCTTGCCAGAAAACTTTACACC
AGTCCTGATATACTCAATAGCTTCCGTACACGCGCTTGGATATGTGTCTCTCAAGAGTACAACACAAT
GGATCTTCTTAGGAATATCATAAAATCCATCCAAGGTCGCACCAAGGAAACTCTAGATTTGTTGGAAA
GGATGACAGAAGGAGATCTTGAAATTTATCTTCGTGATTTATTGAAAGAACGCAAATACCTTGTGGTG
GTTGATGATGTATGGCAGAGAGAAGCATGGGAGAGTTTGAAAAGATCATTCCCGGATGGCAAGAATGG
CAGCAGAGTCATTATTACCACGCGCAAAGAGGATGTCGCTGAAAGAGCAGACGACAGAGGTTTTGTTC
ATAAACTTCGTTTCCTAAGCCAAGAAGAAAGTTGGGATCTCTTTCGTAGGAAACTACTTGATGTTCGA
GCAATGGTTCCAGAAATGGAAAGTCTAGCTAAGGATATGGTGGAAAAGTGTAGAGGCTTACCTCTTGC
AATTGTTGTATTGAGCGGACTACTTTCGCATAAAAAGGGGCTAAACCAATGGCAAAAGGTGAAAGATC
ACCTTTGGAAGAACATTAAAGAAGATAAATCTATTGAAATCTCTAACATACTATCCTTAAGCTACAAT
GATTTGTCAACTGCGCTCAAGCAGTGTTTTCTCTACTTTGGTATTTTTCCAGAAGATCAAGTGGTAAA
GGCTGATGACATAATACGGTTGTGGATGGCGGAGGGTTTCATACCCAGAGGAGAAGAAAGAATGGAGG
ATGTGGCTGACGGCTTCTTGAATGAACTGATAAGACGAAGCTTGGTTCAaGTAGCTAAAACATTTTGG
GAAAAAGTTACTGACTGTAGGGTTCATGATTTACTTCGTGATCTTGCGATACAAAAGGCATTGGAGGT
AAACTTCTTTGACATTTATGATCCAAGAAGCCACTCCATATCCTCTTTATGTATCAGACATGGCATTC
ATAGTGAAGGAGAAAGGTACCTCTCATCACTTGATCTTTCTAACTTGAAGTTGAGGTCAATTATGTTC
TTCGATCCAGATTTTCGTAAGATGAGTCATATAAACCTCAGGAGTGAGTTCCAACATCTATATGTGTT
GTACTTGGATACGAATTTTGGGTATGTGTCTATGGTACCTGATGCCATAGGAAGTTTGTACCACCTCA
AGTTGTTAAGATTGAGAGGTATCCATGATATTCCGTCTTCCATTGGCAACCTCAAGAATTTACAAACA
CTTGTCGTTGTAAATGGTTACACATTTTTTTGCGAACTACCCTGCAAGACAGCTGACCTAATAAATCT
AAGACATTTAGTTGTTCAATATACAGAGCCTTTAAAATGTATAAACAAACTCACTAGTCTTCAAGTTC
TTGATGGTGTTGCTTGTGATCAGTGGAAAGATGTTGACCCTGTTGATTTAGTCAATCTTCGAGAATTA
AGCATGGATCGTATCAGGAGCTCTTACTCCCTAAACAACATTAGCAGCTTGAAAAACCTTAGCACTCT
CAAATTGATTTGTGGAGAACGTCAATCATTTGCATCCCTTGAATTTGTTAATTGTTGTGAAAAGCTCC
AGAAATTGTGGTTACAAGGGAGAATAGAGGAACTGCCTCATCTGTTTTCAAACTCCATCACAATGATG
GTTCTGAGTTTCTCAGAACTGACAGAAGATCCGATGCCTATTTTGGGAAGGTTTCCAAACCTAAGGAA
TCTCAAATTAGATGGAGCTTACGAAGGAAAAGAAATAATGTGCAGTGATAACAGCTTCAGTCAACTAG
AGTTCCTTCATCTTCGTGATCTTTGGAAGCTAGAAAGATGGGATTTAGGCACAAGTGCGATGCCTCTG
ATTAAAGGTCTTGGTATCCATAACTGTCCAAATTTAAAGGAGATTCCTGAGAGAATGAAAGACGTGGA
GCTGTTGAAGCGGAATTATATGTTGTGA
```

FUNCTIONAL R-GENE FROM *SOLANUM BULBOCASTANUM*

CROSS-REFERENCE TO RELATED APPLICATIONS

This application is the national phase of PCT application PCT/NL2008/050050 having an international filing date of 28 Jan. 2008, which claims benefit of European application No. 07101270.2 filed 26 Jan. 2007. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 313632007100Seqlist.txt | Oct. 1, 2010 | 98,264 bytes |

TECHNICAL FIELD

The invention relates to a resistance gene isolated from *S. bulbocastanum*. Moreover, the invention relates to the use of said resistance gene, for example to clone functional homologues, and the use of said resistance gene(s) in a method to increase or confer at least partial resistance to an oomycete infection in a plant. More in specific the invention provides a resistance gene that is capable of increasing or conferring at least partial resistance to *Phytophthora* (for example *Phytophthora infestans*).

BACKGROUND ART

Late blight, caused by the oomycete *Phytophthora infestans* is one of the most serious diseases in worldwide potato production. It was responsible for the Irish potato famine of the mid-19th century, resulting in the death of one million people. Although a lot of effort has been invested in controlling the pathogen, chemical control of *P. infestans* is still the main crop management strategy, but environmental safety is becoming more important and the pathogen is sometimes able to evolve chemical resistance. Therefore, introduction of resistance into modern potato varieties is the most durable strategy to control the disease.

In the last century, *Solanum demissum*, which is a hexaploid Mexican species, was extensively used in breeding for late-blight resistance in potato. Initially, a series of 11 R genes derived from *S. demissum* was described. Of these, R1, R2, R3a/b, R6, and R7 have been localized on the genetic maps of potato. However, these R genes confer race-specific resistance and those that were introgressed into potato varieties, mainly R1, R2, R3, R4, and R10, were quickly overcome by the pathogen. Hence, new sources for resistance are required, and currently, several other wild *Solanum* species have been reported as being potential sources of resistance, many of which have currently been genetically characterized (Table 1).

*S. bulbocastanum*, a self-incompatible diploid species from Mexico, is thought to be a source for late-blight resistance. Introduction of *S. bulbocastanum* derived resistance has been achieved through interspecific bridge crosses between *S. bulbocastanum*, *S. acaule*, *S. phureja*, and *S. tuberosum* (Hermsen and Ramanna, Euphytica 22: 457-466, 1973), resulting in so-called ABPT material that is widely used for potato late-blight breeding. Additionally, Helgeson et al (Theor. Appl. Genet. 96:738-742, 1998) generated somatic hybrids between *S. bulbocastanum* and cultivated potato. The somatic hybrids led to fertile plants that retained resistance and could be used for breeding. Molecular cloning of the genes responsible for resistance and subsequent introduction of the genes into potato varieties is a third method that circumvents many of the problems encountered in the previous two strategies.

To date, two R genes from *S. bulbocastanum* have been cloned, the allelic genes RB and Rpi-blb1 on chromosome 8 (Song et al. Proc. Natl. Acad. Sci 100: 9128-9133, 2003; van der Vossen et al. Plant Journal 36: 867-882, 2003) and Rpi-blb2 on chromosome 6 (van der Vossen et al. Plant Journal 44: 208-222, 2005). As shown in Table 5, Rpi-blb1 as well as Rpi-blb2 provide protection against a diverse set of *Phytophthora infestans* isolates. Until the present invention no *Phytophthora* isolates were described that could colonize plants harboring Rpi-blb1, hence the specification 'broad spectrum resistance gene' was used to describe the protection conferred by this gene. However, as disclosed in Table 5, *Phytophthora* isolate 99189 is able to grow on Rpi-blb1 plants and thus to 'break' the resistance, suggesting race specificity.

DISCLOSURE OF THE INVENTION

Although the initial results obtained with RB and Rpi-blb1 and Rpi-blb2 are promising, there is a further need for additional R-genes. The present invention describes the cloning of a third late blight R gene from *S. bulbocastanum*. The Rpi-blb3 gene was mapped to an R gene hotspot on chromosome 4 in an intraspecific *S. bulbocastanum* mapping population. Markers highly linked to Rpi-blb3 were used to generate a physical map of the R locus. Two R gene candidates (RGC) present on one of two BAC clones that encompassed the Rpi-blb3 locus were targeted for complementation analysis, one of which turned out to be the functional Rpi-blb3 gene. Surprisingly, Rpi-blb3 shares the highest amino acid sequence identity (34.9%) to RPP13 from *Arabidopsis thaliana* and very little homology to any R gene previously identified within the Solanaceae.

As shown in Table 5, the 3 R genes cloned from *S. bulbocastanum* give differential reactions to the isolates 99177 and 99189 and hence it is concluded that these 3 R-genes are functionally different. Moreover, due to the large sequence differences it is likely that the 3 R-genes recognise different effectors from *Phytophthora*. This is confirmed by the fact that Rpi-blb1 recognises ipiO whereas the two other R-gene products do not recognise this *Phytophthora* effector.

DESCRIPTION OF THE DRAWINGS

FIG. 5. Phylogenetic tree based on the amino acid sequences of Rpi-blb3, Rpi-blb3 gene homologues amplified from late blight resistant potato clones harboring Rpi-abpt (AbptGH), R2-like (R2-likeGH) or R2 (R2GH), RGHs present on the tomato BAC clone AF411807, RPP13-Nd and Rpi-blb1. Boxed is the group containing Rpi-blb3, Rpi-abpt, R2 and R2-like.

FIG. 6. Amino acid sequence alignment of Rpi-blb3 (SEQ ID NO:35), Rpi-abpt (SEQ ID NO:37), R2-like (SEQ ID NO:41), R2 (SEQ ID NO:39), and a non functional R2 gene homologue R2GH-2 (SEQ ID NO:42). The full amino acid sequence of Rpi-blb3 and homologues is shown. Indicated are the 14 LRR repeats (1-14), in which the leucine(like) residues have been shown in bold.

FIG. 8. Nucleotide sequence of clone Blb25-B2 (8461 bp) (SEQ ID NO:34) containing the Rpi-blb3 gene and regulatory sequences. The Rpi-blb3 coding region of 2544 bp is highlighted in lower case (2944-5487). The upstream 2732 nt (211-2942) and the downstream 882 nt (5488-6370) harbour the regulatory sequences.

FIG. 9. Nucleotide sequence of the cds of Rpi-abpt (SEQ ID NO:36).

FIG. 10. Nucleotide sequence of the cds of R2 (SEQ ID NO:38).

FIG. 11. Nucleotide sequence of the cds of R2-like (SEQ ID NO:40).

MODES OF CARRYING OUT THE INVENTION

Figure 6:
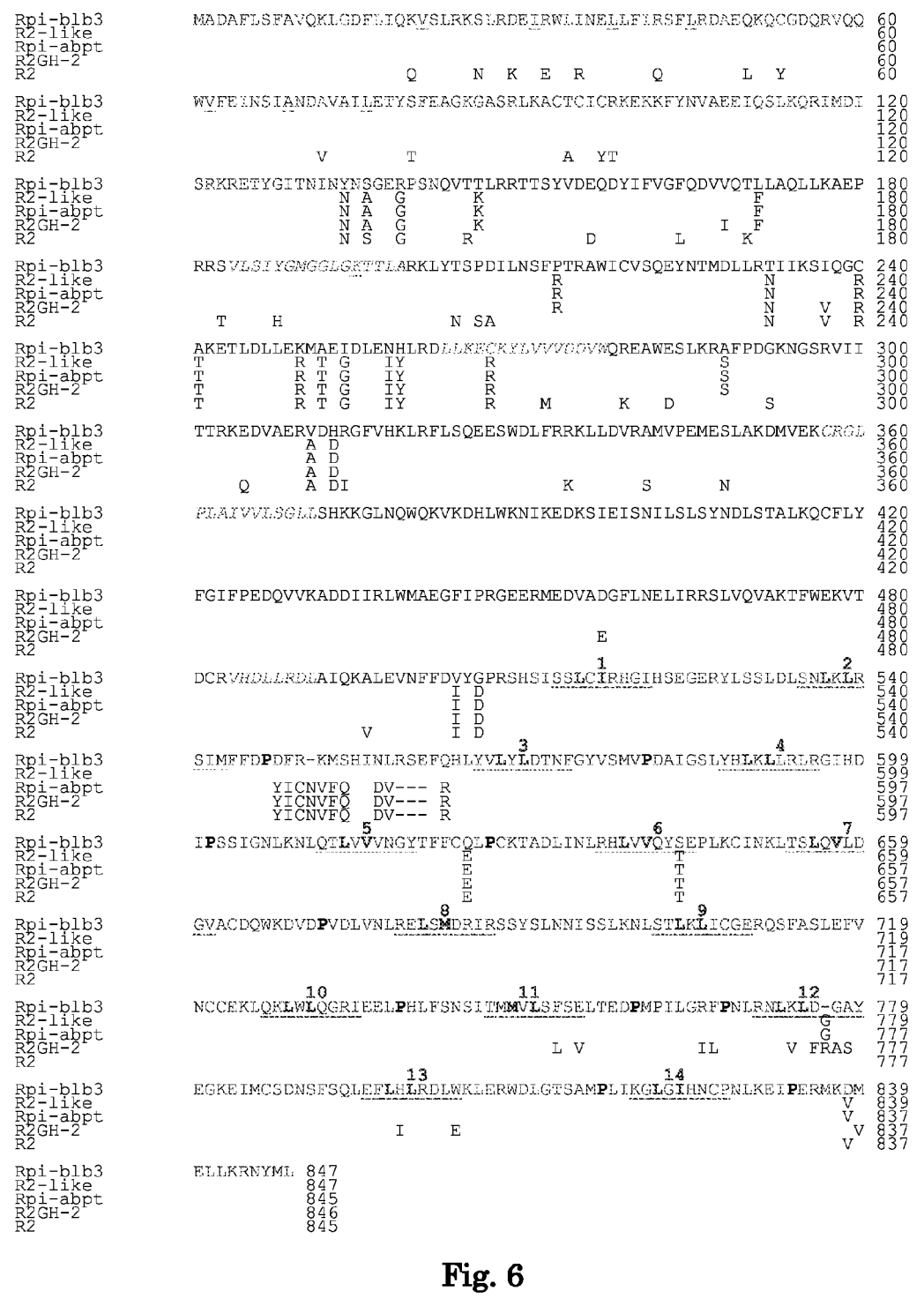
Figure 1A:
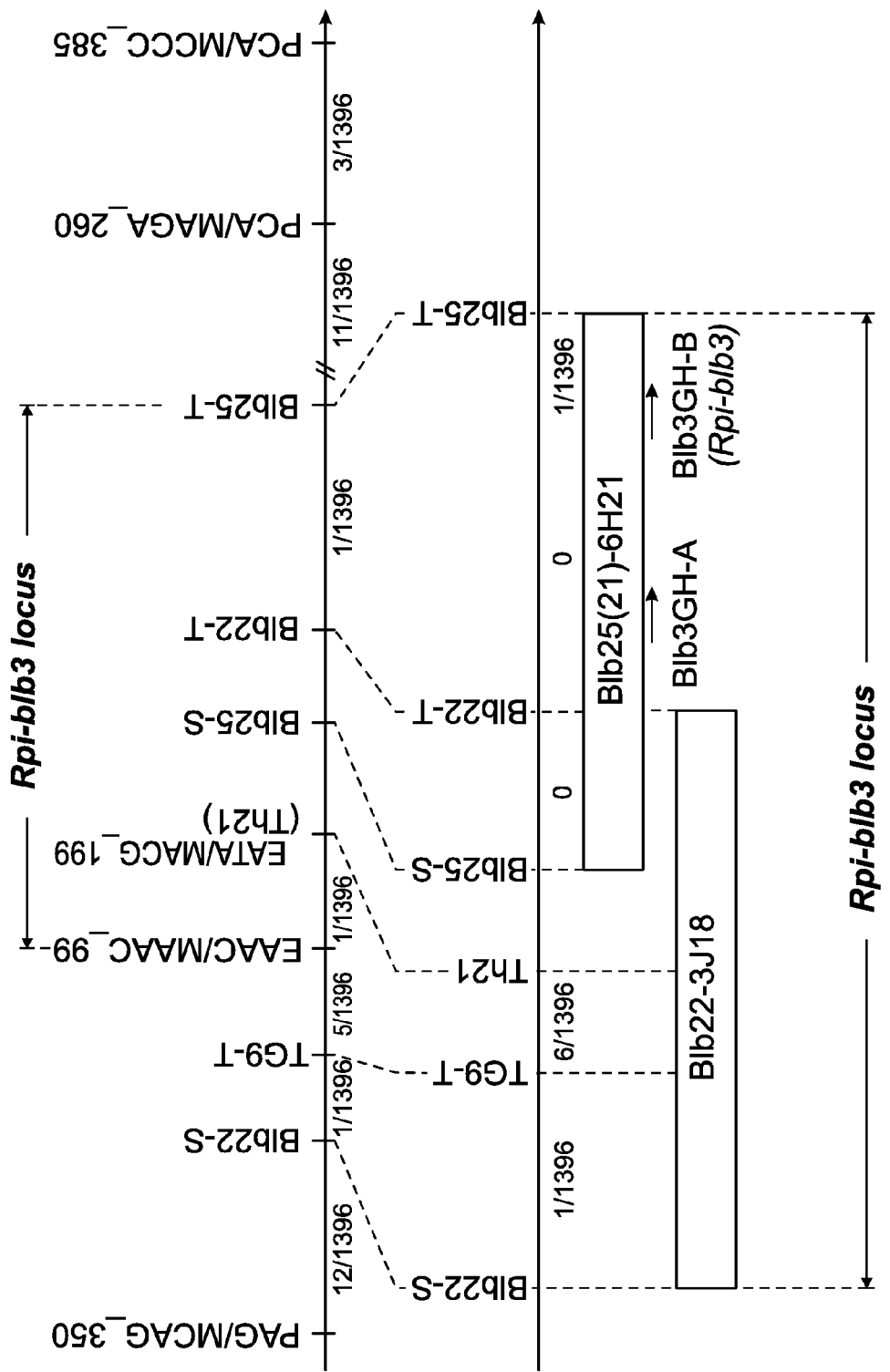
FIG. 1. Genetic and physical map of the Rpi-blb3 (A) and Rpi-abpt (B) loci. Indicated are the relative positions of markers, the number of recombinants identified between markers, overlapping BAC clones that span the R-loci, and the relative positions of candidate genes (Blb3 GH and AbptGH) that were targeted for complementation analysis.

In a first embodiment, the invention provides an isolated or recombinant nucleic acid sequence comprising a nucleic acid sequence encoding the amino acid sequence Rpi-blb3 of FIG. 6 or a functional fragment or a functional homologue thereof, i.e. a functional fragment or a functional homologue of the amino acid sequence as shown in FIG. 6.

The term "nucleic acid" means a single or double stranded DNA or RNA molecule.

Also included are the complementary sequences of the herein described nucleotide sequences.

The term "functional fragment thereof" is typically used to refer to a fragment of the Rpi-blb3 protein that is capable of providing at least partial resistance or increasing resistance in a plant of the Solanaceae family against an oomycte infection. Such a fragment is a truncated version of the Rpi-blb3 protein as presented in FIG. 6. A truncated version/fragment of the Rpi-blb3 protein is a fragment that is smaller than 847 amino acids and preferably comprises the larger part of the LRR domain (i.e. the larger part of the leucine-rich repeat domain which stretches from about amino acid 512 to amino acid 827 of Rpi-blb3) and/or the N-terminal parts of the Rpi-blb3 protein.

The term "functional homologue" is typically used to refer to a variant of the herein described Rpi-blb3 protein, which variant is capable of providing at least partial resistance or increasing resistance in a plant of the Solanaceae family against an oomycete infection. Included are artificial changes or amino acid residue substitutions that at least partly maintain the effect of the Rpi-blb3 protein. For example, certain amino acid residues can conventionally be replaced by others of comparable nature, e.g. a basic residue by another basic residue, an acidic residue by another acidic residue, a hydrophobic residue by another hydrophobic residue, and so on. Examples of hydrophobic amino acids are valine, leucine and isoleucine. Phenylalanine, tyrosine and tryptophan are examples of amino acids with an aromatic side chain and cysteine as well as methonine are example of amino acids with sulphur-containing side chains. Serine and threonine contain aliphatic hydroxyl groups and are considered to be hydrophilic. Aspartic acid and glutamic acid are examples of amino acids with an acidic side chain. In short, the term "functional homologue thereof" includes variants of the Rpi-blb3 protein in which a portion of the amino acids have been replaced conventionally and which at least partly maintain the effect of the Rpi-blb3 protein (i.e. at least partly providing or increasing resistance in a plant of the Solanaceae family against an oomycete infection). Also included in the term "functional homologue thereof" are homologous sequences. Preferably, such a homologue has at least 40% identity on the amino acid level. More preferably, the amino acid homology percentage is at least 86 or 90%. Even more preferred are amino acid homology percentages of 91, 92, 93, 94 or 95%. Most preferred are amino acid homology percentages of 96, 97, 98 or 99%.

A homologous nucleic acid sequence is a nucleic acid sequence that encodes for a homologous protein as described above. Homologous proteins and their respective nucleotide sequences are, for example, the genes denominated as Rpi-abpt, R2-like and R2, see FIG. 6 (amino acid sequence) and FIGS. 9-11 (nucleotide sequence).

Homology percentages can for example be determined by using computer programs such as BLAST, ClustalW or ClustalX.

Many nucleic acid sequences code for a protein that is 100% identical to the Rpi-blb3 protein as presented in FIG. 6. This is because the third nucleotide in a nucleotide triplet may vary without changing the corresponding amino acid (wobble position in the nucleotide triplets). Thus, without having an effect on the amino acid sequence of a protein the nucleotide sequence coding for this protein can be varied. However, in a preferred embodiment, the invention provides an isolated or recombinant nucleic acid sequence as depicted in FIG. 8. The Rpi-blb3 coding region of 2544 bp is highlighted in lower case (2944-5487). The upstream 2732 nt (211-2942) and the downstream 882 nt (5488-6370) harbour regulatory sequences. In a preferred embodiment, the invention provides an isolated or recombinant nucleic acid that represents the coding sequence (CDS) of the Rpi-blb3 protein, i.e. nucleotides 2944-5487 of FIG. 8 or a functional part or a functional homologue thereof.

Fragments as well as homologues of the herein described Rpi-blb3 gene and protein can for example be tested for their functionality by using *Agrobacterium tumefaciens* transient assays (ATTA) and/or by using a detached leaf assay.

The experimental part for example describes a functional screen for testing candidate genes using *Agrobacterium tumefaciens* transient assays (ATTA) whereby 4 week old wildtype *Nicotiana benthamiana* plants are infiltrated with an *Agrobacterium* strain containing the candidate Rpi-blb3 homologue. The infiltrated leaves are subsequently challenged one day after infiltration with a *P. infestans* strain that is virulent on *N. benthamina*, for example IPO-C or 90128, in detached leaf assays. This system is equally suitable for testing candidate homologous fragments of Rpi-blb3.

The ATTA assays make use of transient expression. Transient gene expression is a fast, flexible and reproducible approach to high-level expression of useful proteins. In plants, recombinant strains of *Agrobacterium tumefaciens* can be used for transient expression of genes that have been inserted into the T-DNA region of the bacterial Ti plasmid. A bacterial culture is infiltrated into leaves, and upon T-DNA transfer, there is ectopic expression of the gene of interest in the plant cells. However, the utility of the system is limited because the ectopic protein expression ceases after 2-3 days. It is shown that post-transcriptional gene silencing (PTGS) is a major cause for this lack of efficiency. A system based on co-expression of a viral-encoded suppressor of gene silencing, the p19 protein of tomato bushy stunt virus (TBSV), prevents the onset of PTGS in the infiltrated tissues and allows high level of transient expression. Expression of a range of proteins was enhanced 50-fold or more in the presence of p19 so that protein purification could be achieved from as little as 100 mg of infiltrated leaf material. Although it is clear that the use of p19 has advantages, an ATTA without p19 can also be used to test the functionality of candidate fragments and homologues.

Alternatively, each candidate gene (for example being a fragment or homologue) construct is targeted for transformation to a susceptible potato cultivar, for example Desiree. Primary transformants are challenged in detached leaf assays using for example isolates IPO-0, IPO-C or 90128. Transformants that are resistant to these isolates harbour for example functional fragments or homologues of Rpi-blb3.

In yet another embodiment, the invention provides a vector comprising a nucleic acid as provided herein, i.e. a nucleic acid capable of providing at least partial resistance or increasing resistance in a plant of the Solanaceae family against an oomycete infection. More particularly, the invention provides a vector comprising an isolated or recombinant nucleic acid sequence comprising a nucleic acid sequence encoding the amino acid sequence Rpi-blb3 of FIG. 6 or a functional fragment or a functional homologue thereof. The invention also provides a vector comprising a nucleic acid sequence as depicted in FIG. 8, preferably the coding sequence of FIG. 8, i.e. nucleotide 2944-5487.

Examples of a suitable vector are pBeloBACII, pBINPLUS, pKGW-MG or any commercially available cloning vector.

As will be outlined below there are multiple ways in which a nucleic acid of the invention can be transferred to a plant. One suitable means of transfer is mediated by *Agrobacterium* in which the nucleic acid to be transferred is part of a binary vector and hence it is preferred that the above described vector is a binary vector.

The invention further provides a host cell comprising a nucleic acid as described herein or a vector as described herein. Examples of a preferred host cell are an *E. coli* cell suitable for BAC clones (e.g. DH10B) or an *Agrobacterium* (host) cell. In an another embodiment, said host cell comprises a plant cell. A preferred plant cell is a cell derived from a member of the Solanaceae family and even more preferred said plant cell comprises a cell from *Solanum tuberosum* or *Solanum lycopersicum*, formerly known as *Lycopersicon esculentum*. From such a cell, a transgenic or genetically modified plant (for example a potato or tomato plant) can be obtained by methods known by the skilled person (for example regeneration protocols).

The invention further provides a leaf, tuber, fruit or seed or part or progeny of a genetically modified plant as described herein.

In yet another embodiment, the invention provides a protein encoded by the herein described isolated or recombinant nucleic acid or a functional fragment or a functional homologue thereof. In a preferred embodiment, the invention provides a protein encoded by a nucleic acid sequence as depicted in FIG. 8, preferably a protein encoded by nucleotides 2944-5487. In yet another preferred embodiment, the invention provides a protein comprising the amino acid sequence of FIG. 6 or a functional fragment or a functional homologue thereof.

The herein described Rpi-blb3 protein comprises 847 amino acids and the LRR domains of Rpi-blb3 consist of 14 imperfect repeats (FIG. 6). Interestingly Rpi-blb3 shares the highest homology with the RPP13 protein from *Arabidopsis thaliana* (Table 3) (Bittner-Eddy et al., Plant Journal 21: 177-188, 2000). The different domains of Rpi-blb3 share varying degrees of homology with corresponding domains of RPP13 (Table 3). The NBS domain is most conserved (48.2% aa identity), followed by the CC domain (34.4% aa identity). The LRR domain is least conserved (21.5% aa identity) (Table 3). The RPP13 gene in *A. thaliana* controls resistance to the oomycete pathogen, *Hyaloperenospora parasitica.*

As already described, a functional fragment or a functional homologue thereof of Rpi-blb3 is a fragment or homologue that is capable of providing at least partial resistance or increasing resistance in a plant of the Solanaceae family against an oomycte infection.

Means to test the functionality of a functional fragment or a functional homologue of Rpi-blb3 have been provided above. With these assays the inventors, e.g. through allele mining, found additional functional homologues. These homologues are denominated as Rpi-abpt, R2-like and R2 (see FIG. 6). The functionality test reported in Table 5 shows that transgenes for these genes are resistant to *P. infestans*. However, it also appears that slight differences in the spectrum of resistance are discernable between these homologues, especially with respect to *P. infestans* isolates 99190, 99183 and 99189.

Based on the herein described nucleic acid sequences, the invention also provides probes and primers (i.e. oligonucleotide sequences complementary to one of the (complementary) DNA strands as described herein). Probes are for example useful in Southern or Northern analysis and primers are for example useful in PCR analysis. Primers based on the herein described nucleic acid sequences are very useful to assist plant breeders (active in the field of classical breeding and/or breeding by genetic modification of the nucleic acid content of a plant (preferably said plant is a *Solanum tuberosum* or *Solanum lycopersicum*, formerly known as *Lycopersicon esculentum*), in selecting a plant that is capable of expressing Rpi-blb3.

Hence, in a further embodiment, the invention provides a binding molecule capable of binding to a nucleic acid as described herein or its complementary nucleic acid. In a preferred embodiment, said binding molecule is a primer or a probe. As mentioned, such a binding molecule is very useful for plant breeders and hence the invention further provides a method for selecting a plant or plant material or progeny thereof for its susceptibility or resistance to an oomycete infection said method comprising the steps of testing at least part of said plant or plant material or progeny thereof for the presence or absence of a nucleic acid as described herein, e.g. a nucleic acid encoding Rpi-blb3. In a preferred embodiment, said method further comprises providing a binding molecule as described herein, such as a primer or a probe. In yet another preferred embodiment, the nucleic acid of a to be tested plant is isolated from said plant and the obtained isolated nucleic acid is brought in contact with one or multiple (preferably different) binding molecule(s). One can for example use a PCR analysis to test plants for the presence of absence of Rpi-blb3 in the plant genome.

The herein described Rpi-blb3 protein can also be used to elicit antibodies by means known to the skilled person. The invention thus also provides an antibody that (specifically) binds to the protein encoded by the herein described isolated or recombinant nucleic acid (for example the nucleic acid sequence of FIG. 8 and especially the nucleotides 2944-5487) or an antibody that (specifically) binds to a protein as depicted in FIG. 6 or a functional fragment or a functional homologue thereof. Such an antibody is for example useful in protein analysis methods such as Western blotting or ELISA.

Based on the herein provided nucleic acid sequences, the invention also provides the means to introduce or increase resistance against an oomycete infection in a plant. The invention therefore also provides a method for providing at least partial resistance or increasing resistance in a plant against an oomycete infection comprising providing a plant or a part thereof with:

an isolated or recombinant nucleic acid sequence comprising a nucleic acid sequence encoding the Rpi-blb3 amino acid sequence of FIG. 6 or a functional fragment or a functional homologue thereof, or an isolated or recombinant nucleic acid sequence as depicted in FIG. 8, or a vector comprising the herein described nucleic acid sequences, or a host cell as described herein.

Such a method for providing at least partial resistance or increasing resistance in a plant against an oomycete infection involves the transfer of DNA into a plant, i.e., involves a method for transforming a plant cell comprising providing said plant cell with a nucleic acid as described herein or a vector as described herein or a host cell as described herein.

There are multiple ways in which a recombinant nucleic acid can be transferred to a plant cell, for example *Agrobacterium* mediated transformation. However, besides by *Agrobacterium* infection, there are other means to effectively deliver of DNA to recipient plant cells when one wishes to practice the invention. Suitable methods for delivering DNA to plant cells are believed to include virtually any method by which DNA can be introduced into a cell, such as by direct delivery of DNA such as by PEG-mediated transformation of protoplasts, by desiccation/inhibition-mediated DNA uptake (Potrykus et al., Mol. Gen. Genet., 199:183-188, 1985), by electroporation (U.S. Pat. No. 5,384,253), by agitation with silicon carbide fibers (Kaeppler et al., 1990; U.S. Pat. No. 5,302,523; and U.S. Pat. No. 5,464,765), and by acceleration of DNA coated particles (U.S. Pat. No. 5,550,318; U.S. Pat. No. 5,538,877; and U.S. Pat. No. 5,538,880). Through the application of techniques such as these, cells from virtually any plant species may be stably transformed, and these cells developed into transgenic plants.

In case *Agrobacterium* mediated transfer is used, it is preferred to use a substantially virulent *Agrobacterium* such as *A. tumefaciens*, as exemplified by strain A281 or a strain derived thereof or another virulent strain available in the art. These *Agrobacterium* strains carry a DNA region originating from the virulence region of the Ti plasmid pTiBo542 containing the virB, virC and virG genes. The virulence (vir) gene products of *A. tumefaciens* coordinate the processing of the T-DNA and its transfer into plant cells. Vir gene expression is controlled by virA and virG, whereby virA upon perception of an inducing signal activates virG by phosphorylation. VirG, in turn, induces the expression of virB,C,D,E. These genes code for proteins involved in the transfer of DNA. The enhanced virulence of pTiBo542 is thought to be caused by a hypervirulent virG gene on this Ti plasmid (Chen et al. Mol. Gen. Genet 230; 302-309, 1991).

After transfer of a nucleic acid into a plant or plant cell, it must be determined which plants or plant cells have been provided with said nucleic acid. This is for example accomplished by using a selectable marker or a reporter gene. Among the selective markers or selection genes that are most widely used in plant transformation are the bacterial neomycin phosphotransferase genes (nptI, nptII and nptIII genes) conferring resistance to the selective agent kanamycin, suggested in EP131623 and the bacterial aphIV gene suggested in EP186425 conferring resistance to hygromycin. EP 275957 discloses the use of an acetyl transferase gene from *Streptomyces viridochromogenes* that confers resistance to the herbicide phosphinotricin. Plant genes conferring relative resistance to the herbicide glyphosate are suggested in EP218571. The resistance is based on the expression of a gene encoding 5-enolshikimate-3-phosphate synthase (EPSPS) that is relatively tolerant to N-phosphomethylglycine. Certain amino acids such as lysine, threonine, or the lysine derivative amino ethyl cysteine (AEC) and tryptophan analogs like 5-methyl tryptophan can also be used as selective agents due to their ability to inhibit cell growth when applied at high concentration. In this selection system expression of the selectable marker gene results in overproduction of amino acids by transgenic cells which permits the transgenic to grow under selection. Suitable examples of reporter genes are beta-glucuronidase (GUS), beta-galactosidase, luciferase and green fluorescent protein (GFP).

In a preferred embodiment, the invention provides a method for providing at least partial resistance or increasing resistance in a plant against an oomycete infection comprising providing a plant or a part thereof with:

an isolated or recombinant nucleic acid sequence comprising a nucleic acid sequence encoding the Rpi-blb3 amino acid sequence of FIG. 6 or a functional fragment or a functional homologue thereof, or an isolated or recombinant nucleic acid sequence as depicted in FIG. 8, or a vector comprising the herein described nucleic acid sequences, or a host cell as described herein, wherein said oomycte comprises *Phytophthora*, preferably *Phytophthora infestans* and/or wherein said plant comprises a plant from the Solanaceae family, preferably a potato or tomato plant.

The invention also provides a plant that is obtainable by using a method for providing at least partial resistance or increasing resistance in a plant against an oomycete infection as described above. A preferred plant is a plant from the Solanaceae family and even more preferred said plant is a *Solanum tuberosum* or a *Solanum lycopersicum*, formerly known as *Lycopersicon esculentum*. The invention thus also provides a plant that has been provided with a nucleic acid encoding a Rpi-blb3 protein or a functional fragment or a functional homologue thereof. Whether a plant has been provided with a nucleic acid as described herein is for example determined by using a probe or primer that has been designed based on the herein described nucleic acid sequence. One can also use an antibody that (specifically) binds to encoded Rpi-blb3 protein.

The invention further provides a leaf, tuber, fruit or seed or part or progeny of a genetically modified plant comprising a nucleic acid encoding the Rpi-blb3 amino acid sequence of FIG. 6 or a functional fragment or a functional homologue thereof.

In a preferred embodiment, the herein described nucleic acid is transferred to a potato variety other than *Solanum bulbocastanum*, the herein described nucleic acid is preferably transferred to a non-bulbocastanum background, preferably to a commercial interesting variety such as Bintje, Desiree or Premiere, Spunta, Nicola, Favorit, Russet Burbank, Aveka or Lady Rosetta.

In yet another preferred embodiment, the herein described nucleic acid is foreign to the host cell. The term "foreign" is herein used to describe the situation in which the herein described nucleic acid is heterologous with respect to the host cell (i.e. derived from a cell or organism with a different genomic background) or the herein described nucleic acid is homologous with respect to the used host cell but located in a different genomic environment than the naturally occurring counterpart of said nucleic acid (for example not on the natural locus or located between different genes).

In yet another embodiment, the invention provides a method for providing at least partial resistance or increasing resistance in a plant against an oomycete infection comprising providing a plant or a part thereof with:

an isolated or recombinant nucleic acid sequence comprising a nucleic acid sequence encoding the Rpi-blb3 amino acid sequence of FIG. 6 or a functional fragment or a functional homologue thereof, or an isolated or recombinant nucleic acid sequence as depicted in FIG. 8, or a vector comprising the herein described nucleic acid sequences, or a host cell as described herein, wherein said plant before being provided with a nucleic acid encoding Rpi-blb3 or a functional part or a functional homologue thereof is at least partly susceptible to an oomycete infection (for example *P. infestans*). The fact that a plant is partly susceptible/partly resistant to an oomycete infection can be the result of genes naturally present in said plant, but it may also be the result of already introduced (other) resistance genes.

The invention further provides use of an isolated or recombinant nucleic acid sequence comprising a nucleic acid sequence encoding the Rpi-blb3 amino acid sequence of FIG. 6 or a functional fragment or a functional homologue thereof or use of an isolated or recombinant nucleic acid sequence as depicted in FIG. 8 or use of a vector comprising any of said nucleic acid sequences or use of a host cell comprising any of said nucleic acid sequences or said vector for providing a plant with at least partial resistance against an oomycete infection. In a preferred embodiment, said oomycte comprises *Phytophthora* and even more preferably *Phytophthora infestans*. In yet another preferred embodiment said plant comprises *Solanum tuberosum* or *Solanum lycopersicum*, formerly known as *Lycopersicon esculentum*.

In yet another embodiment, the invention provides a method for producing Rpi-blb3 protein or a functional fragment or a functional homologue thereof comprising functionally linking a nucleic acid as described herein to a regulatory sequence and allowing said nucleic acid to be expressed in a host cell. Examples of a regulatory sequence are a promoter and/or terminator sequence.

The invention further provides the promoter and/or terminator sequences of Rpi-blb3 (see FIG. 8). FIG. 8 shows the nucleotide sequence of clone Blb25-B2 (8461 bp) containing the Rpi-blb3 gene and regulatory sequences. The Rpi-blb3 coding region of 2544 bp is highlighted in lower case (2944-5487). The upstream 2732 nt (211-2942) and the downstream 882 nt (5488-6370) harbour the regulatory sequences that ensure correct expression of the gene. The skilled person is very well capable of cloning (part of) said regulatory sequences and testing their efficiency in transcription.

The invention will be explained in more detail in the following, non-limiting examples.

EXAMPLE 1

Results

Here we describe the cloning and functional characterization of Rpi-blb3, Rpi-abpt, R2-like and R2 from the major late blight resistance locus on chromosome 4 of potato (Park et al 2005a, 2005b, 2005c; Li et al. 1998)

Cloning of Rpi-blb3 and Rpi-abpt

In order to clone Rpi-blb3 and Rpi-abpt, two BAC libraries were constructed using DNA derived from the resistant clones Blb99-256-3 and 707TG11-1, respectively. Approximately 74000 clones with an average insert size of 85 kb, corresponding to 8 genome equivalents, were obtained for each library. These libraries were screened initially with SCAR marker Th21 (Table 2), which cosegregated with resistance in mapping populations of 1396 and 1383 F1 progeny plants, respectively (Park et al. 2005). In this way BAC clones Blb22 and TG9 were identified, respectively (FIG. 1). By sequencing the ends of these two BACs, new markers (Table 2) were developed which were used to define the genetic intervals of the R loci more precisely and to re-screen the BAC libraries to identify clones that overlapped with the initial BAC clones. In this way the Rpi-blb3 locus was delimited to a 0.3 cM (Blb22S-Blb25T; 4/1396 recombinants) interval that is physically spanned by the two partially overlapping BAC clones Blb22 and Blb25 (FIG. 1A). In case of the Rpi-abpt locus, the partially overlapping BAC clones TG9 and TG77 were identified. One end of the contig cosegregated with resistance (TG77S) while the other mapped 0.1 cM proximal to Rpi-abpt (TG9S) (FIG. 1B).

To gain insight into the molecular structure of the R loci under study, BAC clones Blb22 and TG9 were sequenced to 6× coverage. This revealed that clone Blb22 did not contain any R gene homologues (RGH) whereas clone TG9 contained two RGH, which shared significant homology to RGHs present in the sequenced tomato BAC clone AF411807L (van der Hoeven et al. 2002). BAC clones Blb25 and TG77 were subsequently screened for the presence of RGH specific sequences through PCR analysis using the primers 4-PLOOP-F and 4-GLPL-R (Table 2) which were designed by aligning the RGH sequences of clone AF411807L with those present on BAC clone TG9. Southern analysis of BAC clones Blb22, Blb25, TG9 and TG77 using an RGH specific PCR fragment amplified from BAC clone Blb25 as a probe, identified a minimum of two RGHs on BAC Blb25 and TG9 and one RGH on TG77 (FIG. 1).

Figure 2:
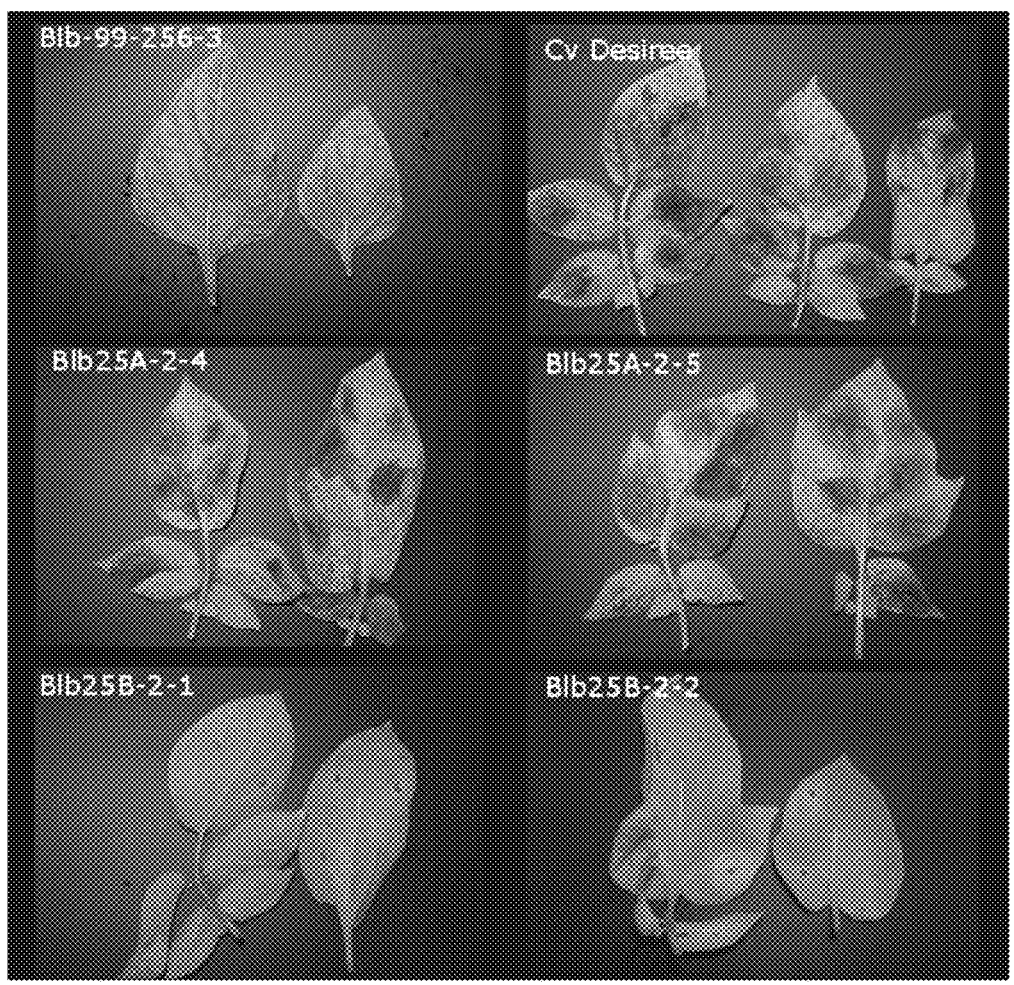
FIG. 2. Genetic complementation for late blight susceptibility. Typical disease phenotype 8 days after inoculation with a sporangiospore suspension of *Phytophthora infestans* isolates 90128. Blb-99-256-3: resistant parental clone; cv. Desiree: potato cultivar used for transformation; Blb25A-2-4 and Blb25A-2-5: primary transformants harboring RGH-Blb25A; Blb25B-2-1 and Blb25B-2-2: primary transformants harboring RGH-Blb25B (Rpi-blb3).

Libraries harboring random overlapping binary subclones of 8-10 kb were therefore generated from BAC clones Blb25 and TG9. A total of 1152 clones per library were screened for the presence of RGHs using primers GLO2-F and -R (Table 2). Based on restriction analyses of the PCR fragments, RGH positive subclones were divided into separate classes, Blb3GH-A and Blb3GH-B for Rpi-blb3, AbptGH-A and AbptGH-B for Rpi-abpt. After determining the relative positions of the RGHs within the 8-13 kb subclones, candidates from each class were targeted for transformation to the susceptible potato cultivar Desiree. Transformation experiments carried out with subclones Blb25-A3, Blb25-B2, TG9-A1 and TG9-B2 harboring candidates Blb3GH-A, Blb3GH-B, AbptGH-A and AbptGH-B, respectively, resulted in numerous primary transformants. Detached leaf assays using isolates IPO-0 and 90128 revealed that all of the plants transformed with Blb25-A3, TG9-A1 and TG9-B2 were susceptible to both isolates but that the majority (7/8) of the tested transgenic plants harboring Blb25-B2 reacted to both isolates with a hypersensitive response (HR) (FIG. 2). In view of the differential response between the primary transformants harboring Blb3GH-A and Blb3GH-B, we designated Blb3GH-B as the Rpi-blb3 gene.

Figure 1B:
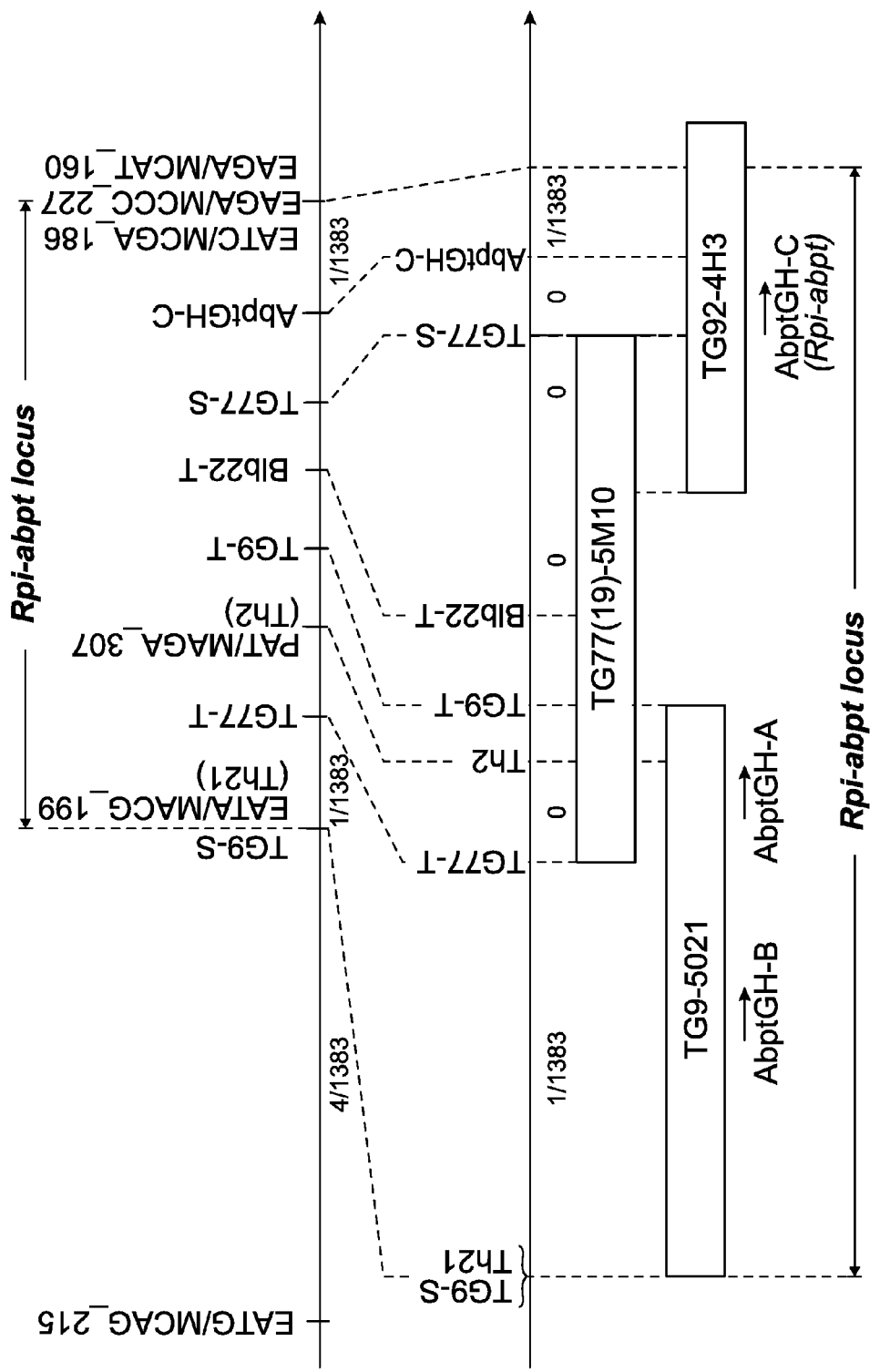
Figure 3:
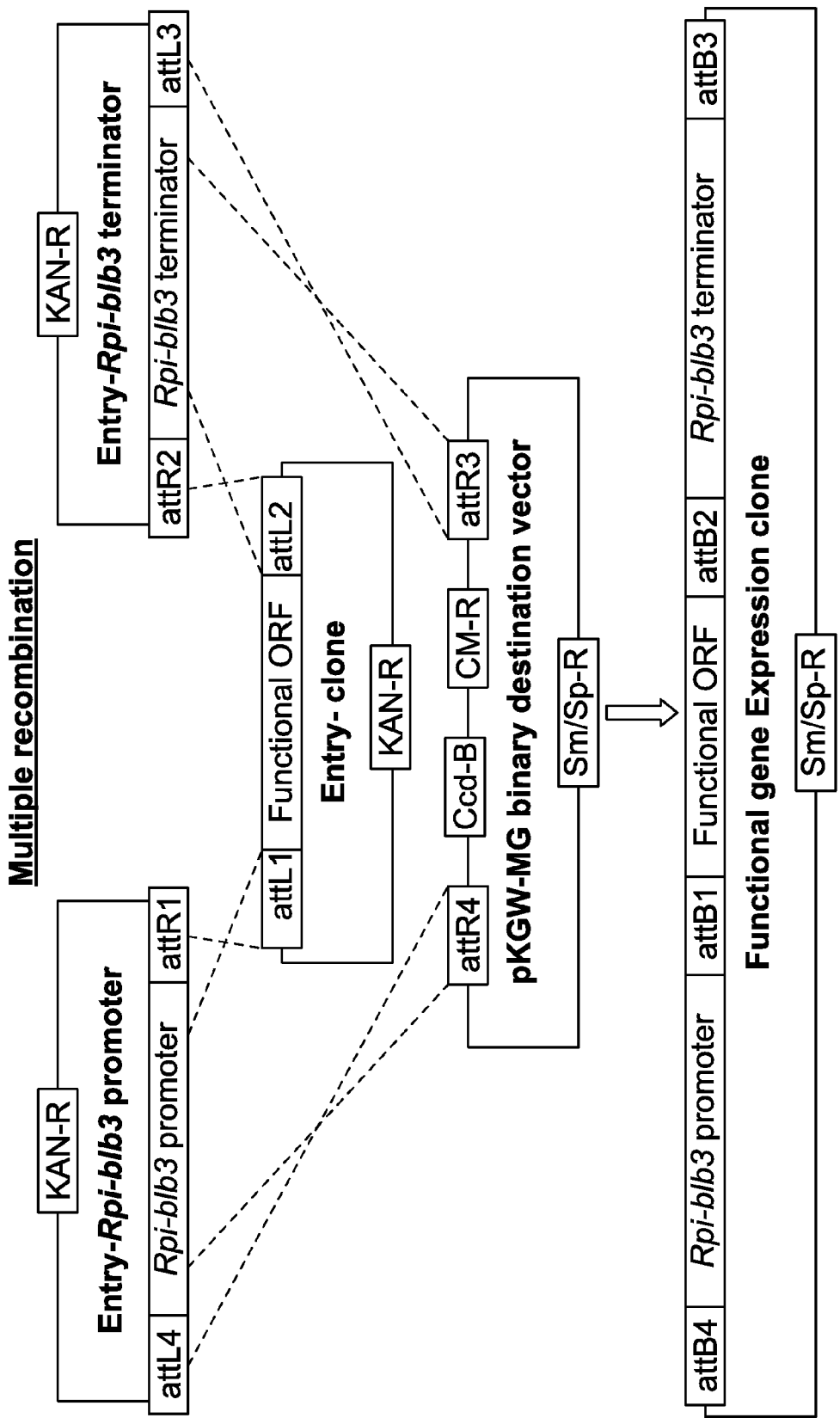
FIG. 3. Gateway strategy used to clone Rpi-abpt, R2 and R2-like. LR recombination of the three entry clones bearing the DNA fragments Rpi-blb3 promoter, candidate gene, and Rpi-blb3 terminator, with the Multisite Gateway destination binary vector pKGW-MG, leading to the functional gene expression clone.

In order to identify additional candidate genes for Rpi-abpt, the Rpi-abpt specific BAC library was screened with TG77S, leading to the identification of the TG77 overlapping BAC clone TG92 (FIG. 1B). Screening of this BAC clone with different sets of primers designed to amplify AbptGH-A, AbptGH-B, Blb3GH-A or Rpi-blb3, resulted in the identification of a third Rpi-abpt candidate gene, AbptGH-C (FIG. 1B), which, when converted into a specific marker (AbptGH-C; Table 2 and FIG. 1B), also cosegregated with resistance. Southern blot analysis using the AbptGH-C amplicon as a probe revealed that clone TG92 contained only a single RGH. Primers designed on the start and stop codon of Rpi-blb3 (Blb3-start and Blb3-end, Table 2) were subsequently used to amplify a full-length AbptGH-C amplicon from clone TG92, which was cloned into the Gateway® entry vector pDONR221. Using Multisite Gateway® technology, the AbptGH-C amplicon was subsequently cloned into the binary pKGW-MG destination vector between Rpi-blb3 derived promoter and terminator sequences of 2723 nt and 883 nt, which were cloned into pDONR™ P4-P1R and pDONR™ P2R-P3 (FIG. 3).

Figure 4:
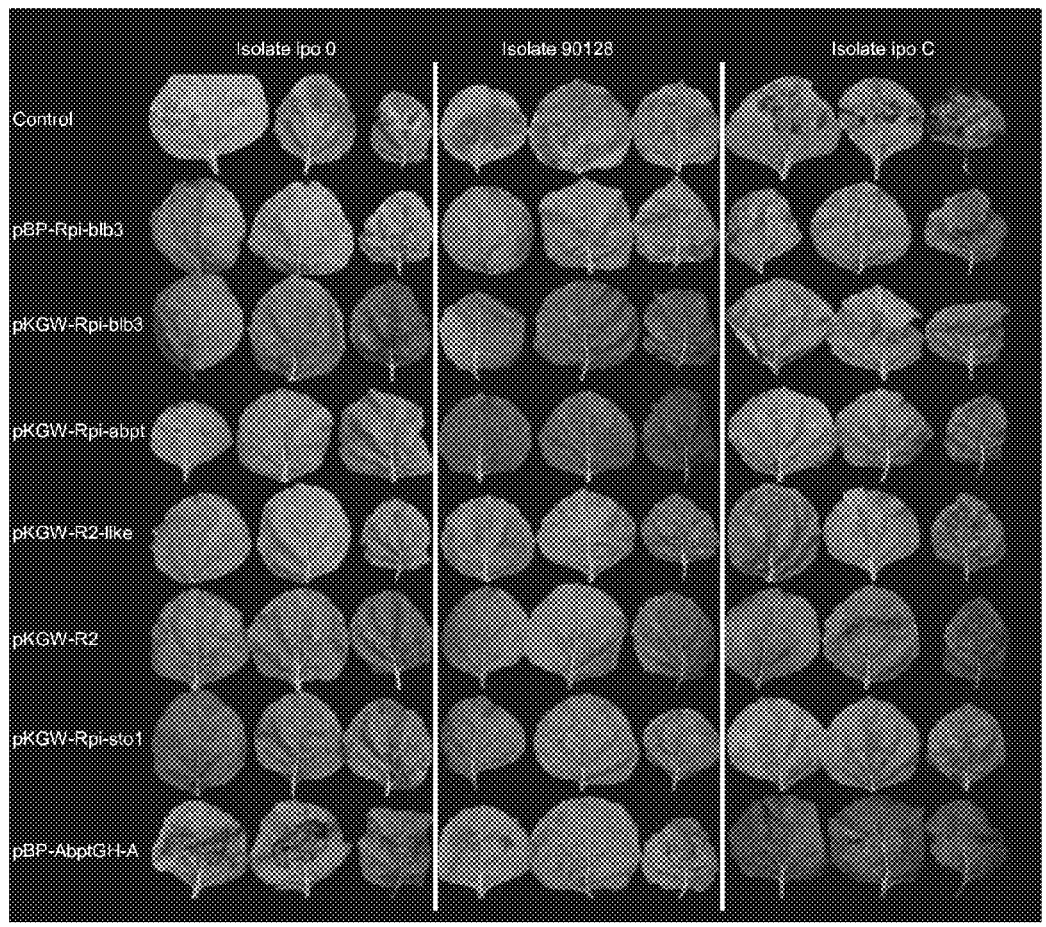
FIG. 4. Transient complementation in *Nicotiana benthamiana* leaves. Typical disease phenotypes 7 days after inoculation with a sporangiospore suspension of *P. infestans* isolates IPO-0 (avirulent), 90128 (avirulent) and IPO-C (virulent on all except Rpi-sto). Control: wt *N. benthamiana*; pBP-Rpi-blb3: genomic Rpi-blb3 gene construct; pKGW-Rpi-blb3, -abpt, -R2-like, -R2, Rpi-sto1: multisite Gateway gene constructs in which gene expression is regulated by the Rpi-blb3 promoter and terminator sequences.

Complementation analysis was carried out in *Nicotiana benthamiana* using the *Agrobacterium tumefaciens* transient assay (ATTA) whereby 4-week old wildtype *N. benthamiana* plants were infiltrated with the *Agrobacterium* strain COR308 containing pKGW-AbptGH-C. The binary clones pBP-Rpi-blb3 and pKGW-Rpi-blb3, comprising the original genomic Rpi-blb3 gene construct and a Multisite Gateway® reconstituted Rpi-blb3 gene construct, respectively, were used as positive controls, and pBP-AbptGH-A as a negative control. Infiltrated leaves were challenged after two days with *P. infestans* strain PY23 or IPO-complex in detached leaf assays (DLA). Leaves infiltrated with pKGW-AbptGH-C, pBP-Rpi-blb3 and pKGW-Rpi-blb3 developed HRs at the inoculation sites whereas wildtype leaves and those infiltrated with pBP-AbptGH-A were susceptible to isolate PY23. As expected, all leaves inoculated with IPO-C were susceptible (FIG. 4). In view of these results, AbptGH-C was designated Rpi-abpt.

Cloning of R2 and R2-Like Through Blb3GH Allele Mining

Figure 5:
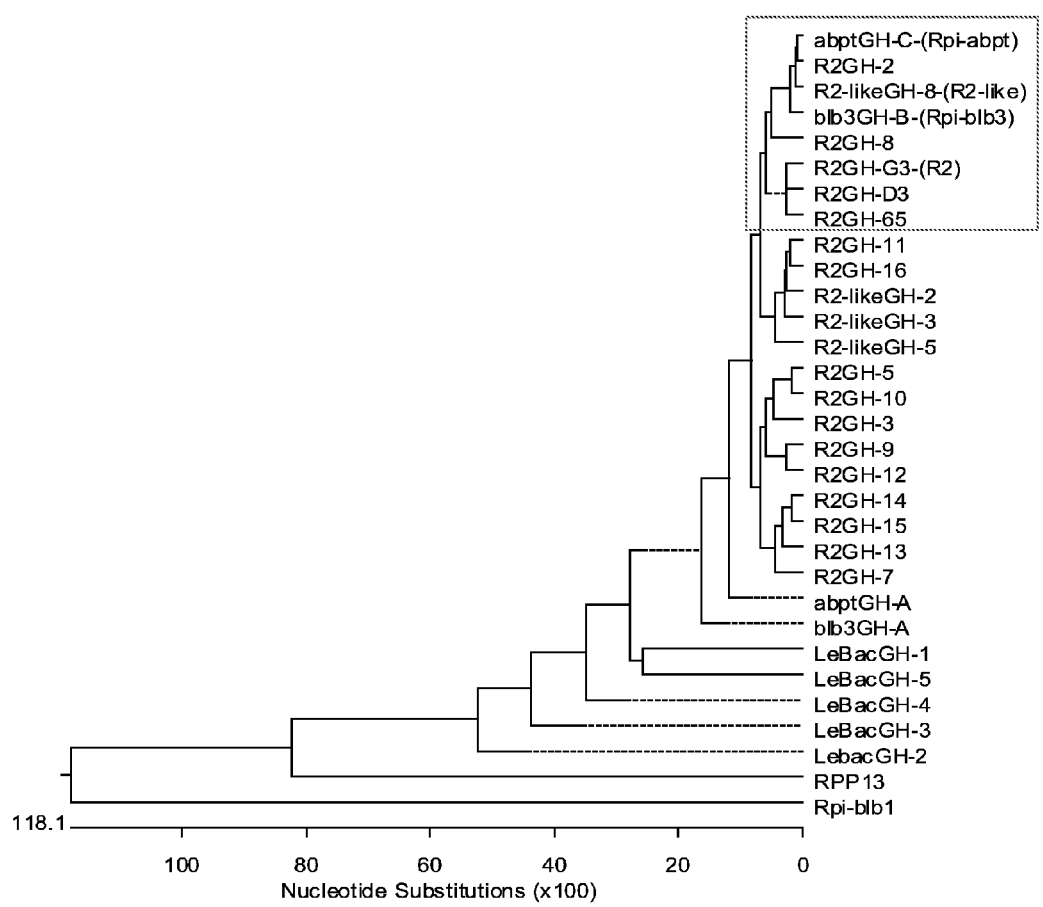

Rpi-blb3 and Rpi-abpt belong to the major late blight (MLB) resistance locus on chromosome 4 that also harbors R2 and R2-like (Li et al., 1998; Park et al., 2005c). In view of the conserved marker order and observed allelic conservation between the genetic maps of Rpi-blb3, Rpi-abpt, R2, and R2-like (Park et al., 2005c), and the high sequence conservation between Rpi-blb3 and Rpi-abpt, we set out to clone R2 and R2-like through an Rpi-blb3 allele mining strategy. The same primers used to amplify the Rpi-abpt candidate gene from BAC clone TG92 were used to amplify full-length Blb3GH from the resistant parental genotypes BET95-4200-3 (MaR2) and AM3778-16, harboring R2 and R2-like, respectively. Amplicons of the expected size were cloned into pDONR221 and fully sequenced. In total, eight unique sequences were obtained from AM3778-16 (R2-likeGH) and nineteen from BET95-4200-3 (R2GH), with amino acid identities between Rpi-blb3 and the novel Blb3GH ranging from 86.4% to 97.3% for R2-likeGH and 83.8% to 94.2% for R2GH (Table 3). Phylogenetic analysis of all the available amino acid sequences clustered one R2like-GH and five R2GH in a clade together with the functional genes Rpi-blb3 and Rpi-abpt (FIG. 5). The amino acid sequence of R2-likeGH-8 shares 97.3% amino acid identity with Rpi-blb3. R2GH-2, R2GH-8, R2GH-G3, R2GH-D3 and R2GH-65 share 94.2, 91, 92.6, 89.7, and 92.8% amino acid identity with Rpi-blb3, respectively (Table 3). This set of candidate genes was targeted for functional analysis and therefore cloned into the binary vector pKGW-MG between the Rpi-blb3 promoter and terminator sequences, as described above for the Rpi-abpt gene.

Transient complementation assays in *N. benthamiana* showed R2GH-G3 and R2-likeRGH-8 to confer resistance to the appropriate races, whereas R2GH-2, R2GH-8, R2GH-D3 and R2GH-65 were non-functional (FIG. 4). R2GH-G3 and R2-likeGH-8 were therefore designated as R2 and R2-like, respectively.

Gene Structure and Functionality

Rpi-blb3, Rpi-abpt, R2 and R2-like encode ORFs of 2538-2544 nucleotides (nt) that code for proteins of 845-847 amino acids harboring all the signature sequences characteristic of LZ-NBS-LRR R-proteins (FIG. 6). Interestingly, with respect to known functional R-proteins, Rpi-blb3, Rpi-abpt, R2, and R2-like share the highest homology (34.9% aa identity) with RPP13 from *Arabidopsis thaliana* (Bittner-Eddy et al., 2000), which confers resistance to *Hyaloperonospora parasitica*. The highest homology with RPP13 resides in the NBS domain with 49.3% sequence identity, and the lowest within the LRR domains (34.3%). The LRR domains of Rpi-blb3, Rpi-abpt, R2, and R2-like are highly homologous and comprise 14 imperfect repeats (FIG. 6). The LZ and NBS domains are more polymorphic, those of R2 being the most divergent. Rpi-abpt and R2-like are identical except for the sequence between LRR2 and LRR3, where Rpi-abpt contains a stretch of amino acids that is identical to that of R2. The LRR domain of R2 is identical to that of Rpi-abpt, except for amino acid residue 774 (FIG. 6).

Figures 2, 7:
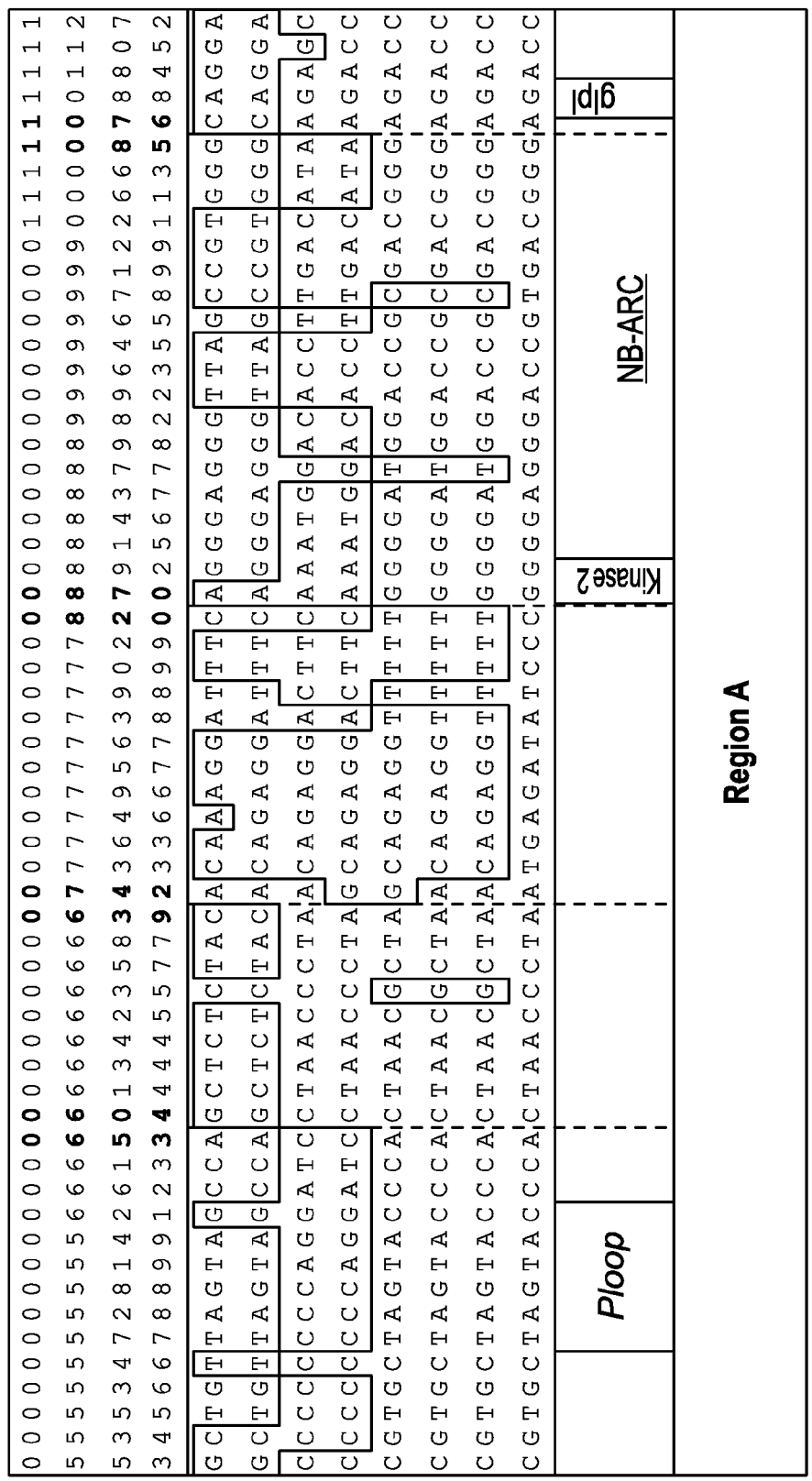
FIG. 7. Sequence affiliation analysis between Rpi-blb3 gene homologues. Depicted are only informative polymorphic sites (IPS) of the nucleotide sequences of 7 Rpi-blb3 homologs, including Rpi-blb3, Rpi-abpt, R2 and R2-like. The vertical number at the top of each column indicates the corresponding nucleotide position in the full consensus sequence. Highlighted are the IPS that are different from the Rpi-blb3 sequence. Indicated at the bottom is the domain from which each IPS is from (LZ, NBS or LRR) and also relative positions of four putative recombination blocks (region A-D)
Figures 3, 7:
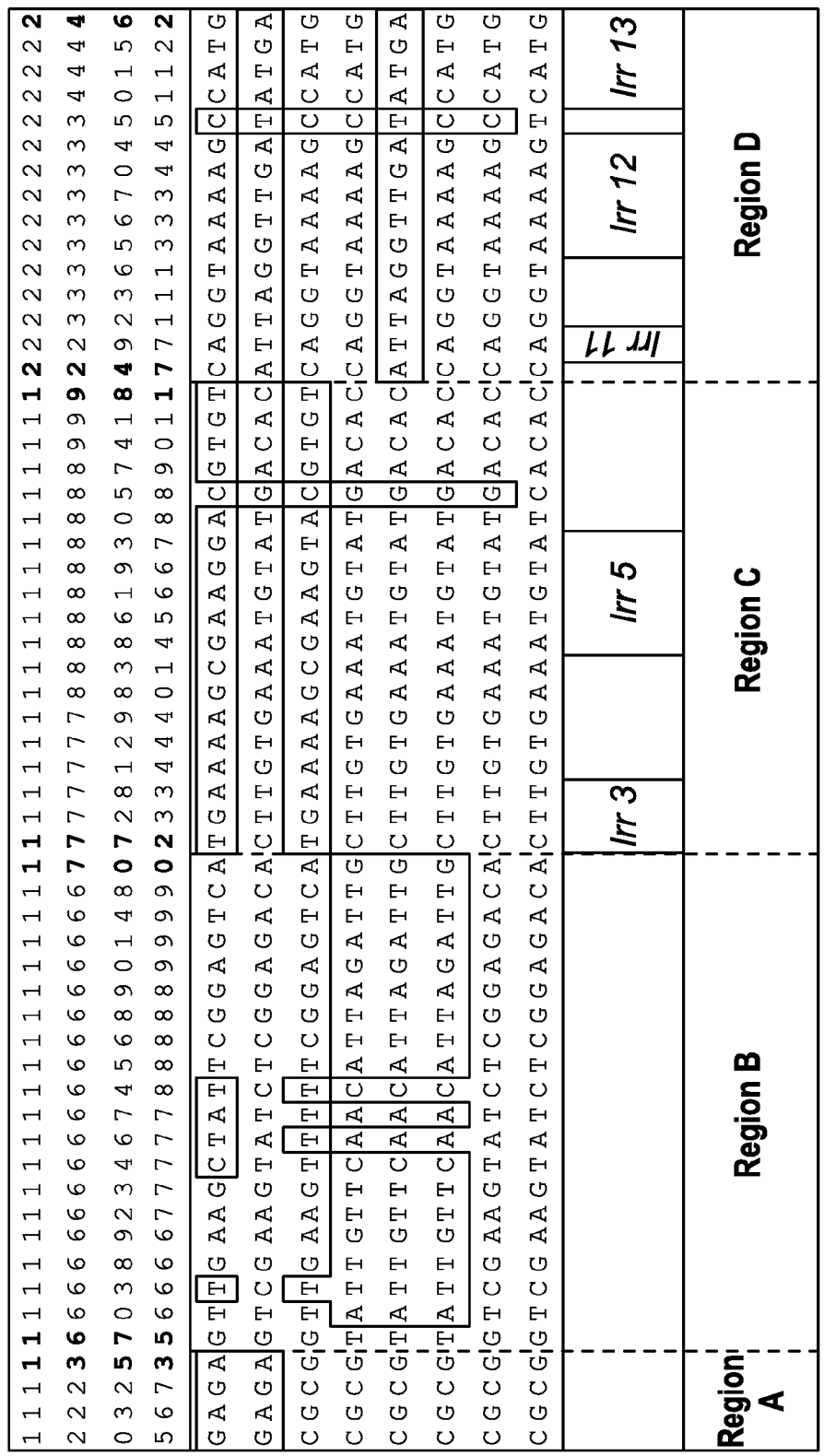

Alignment of the nucleotide sequences of the four functional genes and those of four additional Blb3GHs and subsequent analysis of informative polymorphic sites (IPS), i.e. sites where two or more genes carry the same nucleotide (Parniske et al., 1997), reveals clear blocks of sequence affiliation between different members of the gene family (FIG. 7), indicating that sequence exchange events between Blb3RGs have been involved in the evolution of the gene family (FIG. 7). Interestingly, the observed sequence affiliations in the 5'-terminal half of the genes extend throughout the LZ and NBS domains whereas sequence affiliations in the LRR domain suggest exchange of specific combinations of LRRs, underlining the modular nature of R-proteins.

In an attempt to assess the biological relevance of the observed sequence exchange events in relation to resistance spectrum, the parental clones harboring Rpi-blb3 (Blb99-256-3), Rpi-abpt (707TG11), R2 (BET95-4200-3(MaR2)) and R2-like (AM-3778-16) were challenged in detached leaf assays with 17 different P. infestans isolates (Table 4 and 5). For 14 isolates all four clones displayed the same specificity. However, differential interactions were observed with three isolates (Table 5). Isolates 99190 and 99189 are virulent on Blb99-256-3, AM-3778-16 and BET95-4200-3(MaR2) but avirulent on 707TG11-1. Moreover, isolate 99183 is virulent on BET95-4200-3(MaR2) and 707TG11, but avirulent on AM-3778-16 and Blb99-256-3. These data suggest that the four genes under study reflect three recognition specificities whereby Rpi-blb3 and R2-like share the same resistance spectrum. When taking in to account the observed sequence affiliations between Rpi-blb3, R2-like and Rpi-abpt, it is tempting to speculate that the polymorphic sequence between LRR2 and LRR3 could explain both the equivalent functionality of Rpi-blb3 and R2-like and the difference in resistance spectrum between R2-like and Rpi-abpt. Alternatively, the differential resistance spectra of the four clones may reflect the presence of additional R-genes.

Comparison of the amino acid sequences of the four functional genes with that of the non-functional sequence of R2GH-2, reveals that the majority of the R2GH-2 specific amino acids are concentrated in the putative solvent exposed residues of LRR11-LRR13 (FIG. 6), which reside within the 3'-most recombination block of the LRR domain (FIG. 7), suggesting that these LRRs play an important role in determining R2 specificity. However, presence of the R2 specific solvent exposed residues is not sufficient for R2 specificity as is illustrated by the non-functional homolog R2GH-D3, which contains the R2 specific LRR11-LRR13 sequence but differs from the four functional genes in the region harbouring LRR3-LRR10, which reside in the central recombination block of the LRR domain (FIG. 7). The latter observation illustrates the crucial role that putative intra-molecular interactions within the LRR domain and possibly between the LRR domain and the LZ or NBS domain play in determining functionality of the functional Blb3GHs.

MATERIALS AND METHODS

Plant Material and *Phytophthora Infestans* Isolates

In this study we used the four late blight resistant clones Blb99-256-3, 707TG11-1, AM3778-16 and BET95-4200-3, harbouring Rpi-blb3, Rpi-abpt, R2-like, and R2, respectively. The potato cultivar Desiree was used for transformation. Wildtype *Nicotiana benthamiana* plants were used for transient complementation assays.

Characteristics and origin of *P. infestans* isolates used in this study are indicated in Table 4.

BAC Library Construction

Clones Blb99-256-3 and 707TG11-1 were used as DNA sources for the construction of BAC libraries. High-molecular weight DNA preparation and BAC library construction were carried out as described by Rouppe van der Voort et al. (1999). Approximately 74000 clones with an average insert size of 85 kb, corresponding to 8 genome equivalents, were obtained per library. The BAC clones were stored as bacterial pools containing approximatively 700 to 1000 white colonies. These were generated by scraping the colonies from the agar plates into LB medium containing 18% glycerol and 12.5 µg ml$^{-1}$ chloramphenicol using a sterile glass spreader. These so-called super pools were stored at −80° C. Marker screening of the BAC libraries was done, first by isolating plasmid DNA from each pool using the standard alkaline lysis protocol and PCR was carried out to identify positive pools. Bacteria corresponding to positive pools were diluted and plated on LB agar plate containing chloramphenicol (12.5 µg ml$^{-1}$). Individual white colonies were picked into 384-well microtitre plates and single positive BAC clones were subsequently identified by marker screening as described by Rouppe van der Voort et al (1999). Names of BAC clones isolated from the super pools carry the prefix Blb (e.g. Blb25) or TG (e.g. TG9).

Subcloning of Candidate Genes

Candidate RGAs were subcloned from BAC clone BLB25 and TG9 as follows. Aliquots of approximatively 1 microgram BAC DNA were digested with 0.03 U of Sau3AI restriction enzyme for 10 min. The partially digested BAC DNA was subjected to electrophoresis at room temperature in 0.5×TAE using a linear increasing pulse time of 1-10 sec and a field strength of 90 V cm-1 for 6 h. After electrophoresis, the agarose gel was stained with ethidium bromide to locate the region of the gel containing DNA fragments of approximately 10 Kbp in size. This region was excised from the gel and treated with GELASE (Epicentre Technologies, USA) according to the manufacturer. The size-selected DNA was ligated to the BamH1-digested and dephosphorylated binary vector pBINPLUS (Van Engelen et al., 1995) followed by transformation to ElectroMAX *E. coli* DH10B competent cells (Life technologies, UK).

Transformation of Susceptible Potato Variety

Binary plasmids harbouring the candidate genes were transformed to *A. tumefaciens* strain COR308 (Hamilton et al., 1996). After verifying their stability in *Agrobacterium* these clones were transformed to the susceptible potato variety Desiree. Overnight cultures of the transformed *A. tumefaciens* strain were used to transform internodal cuttings from in vitro grown plants (Heilersig, H. J. B et al., 2006). A total of 200 explants were used for each transformation. Primary transformants were transferred to the greenhouse.

DNA Sequencing and Computer Analysis

BAC clone sequencing was carried on using a shotgun cloning strategy. Sequencing reactions were performed using a dye terminator cycle sequencing reaction kit (Perkin-Elmer, Pt Biosystem, Warrington, UK), M13 universal forward and reverse primers, and an ABI377 automated sequencer (Applied Biosystem, La Jolla, Calif., USA). Sequence contigs were assembled using the ATADEN sequence and analysis program (Dear and Staden, 1991).

The binary subclones were sequenced using a primer walking strategy (700 bp by 700 bp). Gene structure was predicted using FGENESH++(Softberry). Multiple sequence alignments were conducted using CLUSTALX 1.81 (Thompson et al., 1997). Search of homologous genes to Rpi-blb3 was carried using the Basic Local Alignment Search Tool (BLAST). Conserved domains were identified using Swiss-Prot (InterProScan, EMBL-EBI, ExPASy, SAPS).

Resistance Assay

Detached leaf assays were used to determine the resistance phenotypes of primary transformants and *N. benthamiana* leaves. For complementation analyses, primary transformants were tested with isolates IPO-0 and 90128 (FIG. 2). Inoculum preparation and inoculation were performed as described by Vleeshouwers and associates (1999). Six days after inoculation, plant phenotypes were determined. Leaves showing no symptoms or a localized necrosis at the point of inoculation were scored as resistant and those with clear sporulating lesions as susceptible.

Transient Complementation in N. Benthamiana

Agrobacterium transient transformation assays (ATTA) were carried out on N. benmthamiana. Recombinant A. tumefaciens cultures were grown in LB medium (10 gram bacteriological peptone, 10 gram NaCl and 5 gram yeast extract in 1 liter MQ water) supplemented with 5 mg/L Tetracycline and 50 mg/L Kanamycin for the COR308 constructs. After one or two days a calculated amount of culture (according to OD 0.5 at 600 nm) was transferred to YEB medium (5 gram beef extract, 5 gram bacteriological peptone, 5 gram sucrose, 1 gram yeast extract, 2 ml 1 M MgSO4 in 1 liter MQ water) supplemented with Kanamycin for all strains. After 1 day overnight cells were centrifuged at 3500 rpm and re-suspended in MMA medium (20 gram sucrose, 5 gram MS salts and 1.95 gram MES) supplemented with 1 ml 200 mM acetosyringone to a final OD of 0.2 and infiltrated into 4 weeks old plants with a 3 ml syringe. Infiltrated leaves were subsequently challenged after two days with P. infestans strains IPO-complex and PY23 in detached leaf assays (DLA). Hypersensitive response (HR) or P. infestans sporulation were scored from 4 to 8 days post inoculation.

Allele Mining

Primers of 32 nucleotides were designed on Rpi-blb3 sequence, with the forward primer beginning at the start codon (ATG) and the reverse primer beginning at the stop codon (TGA). BAC clone TG92-4-H3 containing Rpi-abpt and genomic DNA of the parental clones AM3778-16 and BET95-4200-3, containing R2-like and R2, respectively, were used as template in a long range PCR reaction (95 C: 2'40", 30×[94 C: 20", 56.8 C: 25", 64.3 C:7'], 64.3 C: 25') using the high fidelity DNA polymerase PfuTurbo® (Stratagene). PCR products were separated on agarose gel and purified using the QIAquick Gel Extraction Kit from Qiagen. The purified pool of Blb3 GHs were used in a BP reaction together with the donor plasmid pDONR 221 according to the protocol described by Untergasser et al. (located on the World Wide Web at untergasser.de/lab/protocols/bp_gateway_reaction_ii_v1_0.shtml). BP reaction products were transferred into DH10B E. coli competent cells, and subsequently plated on LB-agar plates containing the appropriate antibiotic. Transformed colonies were cultured o/n in LB liquid containing the appropriate antibiotic and plasmid DNA was isolated using a standard mini-prep protocol adapted from Sambrook et al ($2^{nd}$ edition) using the P1, P2, P3 solutions from Qiagen. Clones harboring candidate Blb3 GHs were cloned into the binary expression vector pKGW-MG, between Rpi-blb3 regulatory elements via a multiple LR reaction, using a pDONR-P4P1R plasmid harboring the Rpi-blb3 promotor, a pDONR-P2RP3 plasmid harboring the Rpi-blb3 terminator, and the pDONR221 plasmids harboring the candidate genes of interest. pKGW-MG plasmids harboring the genes of interest were then transferred to E. coli, and subsequently into an appropriate Agrobacterium tumefaciens strain, e.g. COR308 or AGL1, after the integrity of the constructs was checked by restriction analysis.

Tables

TABLE 1

R-genes and quantitative trait loci for late blight resistance reported for wild Solanum species

| Wild species | Locus type or name | Chromosome |
|---|---|---|
| S. berthaultii | QTLs (4) | I, III, VII and XI |
|  | Rpi-ber1 | X |
|  | Rpi-ber2 | VII |
| S. bulbocastanum | RB/Rpi-blb1 | VIII |
|  | Rpi-blb2 | VI |
|  | Rpi-blb3 | IV |
| S. caripense | QTL (2) | unassigned |
| S. demissum | R1 | V |
|  | R2 | IV |
|  | R3, R6, R7 | XI |
|  | R3a | XI |
|  | R3b | XI |
|  | R5-R11 | XI |
|  | R10, R11 | XI |
| S. microdontum | QTLs (3) | IV, V and X |
|  | QTL | Unassigned |
| S. mochiquense | Rpi-mcq1 (Rpi-moc1) | IX |
| S. paucissectum | QTLs (3) | X, XI and XII |
| S. phureja | Rpi-phu1 | IX |
| S. pinnatisectum | Rpi-pnt1 (Rpi1) | VII |
| S. vernei | QTLs (several) | VI, VIII, IX |
| Hybrids with | Rpi-abpt | IV |
| S. tuberosum | R2-like | IV |
|  | QTLs (several) | several |
|  | QTLs | IV |

TABLE 2

Overview of markers and primers used for mapping and cloning

| Marker | Type | PCR primer (5' to 3') | SEQ ID NO. | Tma | Enzymeb |
|---|---|---|---|---|---|
| Th21 | SCAR | F: ATTCAAAATTCTAGTTCCGCC | 1 |  | a.s. |
|  |  | R: AACGGCAAAAAGCACCAC | 2 |  |  |
| Blb22-S | CAPS | F: GTTTGATGTATGTTTGTTCTTGC | 3 | 56 | Msp1 |
|  |  | R: TAATGCACTAATAACTAACTAGG | 4 |  |  |
| Blb22-T | SCAR | F: CTTTATTAGTTCCAAGAGCTAC | 5 | 56 |  |
|  |  | R: ACCCATCCCTTTTTCCTTATC | 6 |  |  |
| Blb25-S | CAPS | F: ACAGATGCTACGTCCATCAC | 7 | 56 | Alu1 |
|  |  | R: CTCCACATGCGATGCAAAAG | 8 |  |  |

TABLE 2-continued

Overview of markers and primers used for mapping and cloning

| Marker | Type | PCR primer (5' to 3') | SEQ ID NO. | Tma | Enzymeb |
|---|---|---|---|---|---|
| Blb25-T | CAPS | F: TTTCGATTATGGTGAGCCTTC | 9 | 56 | Hpy 188 |
|  |  | R: TAGAAAAGGGTGGTTGTGAC | 10 |  |  |
| RGH primers |  |  |  |  |  |
| RGH1 | CAPS | F: GGSAAGACCACTCTTGCAAG | 11 | 50 | HpyCH4IV |
|  |  | R: GGTTTTTAAGCTGCTAATGTTG | 12 |  |  |
| RGH2 | SCAR | F: GGSAAGACCACTCTTGCAAG | 13 | 50 | a.s. |
|  |  | R: TGGTYATAATYACTCTGCTGC | 14 |  |  |
| RGH3 | CAPS | F: ATGRCTGATGCMTTTRTGTC | 15 | 50 | HaeIII |
|  |  | R: CCYAAGTASAGAAAACACTGC | 16 |  |  |
| 4-PLOOP |  | F: GGiATGGGiGGiYTiGGiARGAC | 17 | 68 |  |
| 4-GLPL |  | R: TACiACAATiGCAAGiGGTAAMCC | 18 |  |  |
| 4-GLO2 |  | F: GTGTCTCTCAAGAGTACAACAC | 19 | 56 |  |
|  |  | R: GCTCGAACATCAAGTAGTTTCC | 20 |  |  |
| Blb3-start |  | F: ATGGCTGATGCCTTTCTRTCATTTG | 21 | 55 |  |
| Blb3-end |  | R: TCAGGAATCTCCTTTAAATTTGGAC | 22 |  |  |
| Blb3-prom |  | F: TCTTCCTTAGCATTCGTAGC | 23 | 55 |  |
|  |  | R: CTTTAGGAATACTAGTTTTGATTG | 24 |  |  |
| Blb3-ter |  | F: AGCTTTTCTGCCAAGCACATTGG | 25 | 55 |  |
|  |  | R: GTACCCTCCGTTTGTCGTTTGATC | 26 |  |  |
| Blb3-LRR-1-8 |  | F: CTCTTTATGTATCAGACATGGC | 27 | 55 |  |
|  |  | R: CAACATCTTTCCACTGATCAC | 28 |  |  |
| Blb3-prom-end |  | F: CCCCAAGTTGTATAATGGTTG | 29 | 55 |  |
| Blb3-orf-bg |  | R: TGCTTGAGTGATTGAATCTCC | 30 |  |  |
| Sto-orf-bg |  | R: GGCCATATTCAGACTGGGAG | 31 |  |  |
| Blb3-spe |  | F: AGCTTTTTGAGTGTGTAATTGG | 32 | 55 |  |
|  |  | R: GTAACTACGGACTCGAGGG | 33 |  |  |

TABLE 3

Amino acid sequence identity between Rpi-blb3 and Rpi-blb3 gene homologues, including Rpi-abpt, R2 and R2-like.

| blb3GH-B-(Rpi-blb3) | LZ-NBS-LRR | LZ | NBS | LRR |
|---|---|---|---|---|
| abptGH-C-(Rpi-abpt) | 95.9 | 97.9 | 95.4 | 95.6 |
| R2-likeGH-8-(R2-like) | 97.3 | 97.9 | 95.4 | 99.1 |
| R2GH-G3-(R2) | 92.6 | 89.4 | 91 | 95.6 |
| blb3GH-A | 81.7 | 86.5 | 91.6 | 70 |
| abptGH-A | 86.3 | 90.1 | 93.5 | 77.6 |
| R2-likeGH-2 | 86.4 | 86.5 | 89.6 | 82.6 |
| R2-likeGH-3 | 89.9 | 86.5 | 89.4 | 92.1 |
| R2-likeGH-5 | 91.4 | 86.5 | 91.6 | 93.5 |
| R2GH-2 | 94.2 | 97.9 | 94.6 | 92.4 |
| R2GH-3 | 84.7 | 89.4 | 89.1 | 77.9 |
| R2GH-5 | 87.9 | 89.4 | 93.2 | 81.5 |
| R2GH-7 | 88.2 | 97.2 | 92.4 | 79.7 |
| R2GH-8 | 91 | 88.7 | 90.7 | 92.4 |
| R2GH-9 | 86.6 | 89.4 | 89.4 | 82.4 |
| R2GH-11 | 87 | 90.1 | 89.1 | 83.2 |
| R2GH-12 | 85 | 89.4 | 88.8 | 78.8 |
| R2GH-13 | 86.9 | 97.9 | 88.6 | 80.3 |
| R2GH-14 | 84 | 87.9 | 88.8 | 76.8 |
| R2GH-15 | 83.8 | 90.1 | 87.7 | 76.8 |
| R2GH-16 | 86.7 | 87.9 | 89.1 | 83.2 |
| R2GH-D3 | 89.7 | 88.7 | 89.9 | 92.1 |
| R2GH-65 | 92.8 | 89.4 | 92.1 | 95 |
| LeBacGH-1 | 75.6 | 80.9 | 80.1 | 67.4 |
| LeBacGH-2 | 55.7 | 81.6 | 57.5 | 42.6 |
| LeBacGH-3 | 70.9 | 77.3 | 81.2 | 56.5 |
| LeBacGH-4 | 78.3 | 78 | 86.4 | 69.4 |
| LeBacGH-5 | 47.6 | 52.5 | 53.7 | 40 |

TABLE 3-continued

Amino acid sequence identity between Rpi-blb3 and Rpi-blb3 gene homologues, including Rpi-abpt, R2 and R2-like.

| blb3GH-B-(Rpi-blb3) | LZ-NBS-LRR | LZ | NBS | LRR |
|---|---|---|---|---|
| RPP13 | 34.9 | 31.9 | 50.1 | 23.2 |
| Rpi-blb1 | 24.4 | 19.9 | 32.4 | 20.6 |

TABLE 4

Characteristics of *P. infestans* isolates used in this study, and their putative virulence profiles.

| Isolate | Year | Geographic origin | Mating type | Obtained from | Virulence profile |
|---|---|---|---|---|---|
| 90128 | 1990 | Geldrop, Netherlands | A1 | Govers, Phytopathology WUR | 1.3.4.7.8.11 |
| USA618 | unknown | Toluca Valley, Mexico | A2 | Bill Fry, Cornell, USA | 1.2.3.6.7.11 |
| 89148-09 | 1989 | Netherlands | | Govers, Phytopathology WUR | 0 |
| IPO-0 | | Netherlands | | Kessel, PRI, WUR | 0 |
| IPO-C | | | | Kessel, PRI, WUR | 1.2.3.4.6.7.10.11 |
| VK98014 | 1998 | Veenkoloniën, Netherlands | A1 | Kessel, PRI, WUR | 1.2.4.11 |
| Dinteloord | | Dinteloord, Netherlands | | Kessel, PRI, WUR | 1.2.4 |
| EC1 | | Ecuador | | Birch, SCRI, Scotland | 3.4.7.11 |
| F95573 | 1995 | Flevoland, Netherlands | A1 | Govers, Phytopathology, WUR | 1.3.4.7.10.11 |
| IPO-428-2 | 1992 | Ede, Netherlands | A2 | Kessel, PRI, WUR | 1.3.4.6.7.8.11 |
| Katshaar | | Katshaar, Netherlands | | Kessel, PRI, WUR | 1.3.4.7.10.11 |
| PIC 99177 | 1999 | Metepec, Mexico | | Kessel, PRI, WUR (Flier et al., 2002) | 2.7 |
| PIC 99183 | 1999 | Metepec, Mexico | | Kessel, PRI, WUR (Flier et al., 2002) | 1.3.7 |
| PIC 99189 | 1999 | Metepec, Mexico | | Kessel, PRI, WUR (Flier et al., 2002) | 1.3.4.7.8.10 |
| PIC 99190 | 1999 | Metepec, Mexico | | Kessel, PRI, WUR (Flier et al., 2002) | 1.3.4.7 |
| PY23* | 1999 | GGO | | Govers, Phytopathology, WUR | 1.3.4.7 |

*PY23: INF-1 non producing derivative of the wild type *P. infestans* isolate 88069 (Kamoun et al; 1998; van West et al; 1999).

TABLE 5

Overview of resistance screening with a diverse set of *P. infestans* isolates

| spp | Genotype | Gene | Chr. | py 23 | IPO-0 | 90128 | H30P04 | VK98014 | IPO428-2 | Dintel | Katshaar |
|---|---|---|---|---|---|---|---|---|---|---|---|
| BLB | Blb8005-8 | Rpi-blb1 | 8 | R | R | R | R | R | R | R | R |
| BLB | Blb2002 | Rpi-blb2 | 6 | R | R | R | R | R | R | R | R |
| BLB | Blb99-256-3 | Rpi-blb3 | 4 | R | R | R | R | R | R | R | R |
| BLB | 707TG11-1 | Rpi-abpt | 4 | R | R | R | R | R | R | R | R |
| BLB | AM3778-16 | R2-like | 4 | R | R | R | R | R | R | R | R |
| DMS | BET95-4200-3 | R2 | 4 | R | R | R | R | R | R | Rq | R |
| | cv. Desiree | — | — | S | S | S | S | S | S | S | S |
| | cv. Bintje | — | — | S | S | S | S | S | S | S | S |

| spp | Genotype | F95573 | EC1 | 89148-09 | 99190 | 99183 | 99189 | IPO-C | USA618 | 99177 |
|---|---|---|---|---|---|---|---|---|---|---|
| BLB | Blb8005-8 | R | R | R | R | R | S | R | R | R |
| BLB | Blb2002 | R | R | R | R | R | R | R | R | R |
| BLB | Blb99-256-3 | R | R | R | S | | S | S | S | S |
| BLB | 707TG11-1 | R | R | R | | S | | S | S | S |
| BLB | AM3778-16 | R | R | R | S | | S | S | S | S |
| DMS | BET95-4200-3 | R | R | R | S | S | S | S | S | S |
| | cv. Desiree | S | S | S | S | S | S | S | S | S |
| | cv. Bintje | S | S | S | S | S | S | S | S | S |

R: resistant (incompatible interaction, no symptom or localized HR-like necrosis)
S: susceptible (compatible interaction, spreading lesion with sporulation)
Rq: intermediate phenotype (sporulation on 2 to 3 leaflets per compound leaf and localized HR on the other leaflets

REFERENCES

Bendahmane, A., Kanyuke, K. and Baulcombe, D. C. 1997. High-resolution genetical and physical mapping of the Rx gene for extreme resistance to potato virus X in tetraploid potato. Theor Appl Genet 95: 153-162

Bittner-Eddy et al., 2000. RPP13 is a simple locus in *Arabidopsis thaliana* for alleles that specify downy mildew resistance to different avirulence determinants in Perenospora parasitica. The Plant Journal 21, 177-188.

Hamilton, C. M., A. Frary, C. Lewis, and S. D. Tanksley. 1996. Stable transfer of intact high molecular weight DNA into plant chromosomes. Proc. Natl. Acad. Sci, USA 93:9975-9979

Heilersig, H. J. B.; Loonen, A. E. H. M.; Bergervoet-van Deelen, J. E. M. van; Wolters, A. M. A.; Visser, R. G. F. (2006) Post-transcriptional gene silencing of GBSSI in potato: effects of size and sequences of the inverted repeats. Plant Molecular Biology 60 (2006)5.—ISSN 0167-4412-p. 647-662.

Helgeson, J. P., Pohlman, J. D., Austin, S., Haberlach, G. T., Wielgus, S. M., Ronis, D., Zambolim, L., Tooley, P., McGrath, J. M., James, R. V. and Stevenson, W. R. 1998. Somatic hybrids between *Solanum bulbocastanum* and potato: a new source of resistance to late blight. Theor Appl Genet 96: 738-742

Hermsen, J. G. T. H. and Ramanna, M. S. 1973. Double-bridge hybrids of *Solanum bulbocastanum* and cultivars of *Solanum tuberosum*. Euphytica 22: 457-466

Li, X., Van Eck, H. J., Rouppe van der Voort, J. N. A. M., Huigen, D. J., Stam, P. and Jacobsen, E. 1998. Autotetraploids and genetic mapping using common AFLP markers: the R2 allele conferring resistance to *Phytophthora infestans* mapped on potato chromosome 4. Theor Appl Genet 96: 1121-1128

Michelmore, R. W., Paran, I. and Kesseli, R. V. 1991. Identification of markers linked to disease-resistance genes by bulked segregant analysis: A rapid method to detect markers in specific genomic regions by using segregating populations. Proc. Natl. Acad. Sci. USA 88: 9828-9832

Park T.-H., Vleeshouwers V. G. A. A., Hutten R. C. B., van Eck H. J., van der Vossen E. A. G., Jacobsen E. and Visser R. G. F. 2005a High-resolution mapping and analysis of the resistance locus Rpi-abpt against *Phytophthora infestans* in potato. Molecular Breeding 16, 33-39.

Park T.-H., Vleeshouwers V. G. A. A., Huigen D., van der Vossen E. A. G., van Eck H. J. and Visser R. G. F. 2005b. Characterization and high-resolution mapping of a late blight resistance locus similar to R2 in potato. Theoretical and Applied Genetics 111, 591-597.

Park T.-H., Gros J., Sikkema A., Vleeshouwers V. G. A. A. Muskens M., Allefs S., Jacobsen E., Visser R. G. F. and van der Vossen E. A. G. 2005c. The late blight resistance locus Rpi-blb3 from *Solanum bulbocastanum* belongs to a major late blight R gene cluster on chromosome 4 of potato. Molecular Plant-Microbe Interactions 18 (7), 722-729.

Rose, L. E., et al. 2004. The maintenance of extreme amino acid resistance diversity at the disease resistance gene RPP13 in *Arabidopsis thaliana*. Genetics 166, 1517-1527.

Rouppe van der Voort, J., Kanyuka, K., Van der Vossen, E., Bendahmane, A., Mooijman, P., Klein-Lankhorst, R., Stiekema, W., Baulcombe, D. and Bakker, J. 1999. Tight physical linkage of the nematode resistance gene Gpa2 and the virus resistance gene Rx on a single segment introgressed from the wild species *Solanum tuberosum* subsp. andigena CPC 1673 into cultivated potato. MPMI 12: 197-206

Sandbrink, J. M., Colon, L. T., Wolters, P. J. C. C. and Stiekema, W. J. 2000. Two related genotypes of *Solanum microdontum* carry different segregating alleles for field resistance to *Phytophthora infestans*. Molecular Breeding 6: 215-225 van der Hoeven, R., Ronning, C., Giovannoni, J., Martin, G. and Tanksley, S. 2002. Deductions about the number, organization, and evolution of genes in the tomato genome based on analysis of a large expressed sequence tag collection and selective genomic sequencing. The Plant Cell 14: 1441-1456 van der Vossen, E. A., Sikkema, A., Hekkert, B. T. L., Gros, J., Stevens, P., Muskens, M., Wouters, D., Pereira, A., Stiekema, W. J. and Allefs, S. 2003. An ancient R gene from the wild species *Solanum bulbocastanum* confers broad-spectrum resistance to *Phytophthora infestans* in cultivated potato and tomato. Plant Journal 36: 867-882 van der Vossen, E. A., Gros, J., Sikkema, A., Muskens, M., Wouters, D., Wolters, P., Pereira, A. and Allefs, S. 2005. The Rpi-blb2 gene from *Solanum bulbocastanum* is an Mi-1 gene homolog conferring broad-spectrum late blight resistance in potato. Plant J. 44: 208-222.

van Engelen, F. A., Molthoff, J. W., Conner, A. J., Nap, J.-P., Pereira, A. and Stiekema, W. J. (1995) pBINPLUS: an improved plant transformation vector base don pBIN19. Trans. Res. 4, 288-290

Vleeshouwers, V. G. A. A., van Dooijweert, W., Paul Keizer, L. C., Sijpkes, L., Govers, F., Colon, L. T. 1999. A laboratory assay for *Phytophthora infestans* resistance in various *Solanum* species reflects the field situation. Eur. J. Plant Pathol. 105:241-250.

Voinnet, O., Rivas, S., Mestre, P., and Baulcombe, D. 2003. An enhanced transient expression system in plants based on suppression of gene silencing by the p19 protein of tomato bushy stunt virus. The Plant Journal 33, 949-956.

Vos, P., Hogers, R., Bleeker, M, Reijans, M, van de Lee, T., Homes, M., Frijters, A., Pot, J., Peleman, J., Kuiper, M. and Zabeau, M. 1995. AFLP: a new technique for DNA fingerprinting. Nucleic Acids Research 23(21): 4407-4414

---

The invention claimed is:

1. An isolated or recombinant nucleic acid molecule comprising a nucleotide sequence encoding Rpi-blb3 which has the amino acid sequence SEQ ID NO:35 or a protein that at least partially maintains the effect of Rpi-blb3 comprising an amino acid sequence at least 95% homologous to SEQ ID NO:35.

2. The isolated or recombinant nucleic acid molecule of claim 1, wherein the protein comprises the amino acid sequence of Rpi-blb3 (SEQ ID NO:35), Rpi-abpt (SEQ ID NO:37), R2 (SEQ ID NO:39) or R2-like (SEQ ID NO:41).

3. The isolated or recombinant nucleic acid molecule of claim 1 comprising a nucleotide sequence which is SEQ ID NO:34, which is SEQ ID NO:36, which is SEQ ID NO:38 or which is SEQ ID NO:40.

4. A vector comprising the nucleotide sequence of claim 1.

5. A host cell comprising the nucleotide sequence of claim 1.

6. The host cell of claim 5 which is an *Agrobacterium* cell.

7. The host cell of claim 5 which is a plant cell.

8. The host cell of claim 5 wherein said nucleotide sequence is contained in a vector.

9. The host cell of claim 7 wherein said plant cell is a cell from a Solanaceae.

10. A transgenic plant comprising the host cell of claim 7.

11. A transgenic part derived from the plant of claim 10, which part comprises the nucleotide sequence.

12. The part of claim 11 which is a tuber.

13. A method for providing at least partial resistance or increasing resistance in a plant against an oomycete infection comprising providing a plant or a part thereof with the nucleic acid molecule of claim 1.

14. The method of claim 13, wherein said oomycete comprises *Phytophthora*.

15. The method of claim 13, wherein said plant is a plant from the Solanaceae family.

16. A method for producing a protein that confers oomycete resistance comprising
functionally linking the nucleotide to sequence of claim 1 to a regulatory sequence for expression and allowing said the nucleotide sequence to be expressed in a host cell.

17. The method of claim 14, wherein the *Phytophthora* is *Phytophthora infestans*.

* * * * *

UNITED STATES PATENT AND TRADEMARK OFFICE
CERTIFICATE OF CORRECTION

PATENT NO.         : 8,399,737 B2  Page 1 of 1
APPLICATION NO.    : 12/522704
DATED              : March 19, 2013
INVENTOR(S)        : Van Der Vossen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 716 days.

Signed and Sealed this
First Day of September, 2015

Michelle K. Lee
*Director of the United States Patent and Trademark Office*

SEQUENCE LISTING

<160> NUMBER OF SEQ ID NOS: 42

<210> SEQ ID NO 1
<211> LENGTH: 21
<212> TYPE: DNA
<213> ORGANISM: Artificial
<220> FEATURE:
<223> OTHER INFORMATION: primer

<400> SEQUENCE: 1
attcaaaatt ctagttccgc c                                      21

<210> SEQ ID NO 2
<211> LENGTH: 19
<212> TYPE: DNA
<213> ORGANISM: Artificial
<220> FEATURE:
<223> OTHER INFORMATION: primer

<400> SEQUENCE: 2
aacggcaaaa aagcaccac                                         19

```
<210> SEQ ID NO 3
<211> LENGTH: 23
<212> TYPE: DNA
<213> ORGANISM: Artificial
<220> FEATURE:
<223> OTHER INFORMATION: primer

<400> SEQUENCE: 3
gtttgatgta tgtttgttct tgc                                              23

<210> SEQ ID NO 4
<211> LENGTH: 23
<212> TYPE: DNA
<213> ORGANISM: Artificial
<220> FEATURE:
<223> OTHER INFORMATION: primer

<400> SEQUENCE: 4
taatgcacta ataactaact agg                                              23

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
ctttattagt tccaagagct ac                                               22

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
acccatccct ttttccttat c                                                21

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
acagatgcta cgtccatcac                                                  20

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
ctccacatgc gatgcaaaaa g                                                21

<210> SEQ ID NO 9
<211> LENGTH: 21
<212> TYPE: DNA
<213> ORGANISM: Artificial
<220> FEATURE:
<223> OTHER INFORMATION: primer
```

<400> SEQUENCE: 9
tttcgattat ggtgagcctt c                                              21

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
tagaaaaagg gtggttgtga c                                              21

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
ggsaagacca ctcttgcaag                                                20

<210> SEQ ID NO 12
<211> LENGTH: 22
<212> TYPE: DNA
<213> ORGANISM: Artificial
<220> FEATURE:
<223> OTHER INFORMATION: primer

<400> SEQUENCE: 12
ggtttttaag ctgctaatgt tg                                             22

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
ggsaagacca ctcttgcaag                                                20

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
tggtyataat yactctgctg c                                              21

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
atgrctgatg cmtttrtgtc                                                20

```
<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
ccyaagtasa gaaaacactg c                                              21

<210> SEQ ID NO 17
<211> LENGTH: 23
<212> TYPE: DNA
<213> ORGANISM: Artificial
<220> FEATURE:
<223> OTHER INFORMATION: primer
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: modified_base
<222> LOCATION: (12)..(12)
<223> OTHER INFORMATION: I
<220> FEATURE:
<221> NAME/KEY: modified_base
<222> LOCATION: (15)..(15)
<223> OTHER INFORMATION: I
<220> FEATURE:
<221> NAME/KEY: modified_base
<222> LOCATION: (18)..(18)
<223> OTHER INFORMATION: I

<400> SEQUENCE: 17
ggaatgggag gaytaggaar gac                                            23

<210> SEQ ID NO 18
<211> LENGTH: 24
<212> TYPE: DNA
<213> ORGANISM: Artificial
<220> FEATURE:
<223> OTHER INFORMATION: primer
<220> FEATURE:
<221> NAME/KEY: modified_base
<222> LOCATION: (4)..(4)
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: modified_base
<222> LOCATION: (16)..(16)
<223> OTHER INFORMATION: I

<400> SEQUENCE: 18
tacaacaata gcaagaggta amcc                                           24

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
gtgtctctca agagtacaac ac                                             22
```

```
<210> SEQ ID NO 20
<211> LENGTH: 22
<212> TYPE: DNA
<213> ORGANISM: Artificial
<220> FEATURE:
<223> OTHER INFORMATION: primer

<400> SEQUENCE: 20
gctcgaacat caagtagttt cc                                              22

<210> SEQ ID NO 21
<211> LENGTH: 25
<212> TYPE: DNA
<213> ORGANISM: Artificial
<220> FEATURE:
<223> OTHER INFORMATION: primer

<400> SEQUENCE: 21
atggctgatg cctttctrtc atttg                                           25

<210> SEQ ID NO 22
<211> LENGTH: 25
<212> TYPE: DNA
<213> ORGANISM: Artificial
<220> FEATURE:
<223> OTHER INFORMATION: primer

<400> SEQUENCE: 22
tcaggaatct cctttaaatt tggac                                           25

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
tcttccttag cattcgtagc                                                 20

<210> SEQ ID NO 24
<211> LENGTH: 24
<212> TYPE: DNA
<213> ORGANISM: Artificial
<220> FEATURE:
<223> OTHER INFORMATION: primer

<400> SEQUENCE: 24
ctttaggaat actagttttg attg                                            24

<210> SEQ ID NO 25
<211> LENGTH: 23
<212> TYPE: DNA
<213> ORGANISM: Artificial
<220> FEATURE:
<223> OTHER INFORMATION: primer

<400> SEQUENCE: 25
agcttttctg ccaagcacat tgg                                             23

<210> SEQ ID NO 26
<211> LENGTH: 24
<212> TYPE: DNA
<213> ORGANISM: Artificial
<220> FEATURE:
<223> OTHER INFORMATION: primer
```

```
<400> SEQUENCE: 26
gtaccctccg tttgtcgttt gatc                                              24

<210> SEQ ID NO 27
<211> LENGTH: 22
<212> TYPE: DNA
<213> ORGANISM: Artificial
<220> FEATURE:
<223> OTHER INFORMATION: primer

<400> SEQUENCE: 27
ctctttatgt atcagacatg gc                                                22

<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
caacatcttt ccactgatca c                                                 21

<210> SEQ ID NO 29
<211> LENGTH: 21
<212> TYPE: DNA
<213> ORGANISM: Artificial
<220> FEATURE:
<223> OTHER INFORMATION: primer

<400> SEQUENCE: 29
ccccaagttg tataatggtt g                                                 21

<210> SEQ ID NO 30
<211> LENGTH: 21
<212> TYPE: DNA
<213> ORGANISM: Artificial
<220> FEATURE:
<223> OTHER INFORMATION: primer

<400> SEQUENCE: 30
tgcttgagtg attgaatctc c                                                 21

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
ggccatattc agactgggag                                                   20

<210> SEQ ID NO 32
<211> LENGTH: 22
<212> TYPE: DNA
<213> ORGANISM: Artificial
<220> FEATURE:
<223> OTHER INFORMATION: primer

<400> SEQUENCE: 32 agcttttga gtgtgtaatt gg                                                 22
```

```
<210> SEQ ID NO 33
<211> LENGTH: 19
<212> TYPE: DNA
<213> ORGANISM: Artificial
<220> FEATURE:
<223> OTHER INFORMATION: primer

<400> SEQUENCE: 33
gtaactacgg actcgaggg                                                   19

<210> SEQ ID NO 34
<211> LENGTH: 8461
<212> TYPE: DNA
<213> ORGANISM: Solanum bulbocastanum
<220> FEATURE:
<221> NAME/KEY: CDS
<222> LOCATION: (2944)..(5487)

<400> SEQUENCE: 34
gatcaaaaac ggattcgggg agtgaaaagc ttaccgttag cctcaagaac gatggaaaac       60
tatcaagagt cgtctggggt tcgttcctta gctctaaaaa tcgaaaagtg cagaataaag      120
acgttttgag gcttatttac gcactacaaa aaaatcatat attgctgcaa aatttgttgt      180
agctaaatat gaaaatttcc atggctaaac ttcaatattt tcttccttag cattcgtagc      240
aagatatagc atggctaaaa gttagctaca aactttacat ggttcatggc tgagaactaa      300
tatctattgc tacaaaattt ttgagttgta gctgtactga taaaaagttt ttgccacaca      360
aaatatatat atatatatag caaataactt tattcttttg ccacgtcaaa aatgatttat      420
agttgtcttt ttagatgcag ccacaaagct attacattgt agcaacatat ttaatttggt      480
ttccatgtaa acagaaattt gtagctattt gtatagctta gtcacgtggc aatagtactc      540
gtatttagtt atgactatta aaattcatgg caataacatg aagtatttac cacaagcatt      600
ttcgaattat agctaaaatt catatcttta gccatgaata tatataattt tagctaaaaa      660
tccatttgct acgaaagtca aaattttatat acatgttttt ttacgtgata tatatagaaa      720
atttgttgca ttcaatatat aattccatta ttattagaga tttttttcgca agctttatta      780 gttccaagag ctacataatg tagctatgaa ttaattttta agatttcaaa acacttccta      840
aattacgtat aattcaaatt tacaatttta aaaatagttc taattatata taactcatgt      900
aatacactat cttgtttgag tacaaagcag tatagtcttc tcttatttct ccttccacaa      960
cgttcaattg aatcttagct tgatttacac cgatcttgtc atttagatgc tttaactcca     1020
ttgatatacc tatcaaaatg atgaagtatt tcaacaccaa caatcattac caactaatta     1080
tagatgagag tgtgtgttat ataatatttc aagaagacaa caaatttatt tatatatata     1140
tcattagcta aaaaatttga agatacaaa caaaatatg caagaaaaaa agtaaacaa        1200 atctataaac ttttatttct taaaataatg ttcacctcaa ttgtgacatt tttggcggtt     1260
tgcgaattat gactcctctc aacactattt aaattttaaa atcttcacaa tctgctcata     1320
aataagatgt aatatttttt aaaagatcta aaataatcta aacccaaaaa tctaagtcaa     1380
ataagtgaaa cataaattcg aaaattgtaa ataagaagat atgaacatgc cttgaatata     1440
aaaaaaccac aaaagaaat tagcaaaaca ttctacattt tgaaatgcca aagtcttctc      1500
tctcaacatt tatctcttga gcaagaagat ttccatgtaa acttcatgtc ctttacttta     1560
agcattactt ccgatattgt tcttacctttt gtcaaggaac ctagtccatt gacctatggt    1620
ggacacagat aagctaacaa catttaatac cctaactacc attaccacaa caggtagagt     1680
acgctgaatt tttctaagtt gtgtcaccat ttaaaggaca aaaatgactc aagagtaaaa     1740
```

```
tcaatgaagc atttgctgca ggcctccaaa agttttatcg atatattttt ttttaataat    1800
ttgctcgttc ttccaaatca gttgaaactt gagttgttaa aattgatttg gtacgtctgg    1860
attttttttc aaataatacc gctccatcaa atttagatta atatgatgta atatgcacaa    1920
ttagaattgc ggacaattgt aaccaattta atgaattcaa aattatttca ttgtaacaag    1980
caaatagtaa aaaataaaat tattattatg aacaaataaa aagggacaag gcataagtac    2040
tctcctagac tatgactgaa atctcagaaa cacacataaa cttaactagg gtcctattac    2100
cccctaaact aatttaaaat ggaataaata caccacaaac ggtgacatga catagagagt    2160
gtacacactc tattgaaggc aattgattag tgcacaaatt ggacacatgt cattttttta    2220
ttgataactt tattattagt tagtacacat atttattgat aataaaaatt atatatatat    2280
aattattttt atttctttct ttgtaaaata tttattttaa tttcttttta ctttaaactt    2340 tttttattt aatttattat gttttcactt ttgattattt aaaaaaaatt tatgtgtatt    2400
ttttaaaaaa gtaattttaa agtgtccttt aattttaatg ttttaacttt tttatgtttt    2460
atttgaattt cttcacttat tttaatatcc gttcaattta atgaatccta aattatttca    2520
ttgtaacaag taaatagaaa aaaataaaat aagtcttatg aagaaataaa aacaaatata    2580 tttttttccac aagttgtgta atgattgttg aagatgcttc cattttttaa atcttttctc    2640
aatatatatt ttccacaagt tgtgcaatga ttgctgaagt tgcttattg ttttaagact     2700 tttctctata tgtgtttttc cccaagttgt ataatggttg ttgaagatgc tttaattaaa    2760
aaaaaaaacc ttttgtttag tggaaaattt caaaaagctt tagtacatct ttgtcgtttt    2820
atccaatcgt aattctttat tcagaaacca catgttttt ttctaatctt acttttatgt     2880
ctatcaccca ttttccaata tacagcctac tctttttttc aatcaaaact agtattccta    2940 aag atg gct gat gcc ttt cta tca ttt gca gtt caa aaa ttg ggt gat      2988
    Met Ala Asp Ala Phe Leu Ser Phe Ala Val Gln Lys Leu Gly Asp
    1               5                   10                  15 ttc cta ata cag aaa gtt tcc ctg cgt aaa agt ctc aga gat gaa att      3036
Phe Leu Ile Gln Lys Val Ser Leu Arg Lys Ser Leu Arg Asp Glu Ile
                20                  25                  30 aga tgg ctg ata aat gag cta ctc ttc ata cgg tct ttc ctc aga gat      3084
Arg Trp Leu Ile Asn Glu Leu Leu Phe Ile Arg Ser Phe Leu Arg Asp
        35                  40                  45 gca gaa caa aag cag tgc gga gat caa aga gtt caa caa tgg gtg ttt      3132
Ala Glu Gln Lys Gln Cys Gly Asp Gln Arg Val Gln Gln Trp Val Phe
    50                  55                  60 gag atc aac tct att gct aat gat gct gtt gct ata ctc gag act tat      3180
Glu Ile Asn Ser Ile Ala Asn Asp Ala Val Ala Ile Leu Glu Thr Tyr
65                  70                  75 agc ttt gag gct ggt aaa ggt gct agt cgt ctc aag gct tgc act tgc      3228
Ser Phe Glu Ala Gly Lys Gly Ala Ser Arg Leu Lys Ala Cys Thr Cys
80                  85                  90                  95 ata tgt agg aag gag aag aaa ttc tac aat gtt gcc gag gag att caa      3276
Ile Cys Arg Lys Glu Lys Lys Phe Tyr Asn Val Ala Glu Glu Ile Gln
                100                 105                 110 tca ctc aag caa cga atc atg gat atc tct cgc aaa cga gag act tat      3324
Ser Leu Lys Gln Arg Ile Met Asp Ile Ser Arg Lys Arg Glu Thr Tyr
            115                 120                 125 ggt att aca aat atc aat tat aat tca gga gaa agg cca agt aat cag      3372
Gly Ile Thr Asn Ile Asn Tyr Asn Ser Gly Glu Arg Pro Ser Asn Gln
        130                 135                 140 gtt aca aca ttg agg aga act acc tca tat gta gat gaa cag gat tac      3420
Val Thr Thr Leu Arg Arg Thr Thr Ser Tyr Val Asp Glu Gln Asp Tyr
    145                 150                 155
```

```
att ttt gtt ggc ttt cag gat gtt gta caa aca ttg cta gct caa ctt    3468
Ile Phe Val Gly Phe Gln Asp Val Val Gln Thr Leu Leu Ala Gln Leu
160             165                 170                 175 ctg aaa gca gag cct cgt cga agc gtc ctc tcc att tat gga atg ggg    3516
Leu Lys Ala Glu Pro Arg Arg Ser Val Leu Ser Ile Tyr Gly Met Gly
        180                 185                 190 ggt tta ggc aag acc act ctt gcc aga aaa ctt tac acc agt cct gat    3564
Gly Leu Gly Lys Thr Thr Leu Ala Arg Lys Leu Tyr Thr Ser Pro Asp
            195                 200                 205 ata ctc aat agc ttt cct aca cgc gct tgg ata tgt gtc tct caa gag    3612
Ile Leu Asn Ser Phe Pro Thr Arg Ala Trp Ile Cys Val Ser Gln Glu
                210                 215                 220 tac aac aca atg gat ctt ctt agg act atc ata aaa tcc atc caa ggc    3660
Tyr Asn Thr Met Asp Leu Leu Arg Thr Ile Ile Lys Ser Ile Gln Gly
225                 230                 235 tgc gcc aag gaa act cta gat ttg ttg gaa aag atg gca gaa ata gat    3708
Cys Ala Lys Glu Thr Leu Asp Leu Leu Glu Lys Met Ala Glu Ile Asp
240                 245                 250                 255 cta gaa aat cac ctt cgt gat cta ttg aaa gaa tgc aaa tac ctt gtg    3756
Leu Glu Asn His Leu Arg Asp Leu Leu Lys Glu Cys Lys Tyr Leu Val
                260                 265                 270 gtg gtt gat gat gta tgg cag aga gaa gca tgg gag agt ttg aaa aga    3804
Val Val Asp Asp Val Trp Gln Arg Glu Ala Trp Glu Ser Leu Lys Arg
            275                 280                 285 gca ttc ccg gat ggc aag aat gga agc aga gtc att att acc acg cgc    3852
Ala Phe Pro Asp Gly Lys Asn Gly Ser Arg Val Ile Ile Thr Thr Arg
        290                 295                 300 aaa gag gat gtc gct gaa aga gta gac cac aga ggt ttt gtt cat aaa    3900
Lys Glu Asp Val Ala Glu Arg Val Asp His Arg Gly Phe Val His Lys
305                 310                 315 ctt cgt ttc cta agt caa gaa gaa agt tgg gat ctc ttt cgt agg aaa    3948
Leu Arg Phe Leu Ser Gln Glu Glu Ser Trp Asp Leu Phe Arg Arg Lys
320                 325                 330                 335 cta ctt gat gtt cga gca atg gtt cca gaa atg gaa agt tta gct aag    3996
Leu Leu Asp Val Arg Ala Met Val Pro Glu Met Glu Ser Leu Ala Lys
                340                 345                 350 gat atg gtg gaa aag tgt aga ggc tta cct ctt gca att gtt gta ttg    4044
Asp Met Val Glu Lys Cys Arg Gly Leu Pro Leu Ala Ile Val Val Leu
            355                 360                 365 agc gga cta ctt tcg cat aaa aag ggg cta aac caa tgg caa aag gtg    4092
Ser Gly Leu Leu Ser His Lys Lys Gly Leu Asn Gln Trp Gln Lys Val
        370                 375                 380 aaa gat cac ctt tgg aag aac att aaa gaa gat aaa tct att gaa atc    4140
Lys Asp His Leu Trp Lys Asn Ile Lys Glu Asp Lys Ser Ile Glu Ile
385                 390                 395 tct aac ata cta tcc tta agc tac aat gat ttg tca act gcg ctc aag    4188
Ser Asn Ile Leu Ser Leu Ser Tyr Asn Asp Leu Ser Thr Ala Leu Lys
400                 405                 410                 415 cag tgt ttt ctc tac ttt ggt att ttt cca gaa gat caa gtg gta aag    4236
Gln Cys Phe Leu Tyr Phe Gly Ile Phe Pro Glu Asp Gln Val Val Lys
                420                 425                 430 gct gat gac ata ata cgg ttg tgg atg gcg gag ggt ttc ata ccc aga    4284
Ala Asp Asp Ile Ile Arg Leu Trp Met Ala Glu Gly Phe Ile Pro Arg
            435                 440                 445 gga gaa gaa aga atg gag gat gtg gct gac ggc ttc ttg aat gaa ctg    4332
Gly Glu Glu Arg Met Glu Asp Val Ala Asp Gly Phe Leu Asn Glu Leu
        450                 455                 460 ata aga cga agc ttg gtt caa gta gct aaa aca ttt tgg gaa aaa gtt    4380
Ile Arg Arg Ser Leu Val Gln Val Ala Lys Thr Phe Trp Glu Lys Val
465                 470                 475
```

```
act gac tgt agg gtt cat gat tta ctt cgt gat ctt gcg ata caa aag    4428
Thr Asp Cys Arg Val His Asp Leu Leu Arg Asp Leu Ala Ile Gln Lys
480                 485                 490                 495 gca ttg gag gta aac ttc ttt gac gtt tat ggt cca aga agc cac tcc    4476
Ala Leu Glu Val Asn Phe Phe Asp Val Tyr Gly Pro Arg Ser His Ser
                500                 505                 510 ata tcc tct tta tgt atc aga cat ggc att cat agt gaa gga gaa agg    4524
Ile Ser Ser Leu Cys Ile Arg His Gly Ile His Ser Glu Gly Glu Arg
            515                 520                 525 tac ctc tca tca ctt gat ctt tct aac ttg aag ttg agg tca att atg    4572
Tyr Leu Ser Ser Leu Asp Leu Ser Asn Leu Lys Leu Arg Ser Ile Met
        530                 535                 540 ttc ttc gat cca gat ttt cgt aag atg agt cat ata aac ctc agg agt    4620
Phe Phe Asp Pro Asp Phe Arg Lys Met Ser His Ile Asn Leu Arg Ser
    545                 550                 555 gag ttc caa cat ctg tat gtg ttg tac ttg gat acg aat ttt ggg tat    4668
Glu Phe Gln His Leu Tyr Val Leu Tyr Leu Asp Thr Asn Phe Gly Tyr
560                 565                 570                 575 gtg tct atg gta cct gat gcc ata gga agt ttg tac cac ctc aag ttg    4716
Val Ser Met Val Pro Asp Ala Ile Gly Ser Leu Tyr His Leu Lys Leu
                580                 585                 590 tta aga ttg aga ggt atc cat gat att ccg tct tcc att ggc aac ctc    4764
Leu Arg Leu Arg Gly Ile His Asp Ile Pro Ser Ser Ile Gly Asn Leu
            595                 600                 605 aag aat tta caa aca ctt gtc gtt gta aat ggt tac aca ttt ttt tgc    4812
Lys Asn Leu Gln Thr Leu Val Val Val Asn Gly Tyr Thr Phe Phe Cys
        610                 615                 620 caa cta ccc tgc aag aca gct gac cta ata aat cta aga cat tta gtt    4860
Gln Leu Pro Cys Lys Thr Ala Asp Leu Ile Asn Leu Arg His Leu Val
    625                 630                 635 gtt caa tat tca gag cct tta aaa tgt ata aac aaa ctc act agt ctt    4908
Val Gln Tyr Ser Glu Pro Leu Lys Cys Ile Asn Lys Leu Thr Ser Leu
640                 645                 650                 655 caa gtt ctt gat ggt gtt gct tgt gat cag tgg aaa gat gtt gac cct    4956
Gln Val Leu Asp Gly Val Ala Cys Asp Gln Trp Lys Asp Val Asp Pro
                660                 665                 670 gtt gat tta gtc aat ctt cga gaa tta agc atg gat cgt atc agg agc    5004
Val Asp Leu Val Asn Leu Arg Glu Leu Ser Met Asp Arg Ile Arg Ser
            675                 680                 685 tct tac tcc cta aac aac att agc agc ttg aaa aac ctt agc act ctc    5052
Ser Tyr Ser Leu Asn Asn Ile Ser Ser Leu Lys Asn Leu Ser Thr Leu
        690                 695                 700 aaa ttg att tgt gga gaa cgt caa tca ttt gca tcc ctt gaa ttt gtt    5100
Lys Leu Ile Cys Gly Glu Arg Gln Ser Phe Ala Ser Leu Glu Phe Val
    705                 710                 715 aat tgt tgt gaa aag ctc cag aaa ttg tgg tta caa ggg aga ata gag    5148
Asn Cys Cys Glu Lys Leu Gln Lys Leu Trp Leu Gln Gly Arg Ile Glu
720                 725                 730                 735 gaa ctg cct cat ctg ttt tca aac tcc atc aca atg atg gtt ctg agt    5196
Glu Leu Pro His Leu Phe Ser Asn Ser Ile Thr Met Met Val Leu Ser
                740                 745                 750 ttc tca gaa ctg aca gaa gat ccg atg cct att ttg gga agg ttt cca    5244
Phe Ser Glu Leu Thr Glu Asp Pro Met Pro Ile Leu Gly Arg Phe Pro
            755                 760                 765 aac cta agg aat ctc aaa tta gat gga gct tat gaa gga aaa gaa ata    5292
Asn Leu Arg Asn Leu Lys Leu Asp Gly Ala Tyr Glu Gly Lys Glu Ile
        770                 775                 780 atg tgc agt gat aac agc ttc agt caa cta gag ttc ctt cat ctt cgt    5340
Met Cys Ser Asp Asn Ser Phe Ser Gln Leu Glu Phe Leu His Leu Arg
    785                 790                 795
```

```
gat ctt tgg aag cta gaa aga tgg gat tta ggc aca agt gcc atg cct      5388
Asp Leu Trp Lys Leu Glu Arg Trp Asp Leu Gly Thr Ser Ala Met Pro
800                 805                 810                 815 ctg att aaa ggt ctt ggt atc cat aac tgt cca aat tta aag gag att      5436
Leu Ile Lys Gly Leu Gly Ile His Asn Cys Pro Asn Leu Lys Glu Ile
                820                 825                 830 cct gag aga atg aaa gac atg gag ctg ttg aag cgg aat tat atg ttg      5484
Pro Glu Arg Met Lys Asp Met Glu Leu Leu Lys Arg Asn Tyr Met Leu
            835                 840                 845 tga agcttttctg ccaagcacat tggttattaa ttgagtggtt ttagtgttga           5537
tttcttatta ttgttttaag cttttgagt gtgtaattgg tttgaacatt attgttttaa     5597
ttaattggtc tactgtatgt tctcatgctt atccacattt aagacaatgc tttatatgtt    5657
aaaatgaaat taaaaatact agtatatggt actctctctt gtccacaatt tcgtatattt    5717
tttgttcctc ttcataaaaa aatggtaaaa aaataccatt aaactatgtg ataggaacaa    5777
aaatgtcttc tattataatt taacttaaaa atgtctttac tgtcagtacc ttagttcaaa    5837
attgccctcg agtccgtagt tacaaaatgt ccttttcga ataaatatat atattttttt     5897
aaacacatct tcttcctaat taaaatatta ttaaagaaga ctattcttgt tttctttttt    5957
ctaaaaatca ctttaacaaa taaaaatgta ggaaatattt tgttttcttc ttaatctcac    6017
tttatcaatt aaaatagaat aactccatgt acccttcga catataatat atgtcatata     6077
tatatataag atcatagtat atgcatcatt aatttatatt tatataacga taaaaaataa    6137
tgataataaa ataagaaata tttttatttt ttattttctt ctgaattgaa gtaatataaa    6197
catttgctaa ttttaaaaaa aaataataca aaaataatgt gttaaaaaga aataataat     6257 atatttattt ggaaaatgag tattttttgat ccattaaata acagtaagtg tattttttaga  6317 ccaaagtatt gacaacaagg gtattttttgg atcaaacgac aaacggaggg tacttttgct   6377
cctttcgcat aatttaaggg tattttttaaa ccaaaatatt gacggtaaag gcattttttga  6437 gtcaaattat gaacgaaaga cattttttatt tctttcacat agtttaagga cattttttgac 6497 ccatttccct cctttatata aataatattt atgttaaatc aacagagaag aagctgtcaa    6557
ttgaagacat tcactttcat caacttggct tctccaagca tcaatcaact tggattattt    6617
caacattctg ttttttcaat gtttaatttc tttctatttt tggaaacatg tgttggaaga    6677
gaaccttttt tctggatttt gtgatgacct aattaacgaa acaaagttaa aaatgttctt    6737
aaattatgta aaatgaataa aaatatcctc agttaatagt ttgatccaaa atatattgttg   6797 tctctaataa ttgatctaaa aatgatatta ttgttactta ataagtgaaa accgtctttt    6857
tttcaattaa atatattatt tttctttttt taaaacacgc tcttttccta ataatgattt    6917
tttttcatta aaaaatattc atcctacttc aatttataaa aatattact aataaataaa     6977 aatgtttttt atattattag aaagtttttt atcgttattt aaatgaaaat taatgacggg    7037
gttactatga ggacatataa tggaagaagt tgagaactcg cttagtgtga agcgagaata    7097
actaaaaaaa aaaaaaaaac ttacaaactc gcttggtgcg gagcgatttt tgggggaaaa    7157
tagagagcaa atcgctcata ggtagcgaga aaaaaagat aaaataaaag agaaaatcgc     7217
tcgtaagtca acaagatgat caatttttt atgccgttaa cgatagttat agcacaaaca     7277
tatctcgctc cttctctagc aaagtgtccc ttttgattaa accaaaaatt gaaagaccct    7337
ttatgtattt taaagaaaaa aagtgatgtt tttaactttg aattcgaaat ttaatcatcc    7397
caatataatt cataaacgaa tttttacatc aattttaaaa taaagaataa aaaaaagaaa    7457
gataatatat actagcaggg aactacatgt gattactaca aaagataaat tcaatttcag    7517
```

-continued

```
gtggtatttg gatttgaatt gtcttacctt gctatcataa cattattttt gtttttatcc    7577
attaaaaaaa tgatgcattt atatatttat tactagtaaa gtaatatctt taatgtgtca    7637
acacataagt atccctcaat tagtaaaatg ttaggacttt tttcatgtga gaaacccaac    7697
ctcattgaaa aaggaaatta atacatttta actcaacttt taattaatta atgtcaagtt    7757
tgataaaaat aaataaaaaa acaatcgtag acaatctcta attattagaa ttttacaata    7817
tgcatattta atgggttata taaattttga gttggccttc ttttttttctt cttgtgattc    7877
taagtcctcc actttatttt tattttttata tttataatta aatattttttt actcgattca    7937
cagaccgagt tggaccagtc caatcttgat taagcctcac gagttgacga gcttatttag    7997
gcttggctaa ataatttcgt tcttaaatga acttttaatt tttttttgagc tcaatcctat    8057
caaatcgcag attaggttgg atttgggtga acaatggac caaagtccaa actaacagct    8117
ccaaaatcta cgaggtttag aaatagaaag tcttcttata tgttatgtat atctaacaaa    8177
ttatatgtta tgtatgatat tgtataaata gttatttaat gtatcaatat tgtataataa    8237
catatagtta tgtatttata atgtataact atatatgata ttgtataaat agttatttaa    8297
tgtatcgata ttgtatagta gcatatagtt atgtatttat aatgtatgta taactatgta    8357
tgatattgta taaatagatt ttggacttgg gaagtctgca gcaagcaaag gaagaggtcc    8417
aggtagcaac acttttatct taatgaatac accaaatgat gatc                     8461
```

<210> SEQ ID NO 35
<211> LENGTH: 847
<212> TYPE: PRT
<213> ORGANISM: Solanum bulbocastanum

<400> SEQUENCE: 35

```
Met Ala Asp Ala Phe Leu Ser Phe Ala Val Gln Lys Leu Gly Asp Phe
1               5                   10                  15

Leu Ile Gln Lys Val Ser Leu Arg Lys Ser Leu Arg Asp Glu Ile Arg
            20                  25                  30

Trp Leu Ile Asn Glu Leu Leu Phe Ile Arg Ser Phe Leu Arg Asp Ala
        35                  40                  45

Glu Gln Lys Gln Cys Gly Asp Gln Arg Val Gln Trp Val Phe Glu
    50                  55                  60

Ile Asn Ser Ile Ala Asn Asp Ala Val Ala Ile Leu Glu Thr Tyr Ser
65                  70                  75                  80

Phe Glu Ala Gly Lys Gly Ala Ser Arg Leu Lys Ala Cys Thr Cys Ile
                85                  90                  95

Cys Arg Lys Glu Lys Lys Phe Tyr Asn Val Ala Glu Glu Ile Gln Ser
            100                 105                 110

Leu Lys Gln Arg Ile Met Asp Ile Ser Arg Lys Arg Glu Thr Tyr Gly
        115                 120                 125

Ile Thr Asn Ile Asn Tyr Asn Ser Gly Glu Arg Pro Ser Asn Gln Val
    130                 135                 140

Thr Thr Leu Arg Arg Thr Thr Ser Tyr Val Asp Glu Gln Asp Tyr Ile
145                 150                 155                 160

Phe Val Gly Phe Gln Asp Val Val Gln Thr Leu Leu Ala Gln Leu Leu
                165                 170                 175

Lys Ala Glu Pro Arg Arg Ser Val Leu Ser Ile Tyr Gly Met Gly Gly
            180                 185                 190

Leu Gly Lys Thr Thr Leu Ala Arg Lys Leu Tyr Thr Ser Pro Asp Ile
        195                 200                 205
```

-continued

```
Leu Asn Ser Phe Pro Thr Arg Ala Trp Ile Cys Val Ser Gln Glu Tyr
    210                 215                 220
Asn Thr Met Asp Leu Leu Arg Thr Ile Ile Lys Ser Ile Gln Gly Cys
225                 230                 235                 240
Ala Lys Glu Thr Leu Asp Leu Leu Glu Lys Met Ala Glu Ile Asp Leu
                245                 250                 255
Glu Asn His Leu Arg Asp Leu Leu Lys Glu Cys Lys Tyr Leu Val Val
            260                 265                 270
Val Asp Asp Val Trp Gln Arg Glu Ala Trp Glu Ser Leu Lys Arg Ala
        275                 280                 285
Phe Pro Asp Gly Lys Asn Gly Ser Arg Val Ile Thr Thr Arg Lys
    290                 295                 300
Glu Asp Val Ala Glu Arg Val Asp His Arg Gly Phe Val His Lys Leu
305                 310                 315                 320
Arg Phe Leu Ser Gln Glu Ser Trp Asp Leu Phe Arg Arg Lys Leu
                325                 330                 335
Leu Asp Val Arg Ala Met Val Pro Glu Met Glu Ser Leu Ala Lys Asp
                340                 345                 350
Met Val Glu Lys Cys Arg Gly Leu Pro Leu Ala Ile Val Val Leu Ser
            355                 360                 365
Gly Leu Leu Ser His Lys Lys Gly Leu Asn Gln Trp Gln Lys Val Lys
    370                 375                 380
Asp His Leu Trp Lys Asn Ile Lys Glu Asp Lys Ser Ile Glu Ile Ser
385                 390                 395                 400
Asn Ile Leu Ser Leu Ser Tyr Asn Asp Leu Ser Thr Ala Leu Lys Gln
                405                 410                 415
Cys Phe Leu Tyr Phe Gly Ile Phe Pro Glu Asp Gln Val Val Lys Ala
                420                 425                 430
Asp Asp Ile Ile Arg Leu Trp Met Ala Glu Gly Phe Ile Pro Arg Gly
            435                 440                 445
Glu Glu Arg Met Glu Asp Val Ala Asp Gly Phe Leu Asn Glu Leu Ile
    450                 455                 460
Arg Arg Ser Leu Val Gln Val Ala Lys Thr Phe Trp Glu Lys Val Thr
465                 470                 475                 480
Asp Cys Arg Val His Asp Leu Leu Arg Asp Leu Ala Ile Gln Lys Ala
                485                 490                 495
Leu Glu Val Asn Phe Phe Asp Val Tyr Gly Pro Arg Ser His Ser Ile
                500                 505                 510
Ser Ser Leu Cys Ile Arg His Gly Ile His Ser Glu Gly Glu Arg Tyr
            515                 520                 525
Leu Ser Ser Leu Asp Leu Ser Asn Leu Lys Leu Arg Ser Ile Met Phe
    530                 535                 540
Phe Asp Pro Asp Phe Arg Lys Met Ser His Ile Asn Leu Arg Ser Glu
545                 550                 555                 560
Phe Gln His Leu Tyr Val Leu Tyr Leu Asp Thr Asn Phe Gly Tyr Val
                565                 570                 575
Ser Met Val Pro Asp Ala Ile Gly Ser Leu Tyr His Leu Lys Leu Leu
                580                 585                 590
Arg Leu Arg Gly Ile His Asp Ile Pro Ser Ser Ile Gly Asn Leu Lys
            595                 600                 605
Asn Leu Gln Thr Leu Val Val Asn Gly Tyr Thr Phe Phe Cys Gln
    610                 615                 620
Leu Pro Cys Lys Thr Ala Asp Leu Ile Asn Leu Arg His Leu Val Val
625                 630                 635                 640
```

```
Gln Tyr Ser Glu Pro Leu Lys Cys Ile Asn Lys Leu Thr Ser Leu Gln
            645                 650                 655

Val Leu Asp Gly Val Ala Cys Asp Gln Trp Lys Asp Val Asp Pro Val
        660                 665                 670

Asp Leu Val Asn Leu Arg Glu Leu Ser Met Asp Arg Ile Arg Ser Ser
        675                 680                 685

Tyr Ser Leu Asn Asn Ile Ser Ser Leu Lys Asn Leu Ser Thr Leu Lys
        690                 695                 700

Leu Ile Cys Gly Glu Arg Gln Ser Phe Ala Ser Leu Glu Phe Val Asn
705                 710                 715                 720

Cys Cys Glu Lys Leu Gln Lys Leu Trp Leu Gln Gly Arg Ile Glu Glu
                725                 730                 735

Leu Pro His Leu Phe Ser Asn Ser Ile Thr Met Met Val Leu Ser Phe
            740                 745                 750

Ser Glu Leu Thr Glu Asp Pro Met Pro Ile Leu Gly Arg Phe Pro Asn
        755                 760                 765

Leu Arg Asn Leu Lys Leu Asp Gly Ala Tyr Glu Gly Lys Glu Ile Met
        770                 775                 780

Cys Ser Asp Asn Ser Phe Ser Gln Leu Glu Phe Leu His Leu Arg Asp
785                 790                 795                 800

Leu Trp Lys Leu Glu Arg Trp Asp Leu Gly Thr Ser Ala Met Pro Leu
                805                 810                 815

Ile Lys Gly Leu Gly Ile His Asn Cys Pro Asn Leu Lys Glu Ile Pro
            820                 825                 830

Glu Arg Met Lys Asp Met Glu Leu Leu Lys Arg Asn Tyr Met Leu
        835                 840                 845

<210> SEQ ID NO 36
<211> LENGTH: 2538
<212> TYPE: DNA
<213> ORGANISM: Solanum bulbocastanum
<220> FEATURE:
<221> NAME/KEY: CDS
<222> LOCATION: (1)..(2538)

<400> SEQUENCE: 36 atg gct gat gcc ttt cta tca ttt gca gtt caa aaa ttg ggt gat ttc      48
Met Ala Asp Ala Phe Leu Ser Phe Ala Val Gln Lys Leu Gly Asp Phe
1               5                   10                  15 cta ata cag aaa gtt tcc ctg cgt aaa agt ctc aga gac gaa att aga     96
Leu Ile Gln Lys Val Ser Leu Arg Lys Ser Leu Arg Asp Glu Ile Arg
            20                  25                  30 tgg ctg atc aat gag cta ctc ttc ata cgg tct ttc ctc aga gat gca    144
Trp Leu Ile Asn Glu Leu Leu Phe Ile Arg Ser Phe Leu Arg Asp Ala
        35                  40                  45 gaa caa aag cag tgc gga gat caa aga gtt caa caa tgg gtg ttt gag    192
Glu Gln Lys Gln Cys Gly Asp Gln Arg Val Gln Gln Trp Val Phe Glu
    50                  55                  60 atc aac tct att gct aat gat gct gtt gct ata ctc gag act tat agc    240
Ile Asn Ser Ile Ala Asn Asp Ala Val Ala Ile Leu Glu Thr Tyr Ser
65                  70                  75                  80 ttt gag gct ggt aaa ggt gct agt cgt ctc aag gct tgc act tgc ata    288
Phe Glu Ala Gly Lys Gly Ala Ser Arg Leu Lys Ala Cys Thr Cys Ile
                85                  90                  95 tgt agg aag gag aag aaa ttc tac aat gtt gcc gag gag att caa tca    336
Cys Arg Lys Glu Lys Lys Phe Tyr Asn Val Ala Glu Glu Ile Gln Ser
            100                 105                 110
```

```
ctc aag caa cga atc atg gat atc tct cgc aaa cga gag act tat ggt     384
Leu Lys Gln Arg Ile Met Asp Ile Ser Arg Lys Arg Glu Thr Tyr Gly
        115                 120                 125 att aca aat atc aat aat aat gca gga gaa ggg cca agt aat cag gtt     432
Ile Thr Asn Ile Asn Asn Asn Ala Gly Glu Gly Pro Ser Asn Gln Val
130                 135                 140 aca aaa ttg agg aga act acc tca tat gta gat gaa cag gat tac att     480
Thr Lys Leu Arg Arg Thr Thr Ser Tyr Val Asp Glu Gln Asp Tyr Ile
145                 150                 155                 160 ttt gtt ggc ttt cag gat gtt gta caa aca ttt cta gct caa ctt ctg     528
Phe Val Gly Phe Gln Asp Val Val Gln Thr Phe Leu Ala Gln Leu Leu
                165                 170                 175 aaa gca gag cct cgt cga agc gtc ctc tcc att tat gga atg ggg ggt     576
Lys Ala Glu Pro Arg Arg Ser Val Leu Ser Ile Tyr Gly Met Gly Gly
            180                 185                 190 tta ggc aag acc act ctt gcc aga aaa ctt tac acc agt cct gat ata     624
Leu Gly Lys Thr Thr Leu Ala Arg Lys Leu Tyr Thr Ser Pro Asp Ile
        195                 200                 205 ctc aat agc ttc cgt aca cgc gct tgg ata tgt gtc tct caa gag tac     672
Leu Asn Ser Phe Arg Thr Arg Ala Trp Ile Cys Val Ser Gln Glu Tyr
    210                 215                 220 aac aca atg gat ctt ctt agg aat atc ata aaa tcc atc caa ggt cgc     720
Asn Thr Met Asp Leu Leu Arg Asn Ile Ile Lys Ser Ile Gln Gly Arg
225                 230                 235                 240 acc aag gaa act cta gat ttg ttg gaa agg atg aca gaa gga gat ctt     768
Thr Lys Glu Thr Leu Asp Leu Leu Glu Arg Met Thr Glu Gly Asp Leu
                245                 250                 255 gaa att tat ctt cgt gat tta ttg aaa gaa cgc aaa tac ctt gtg gtg     816
Glu Ile Tyr Leu Arg Asp Leu Leu Lys Glu Arg Lys Tyr Leu Val Val
            260                 265                 270 gtt gat gat gta tgg cag aga gaa gca tgg gag agt ttg aaa aga tca     864
Val Asp Asp Val Trp Gln Arg Glu Ala Trp Glu Ser Leu Lys Arg Ser
        275                 280                 285 ttc ccg gat ggc aag aat ggc agc aga gtc att att acc acg cgc aaa     912
Phe Pro Asp Gly Lys Asn Gly Ser Arg Val Ile Ile Thr Thr Arg Lys
    290                 295                 300 gag gat gtc gct gaa aga gca gac gac aga ggt ttt gtt cat aaa ctt     960
Glu Asp Val Ala Glu Arg Ala Asp Asp Arg Gly Phe Val His Lys Leu
305                 310                 315                 320 cgt ttc cta agc caa gaa gaa agt tgg gat ctc ttt cgt agg aaa cta    1008
Arg Phe Leu Ser Gln Glu Glu Ser Trp Asp Leu Phe Arg Arg Lys Leu
                325                 330                 335 ctt gat gtt cga gca atg gtt cca gaa atg gaa agt cta gct aag gat    1056
Leu Asp Val Arg Ala Met Val Pro Glu Met Glu Ser Leu Ala Lys Asp
            340                 345                 350 atg gtg gaa aag tgt aga ggc tta cct ctt gca att gtt gta ttg agc    1104
Met Val Glu Lys Cys Arg Gly Leu Pro Leu Ala Ile Val Val Leu Ser
        355                 360                 365 gga cta ctt tcg cat aaa aag ggg cta aac caa tgg caa aag gtg aaa    1152
Gly Leu Leu Ser His Lys Lys Gly Leu Asn Gln Trp Gln Lys Val Lys
    370                 375                 380 gat cac ctt tgg aag aac att aaa gaa gat aaa tct att gaa atc tct    1200
Asp His Leu Trp Lys Asn Ile Lys Glu Asp Lys Ser Ile Glu Ile Ser
385                 390                 395                 400 aac ata cta tcc tta agc tac aat gat ttg tca act gcg ctc aag cag    1248
Asn Ile Leu Ser Leu Ser Tyr Asn Asp Leu Ser Thr Ala Leu Lys Gln
                405                 410                 415 tgt ttt ctc tac ttt ggt att ttt cca gaa gat caa gtg gta aag gct    1296
Cys Phe Leu Tyr Phe Gly Ile Phe Pro Glu Asp Gln Val Val Lys Ala
            420                 425                 430
```

-continued

| | | |
|---|---|---|
| gat gac ata ata cgg ttg tgg atg gcg gag ggt ttc ata ccc aga gga<br>Asp Asp Ile Ile Arg Leu Trp Met Ala Glu Gly Phe Ile Pro Arg Gly<br>435                    440                    445 | | 1344 |
| gaa gaa aga atg gag gat gtg gct gac ggc ttc ttg aat gaa ctg ata<br>Glu Glu Arg Met Glu Asp Val Ala Asp Gly Phe Leu Asn Glu Leu Ile<br>450                    455                    460 | | 1392 |
| aga cga agc ttg gtt caa gta gct aaa aca ttt tgg gaa aaa gtt act<br>Arg Arg Ser Leu Val Gln Val Ala Lys Thr Phe Trp Glu Lys Val Thr<br>465                    470                    475                    480 | | 1440 |
| gac tgt agg gtt cat gat tta ctt cgt gat ctt gcg ata caa aag gca<br>Asp Cys Arg Val His Asp Leu Leu Arg Asp Leu Ala Ile Gln Lys Ala<br>                    485                    490                    495 | | 1488 |
| ttg gag gta aac ttc ttt gac att tat gat cca aga agc cac tcc ata<br>Leu Glu Val Asn Phe Phe Asp Ile Tyr Asp Pro Arg Ser His Ser Ile<br>500                    505                    510 | | 1536 |
| tcc tct tta tgt atc aga cat ggc att cat agt gaa gga gaa agg tac<br>Ser Ser Leu Cys Ile Arg His Gly Ile His Ser Glu Gly Glu Arg Tyr<br>                    515                    520                    525 | | 1584 |
| ctc tca tca ctt gat ctt tct aac ttg aag ttg agg tca att atg ttc<br>Leu Ser Ser Leu Asp Leu Ser Asn Leu Lys Leu Arg Ser Ile Met Phe<br>530                    535                    540 | | 1632 |
| ttc gat cca tat att tgt aat gtg ttc caa cat ata gat gtg ttt cga<br>Phe Asp Pro Tyr Ile Cys Asn Val Phe Gln His Ile Asp Val Phe Arg<br>545                    550                    555                    560 | | 1680 |
| cat cta tat gtg ttg tac ttg gat acg aat ttt ggg tat gtg tct atg<br>His Leu Tyr Val Leu Tyr Leu Asp Thr Asn Phe Gly Tyr Val Ser Met<br>                    565                    570                    575 | | 1728 |
| gta cct gat gcc ata gga agt ttg tac cac ctc aag ttg tta aga ttg<br>Val Pro Asp Ala Ile Gly Ser Leu Tyr His Leu Lys Leu Leu Arg Leu<br>580                    585                    590 | | 1776 |
| aga ggt atc cat gat att ccg tct tcc att ggc aac ctc aag aat tta<br>Arg Gly Ile His Asp Ile Pro Ser Ser Ile Gly Asn Leu Lys Asn Leu<br>595                    600                    605 | | 1824 |
| caa aca ctt gtc gtt gta aat ggt tac aca ttt ttt tgc gaa cta ccc<br>Gln Thr Leu Val Val Val Asn Gly Tyr Thr Phe Phe Cys Glu Leu Pro<br>610                    615                    620 | | 1872 |
| tgc aag aca gct gac cta ata aat cta aga cat tta gtt gtt caa tat<br>Cys Lys Thr Ala Asp Leu Ile Asn Leu Arg His Leu Val Val Gln Tyr<br>625                    630                    635                    640 | | 1920 |
| aca gag cct tta aaa tgt ata aac aaa ctc act agt ctt caa gtt ctt<br>Thr Glu Pro Leu Lys Cys Ile Asn Lys Leu Thr Ser Leu Gln Val Leu<br>                    645                    650                    655 | | 1968 |
| gat ggt gtt gct tgt gat cag tgg aaa gat gtt gac cct gtt gat tta<br>Asp Gly Val Ala Cys Asp Gln Trp Lys Asp Val Asp Pro Val Asp Leu<br>660                    665                    670 | | 2016 |
| gtc aat ctt cga gaa tta agc atg gat cgt atc agg agc tct tac tcc<br>Val Asn Leu Arg Glu Leu Ser Met Asp Arg Ile Arg Ser Ser Tyr Ser<br>675                    680                    685 | | 2064 |
| cta aac aac att agc agc ttg aaa aac ctt agc act ctc aaa ttg att<br>Leu Asn Asn Ile Ser Ser Leu Lys Asn Leu Ser Thr Leu Lys Leu Ile<br>690                    695                    700 | | 2112 |
| tgt gga gaa cgt caa tca ttt gca tcc ctt gaa ttt gtt aat tgt tgt<br>Cys Gly Glu Arg Gln Ser Phe Ala Ser Leu Glu Phe Val Asn Cys Cys<br>705                    710                    715                    720 | | 2160 |
| gaa aag ctc cag aaa ttg tgg tta caa ggg aga ata gag gaa ctg cct<br>Glu Lys Leu Gln Lys Leu Trp Leu Gln Gly Arg Ile Glu Glu Leu Pro<br>                    725                    730                    735 | | 2208 |
| cat ctg ttt tca aac tcc atc aca atg atg gtt ctg agt ttc tca gaa<br>His Leu Phe Ser Asn Ser Ile Thr Met Met Val Leu Ser Phe Ser Glu<br>740                    745                    750 | | 2256 |

```
ctg aca gaa gat ccg atg cct att ttg gga agg ttt cca aac cta agg   2304
Leu Thr Glu Asp Pro Met Pro Ile Leu Gly Arg Phe Pro Asn Leu Arg
        755                 760                 765 aat ctc aaa tta gat gga gct tac gaa gga aaa gaa ata atg tgc agt   2352
Asn Leu Lys Leu Asp Gly Ala Tyr Glu Gly Lys Glu Ile Met Cys Ser
770                 775                 780 gat aac agc ttc agt caa cta gag ttc ctt cat ctt cgt gat ctt tgg   2400
Asp Asn Ser Phe Ser Gln Leu Glu Phe Leu His Leu Arg Asp Leu Trp
785                 790                 795                 800 aag cta gaa aga tgg gat tta ggc aca agt gcc atg cct ctg att aaa   2448
Lys Leu Glu Arg Trp Asp Leu Gly Thr Ser Ala Met Pro Leu Ile Lys
                805                 810                 815 ggt ctt ggt atc cat aac tgt cca aat tta aag gag att cct gag aga   2496
Gly Leu Gly Ile His Asn Cys Pro Asn Leu Lys Glu Ile Pro Glu Arg
                820                 825                 830 atg aaa gac gtg gag ctg ttg aag cgg aat tat atg ttg tga           2538
Met Lys Asp Val Glu Leu Leu Lys Arg Asn Tyr Met Leu
            835                 840                 845

<210> SEQ ID NO 37
<211> LENGTH: 845
<212> TYPE: PRT
<213> ORGANISM: Solanum bulbocastanum

<400> SEQUENCE: 37

Met Ala Asp Ala Phe Leu Ser Phe Ala Val Gln Lys Leu Gly Asp Phe
1               5                   10                  15

Leu Ile Gln Lys Val Ser Leu Arg Lys Ser Leu Arg Asp Glu Ile Arg
            20                  25                  30

Trp Leu Ile Asn Glu Leu Leu Phe Ile Arg Ser Phe Leu Arg Asp Ala
        35                  40                  45

Glu Gln Lys Gln Cys Gly Asp Gln Arg Val Gln Gln Trp Val Phe Glu
    50                  55                  60

Ile Asn Ser Ile Ala Asn Asp Ala Val Ala Ile Leu Glu Thr Tyr Ser
65                  70                  75                  80

Phe Glu Ala Gly Lys Gly Ala Ser Arg Leu Lys Ala Cys Thr Cys Ile
                85                  90                  95

Cys Arg Lys Glu Lys Phe Tyr Asn Val Ala Glu Glu Ile Gln Ser
            100                 105                 110

Leu Lys Gln Arg Ile Met Asp Ile Ser Arg Lys Arg Glu Thr Tyr Gly
        115                 120                 125

Ile Thr Asn Ile Asn Asn Ala Gly Glu Gly Pro Ser Asn Gln Val
    130                 135                 140

Thr Lys Leu Arg Arg Thr Thr Ser Tyr Val Asp Glu Gln Asp Tyr Ile
145                 150                 155                 160

Phe Val Gly Phe Gln Asp Val Val Gln Thr Phe Leu Ala Gln Leu Leu
                165                 170                 175

Lys Ala Glu Pro Arg Arg Ser Val Leu Ser Ile Tyr Gly Met Gly Gly
            180                 185                 190

Leu Gly Lys Thr Thr Leu Ala Arg Lys Leu Tyr Thr Ser Pro Asp Ile
        195                 200                 205

Leu Asn Ser Phe Arg Thr Arg Ala Trp Ile Cys Val Ser Gln Glu Tyr
    210                 215                 220

Asn Thr Met Asp Leu Leu Arg Asn Ile Ile Lys Ser Ile Gln Gly Arg
225                 230                 235                 240

Thr Lys Glu Thr Leu Asp Leu Leu Glu Arg Met Thr Glu Gly Asp Leu
                245                 250                 255
```

```
Glu Ile Tyr Leu Arg Asp Leu Leu Lys Glu Arg Lys Tyr Leu Val Val
            260                 265                 270

Val Asp Asp Val Trp Gln Arg Glu Ala Trp Glu Ser Leu Lys Arg Ser
        275                 280                 285

Phe Pro Asp Gly Lys Asn Gly Ser Arg Val Ile Ile Thr Thr Arg Lys
    290                 295                 300

Glu Asp Val Ala Glu Arg Ala Asp Asp Arg Gly Phe Val His Lys Leu
305                 310                 315                 320

Arg Phe Leu Ser Gln Glu Ser Trp Asp Leu Phe Arg Arg Lys Leu
            325                 330                 335

Leu Asp Val Arg Ala Met Val Pro Glu Met Glu Ser Leu Ala Lys Asp
            340                 345                 350

Met Val Glu Lys Cys Arg Gly Leu Pro Leu Ala Ile Val Val Leu Ser
        355                 360                 365

Gly Leu Leu Ser His Lys Lys Gly Leu Asn Gln Trp Gln Lys Val Lys
    370                 375                 380

Asp His Leu Trp Lys Asn Ile Lys Glu Asp Lys Ser Ile Glu Ile Ser
385                 390                 395                 400

Asn Ile Leu Ser Leu Ser Tyr Asn Asp Leu Ser Thr Ala Leu Lys Gln
            405                 410                 415

Cys Phe Leu Tyr Phe Gly Ile Phe Pro Glu Asp Gln Val Val Lys Ala
            420                 425                 430

Asp Asp Ile Ile Arg Leu Trp Met Ala Glu Gly Phe Ile Pro Arg Gly
        435                 440                 445

Glu Glu Arg Met Glu Asp Val Ala Asp Gly Phe Leu Asn Glu Leu Ile
    450                 455                 460

Arg Arg Ser Leu Val Gln Val Ala Lys Thr Phe Trp Glu Lys Val Thr
465                 470                 475                 480

Asp Cys Arg Val His Asp Leu Leu Arg Asp Leu Ala Ile Gln Lys Ala
            485                 490                 495

Leu Glu Val Asn Phe Phe Asp Ile Tyr Asp Pro Arg Ser His Ser Ile
            500                 505                 510

Ser Ser Leu Cys Ile Arg His Gly Ile His Ser Glu Gly Glu Arg Tyr
        515                 520                 525

Leu Ser Ser Leu Asp Leu Ser Asn Leu Lys Leu Arg Ser Ile Met Phe
    530                 535                 540

Phe Asp Pro Tyr Ile Cys Asn Val Phe Gln His Ile Asp Val Phe Arg
545                 550                 555                 560

His Leu Tyr Val Leu Tyr Leu Asp Thr Asn Phe Gly Tyr Val Ser Met
            565                 570                 575

Val Pro Asp Ala Ile Gly Ser Leu Tyr His Leu Lys Leu Leu Arg Leu
            580                 585                 590

Arg Gly Ile His Asp Ile Pro Ser Ser Ile Gly Asn Leu Lys Asn Leu
        595                 600                 605

Gln Thr Leu Val Val Val Asn Gly Tyr Thr Phe Phe Cys Glu Leu Pro
    610                 615                 620

Cys Lys Thr Ala Asp Leu Ile Asn Leu Arg His Leu Val Gln Tyr
625                 630                 635                 640

Thr Glu Pro Leu Lys Cys Ile Asn Lys Leu Thr Ser Leu Gln Val Leu
            645                 650                 655

Asp Gly Val Ala Cys Asp Gln Trp Lys Asp Val Asp Pro Val Asp Leu
            660                 665                 670

Val Asn Leu Arg Glu Leu Ser Met Asp Arg Ile Arg Ser Ser Tyr Ser
        675                 680                 685
```

-continued

```
Leu Asn Asn Ile Ser Ser Leu Lys Asn Leu Ser Thr Leu Lys Leu Ile
        690                 695                 700

Cys Gly Glu Arg Gln Ser Phe Ala Ser Leu Glu Phe Val Asn Cys Cys
705                 710                 715                 720

Glu Lys Leu Gln Lys Leu Trp Leu Gln Gly Arg Ile Glu Glu Leu Pro
                725                 730                 735

His Leu Phe Ser Asn Ser Ile Thr Met Met Val Leu Ser Phe Ser Glu
            740                 745                 750

Leu Thr Glu Asp Pro Met Pro Ile Leu Gly Arg Phe Pro Asn Leu Arg
        755                 760                 765

Asn Leu Lys Leu Asp Gly Ala Tyr Glu Gly Lys Glu Ile Met Cys Ser
770                 775                 780

Asp Asn Ser Phe Ser Gln Leu Glu Phe Leu His Leu Arg Asp Leu Trp
785                 790                 795                 800

Lys Leu Glu Arg Trp Asp Leu Gly Thr Ser Ala Met Pro Leu Ile Lys
                805                 810                 815

Gly Leu Gly Ile His Asn Cys Pro Asn Leu Lys Glu Ile Pro Glu Arg
            820                 825                 830

Met Lys Asp Val Glu Leu Leu Lys Arg Asn Tyr Met Leu
        835                 840                 845

<210> SEQ ID NO 38
<211> LENGTH: 2538
<212> TYPE: DNA
<213> ORGANISM: Solanum demissum
<220> FEATURE:
<221> NAME/KEY: CDS
<222> LOCATION: (1)..(2538)

<400> SEQUENCE: 38 atg gct gat gcc ttt cta tca ttt gca gtt caa aaa ttg ggt gat ttc      48
Met Ala Asp Ala Phe Leu Ser Phe Ala Val Gln Lys Leu Gly Asp Phe
1               5                   10                  15 ctc att caa caa gtt tct ctg cgt aaa aat ctg aga aag gaa att gag      96
Leu Ile Gln Gln Val Ser Leu Arg Lys Asn Leu Arg Lys Glu Ile Glu
            20                  25                  30 tgg ctg aga aat gag cta ctc ttc ata cag tct ttc ctc aga gat gca     144
Trp Leu Arg Asn Glu Leu Leu Phe Ile Gln Ser Phe Leu Arg Asp Ala
        35                  40                  45 gaa cta aag caa tat gga gat caa aga gtt caa caa tgg gtg ttt gag     192
Glu Leu Lys Gln Tyr Gly Asp Gln Arg Val Gln Gln Trp Val Phe Glu
    50                  55                  60 atc aac tct att gct aat gat gtt gtt gct ata ctc gag act tac acc     240
Ile Asn Ser Ile Ala Asn Asp Val Val Ala Ile Leu Glu Thr Tyr Thr
65                  70                  75                  80 ttc gag gct ggt aaa ggt gct agt cgt ctc aag gct tgc gct tgc ata     288
Phe Glu Ala Gly Lys Gly Ala Ser Arg Leu Lys Ala Cys Ala Cys Ile
                85                  90                  95 tat acg aag gag aag aaa ttc tac aat gtt gcc gag gag atc caa tca     336
Tyr Thr Lys Glu Lys Lys Phe Tyr Asn Val Ala Glu Glu Ile Gln Ser
            100                 105                 110 ctc aag caa cga atc atg gat atc tct cgc aaa cga gag act tat ggt     384
Leu Lys Gln Arg Ile Met Asp Ile Ser Arg Lys Arg Glu Thr Tyr Gly
        115                 120                 125 att aca aat atc aat aat aat tca gga gaa ggg cca agt aat cag gtt     432
Ile Thr Asn Ile Asn Asn Asn Ser Gly Glu Gly Pro Ser Asn Gln Val
    130                 135                 140 aga aca ttg agg aga act acc tca tat gtg gat gac cag gat tac att     480
Arg Thr Leu Arg Arg Thr Thr Ser Tyr Val Asp Asp Gln Asp Tyr Ile
145                 150                 155                 160
```

```
ttt gtt gga ctt cag gat gtt gta caa aaa ttg cta gct caa ctt ctc    528
Phe Val Gly Leu Gln Asp Val Val Gln Lys Leu Leu Ala Gln Leu Leu
                165                 170                 175 aaa gca gag ccc cgt cga acc gtc ctc tcc att cat ggc atg ggc gga    576
Lys Ala Glu Pro Arg Arg Thr Val Leu Ser Ile His Gly Met Gly Gly
            180                 185                 190 ttg ggc aag acc act ctt gcg aga aaa ctt tac aac agt tct gct ata    624
Leu Gly Lys Thr Thr Leu Ala Arg Lys Leu Tyr Asn Ser Ser Ala Ile
        195                 200                 205 ctc aat agc ttc cct aca cgc gct tgg ata tgt gtc tct caa gag tac    672
Leu Asn Ser Phe Pro Thr Arg Ala Trp Ile Cys Val Ser Gln Glu Tyr
    210                 215                 220 aac aca atg gat ctt ctt agg aat atc ata aaa tcc gtc caa ggt cgc    720
Asn Thr Met Asp Leu Leu Arg Asn Ile Ile Lys Ser Val Gln Gly Arg
225                 230                 235                 240 acc aag gaa act cta gat ttg ttg gaa agg atg aca gaa gga gat cta    768
Thr Lys Glu Thr Leu Asp Leu Leu Glu Arg Met Thr Glu Gly Asp Leu
                245                 250                 255 gaa atc tat ctt cgt gat cta tta aaa gaa cgc aaa tac ctt gtg atg    816
Glu Ile Tyr Leu Arg Asp Leu Leu Lys Glu Arg Lys Tyr Leu Val Met
            260                 265                 270 gtt gat gat gta tgg cag aaa gaa gca tgg gat agt ttg aag aga gca    864
Val Asp Asp Val Trp Gln Lys Glu Ala Trp Asp Ser Leu Lys Arg Ala
        275                 280                 285 ttc ccg gat agc aag aat ggc agc aga gtc att att acc acg cgc aaa    912
Phe Pro Asp Ser Lys Asn Gly Ser Arg Val Ile Ile Thr Thr Arg Lys
    290                 295                 300 cag gat gtc gct gaa aga gca gac gac ata ggt ttt gtt cat aaa ctt    960
Gln Asp Val Ala Glu Arg Ala Asp Asp Ile Gly Phe Val His Lys Leu
305                 310                 315                 320 cgt ttc cta agt caa gaa gaa agt tgg gat ctc ttt cgt aag aaa cta    1008
Arg Phe Leu Ser Gln Glu Glu Ser Trp Asp Leu Phe Arg Lys Lys Leu
                325                 330                 335 ctt gat gtt cga tca atg gtt cca gaa atg gaa aat cta gct aag gat    1056
Leu Asp Val Arg Ser Met Val Pro Glu Met Glu Asn Leu Ala Lys Asp
            340                 345                 350 atg gtg gaa aag tgt aga ggc tta cct ctt gca att gtt gta ttg agc    1104
Met Val Glu Lys Cys Arg Gly Leu Pro Leu Ala Ile Val Val Leu Ser
        355                 360                 365 gga cta ctt tcg cat aaa aag ggg cta aac caa tgg caa aag gtg aaa    1152
Gly Leu Leu Ser His Lys Lys Gly Leu Asn Gln Trp Gln Lys Val Lys
    370                 375                 380 gat cac ctt tgg aag aac att aaa gaa gat aaa tct att gaa atc tct    1200
Asp His Leu Trp Lys Asn Ile Lys Glu Asp Lys Ser Ile Glu Ile Ser
385                 390                 395                 400 aac ata cta tcc tta agc tac aat gat ttg tca act gcg ctc aag cag    1248
Asn Ile Leu Ser Leu Ser Tyr Asn Asp Leu Ser Thr Ala Leu Lys Gln
                405                 410                 415 tgt ttt ctc tac ttt ggt att ttt cca gaa gat caa gtg gta aag gct    1296
Cys Phe Leu Tyr Phe Gly Ile Phe Pro Glu Asp Gln Val Val Lys Ala
            420                 425                 430 gat gac ata ata cgg ttg tgg atg gcg gag ggt ttc ata ccc aga gga    1344
Asp Asp Ile Ile Arg Leu Trp Met Ala Glu Gly Phe Ile Pro Arg Gly
        435                 440                 445 gaa gaa aga atg gag gat gtg gct gac ggc ttc tta aat gaa ctg ata    1392
Glu Glu Arg Met Glu Asp Val Ala Asp Gly Phe Leu Asn Glu Leu Ile
    450                 455                 460 aga cga agc ttg gtt caa gta gct aaa aca ttt tgg gaa aaa gtt act    1440
Arg Arg Ser Leu Val Gln Val Ala Lys Thr Phe Trp Glu Lys Val Thr
465                 470                 475                 480
```

```
gac tgt agg gtt cat gat tta ctt cgt gat ctt gcg ata caa aag gta      1488
Asp Cys Arg Val His Asp Leu Leu Arg Asp Leu Ala Ile Gln Lys Val
            485                 490                 495 ttg gag gta aac ttc ttt gac att tat gat cca aga agc cac tcc ata      1536
Leu Glu Val Asn Phe Phe Asp Ile Tyr Asp Pro Arg Ser His Ser Ile
        500                 505                 510 tcc tct tta tgt atc aga cat ggc att cat agt gaa gga gaa agg tac      1584
Ser Ser Leu Cys Ile Arg His Gly Ile His Ser Glu Gly Glu Arg Tyr
            515                 520                 525 ctc tca tca ctt gat ctt tct aac ttg aag ttg agg tca att atg ttc      1632
Leu Ser Ser Leu Asp Leu Ser Asn Leu Lys Leu Arg Ser Ile Met Phe
        530                 535                 540 ttc gat cca tat att tgt aat gtg ttc caa cat ata gat gtg ttt cga      1680
Phe Asp Pro Tyr Ile Cys Asn Val Phe Gln His Ile Asp Val Phe Arg
545                 550                 555                 560 cat cta tat gtg ttg tac ttg gat acg aat ttt ggg tat gtg tct atg      1728
His Leu Tyr Val Leu Tyr Leu Asp Thr Asn Phe Gly Tyr Val Ser Met
            565                 570                 575 gta cct gat gcc ata gga agt ttg tac cac ctc aag ttg tta aga ttg      1776
Val Pro Asp Ala Ile Gly Ser Leu Tyr His Leu Lys Leu Leu Arg Leu
        580                 585                 590 aga ggt atc cat gat att ccg tct tcc att ggc aac ctc aag aat tta      1824
Arg Gly Ile His Asp Ile Pro Ser Ser Ile Gly Asn Leu Lys Asn Leu
            595                 600                 605 caa aca ctt gtc gtt gta aat ggt tac aca ttt ttt tgc gaa cta ccc      1872
Gln Thr Leu Val Val Val Asn Gly Tyr Thr Phe Phe Cys Glu Leu Pro
        610                 615                 620 tgc aag aca gct gac cta ata aat cta aga cat tta gtt gtt caa tat      1920
Cys Lys Thr Ala Asp Leu Ile Asn Leu Arg His Leu Val Val Gln Tyr
625                 630                 635                 640 aca gag cct tta aaa tgt ata aac aaa ctc act agt ctt caa gtt ctt      1968
Thr Glu Pro Leu Lys Cys Ile Asn Lys Leu Thr Ser Leu Gln Val Leu
            645                 650                 655 gat ggt gtt gct tgt gat cag tgg aaa gat gtt gac cct gtt gat tta      2016
Asp Gly Val Ala Cys Asp Gln Trp Lys Asp Val Asp Pro Val Asp Leu
        660                 665                 670 gtc aat ctt cga gaa tta agc atg gat cgt atc agg agc tct tac tcc      2064
Val Asn Leu Arg Glu Leu Ser Met Asp Arg Ile Arg Ser Ser Tyr Ser
            675                 680                 685 cta aac aac att agc agc ttg aaa aac ctt agc act ctc aaa ttg att      2112
Leu Asn Asn Ile Ser Ser Leu Lys Asn Leu Ser Thr Leu Lys Leu Ile
        690                 695                 700 tgt gga gaa cgt caa tca ttt gca tcc ctt gaa ttt gtt aat tgt tgt      2160
Cys Gly Glu Arg Gln Ser Phe Ala Ser Leu Glu Phe Val Asn Cys Cys
705                 710                 715                 720 gaa aag ctc cag aaa ttg tgg tta caa ggg aga ata gag gaa ctg cct      2208
Glu Lys Leu Gln Lys Leu Trp Leu Gln Gly Arg Ile Glu Glu Leu Pro
            725                 730                 735 cat ctg ttt tca aac tcc atc aca atg atg gtt ctg agt ttc tca gaa      2256
His Leu Phe Ser Asn Ser Ile Thr Met Met Val Leu Ser Phe Ser Glu
        740                 745                 750 ctg aca gaa gat ccg atg cct att ttg gga agg ttt cca aac cta agg      2304
Leu Thr Glu Asp Pro Met Pro Ile Leu Gly Arg Phe Pro Asn Leu Arg
            755                 760                 765 aat ctc aaa tta gat gga gct tac gaa gga aaa gaa ata atg tgc agt      2352
Asn Leu Lys Leu Asp Gly Ala Tyr Glu Gly Lys Glu Ile Met Cys Ser
        770                 775                 780 gat aac agc ttc agt caa cta gag ttc ctt cat ctt cgt gat ctt tgg      2400
Asp Asn Ser Phe Ser Gln Leu Glu Phe Leu His Leu Arg Asp Leu Trp
785                 790                 795                 800
```

```
aag cta gaa aga tgg gat tta ggc aca agt gcc atg cct ctg att aaa    2448
Lys Leu Glu Arg Trp Asp Leu Gly Thr Ser Ala Met Pro Leu Ile Lys
            805                 810                 815 ggt ctt ggt atc cat aac tgt cca aat tta aag gag att cct gag aga    2496
Gly Leu Gly Ile His Asn Cys Pro Asn Leu Lys Glu Ile Pro Glu Arg
        820                 825                 830 atg aaa gac gtg gag ctg ttg aag cgg aat tat atg ttg tga            2538
Met Lys Asp Val Glu Leu Leu Lys Arg Asn Tyr Met Leu
    835                 840                 845
```

<210> SEQ ID NO 39
<211> LENGTH: 845
<212> TYPE: PRT
<213> ORGANISM: Solanum demissum

<400> SEQUENCE: 39

```
Met Ala Asp Ala Phe Leu Ser Phe Ala Val Gln Lys Leu Gly Asp Phe
1               5                   10                  15

Leu Ile Gln Gln Val Ser Leu Arg Lys Asn Leu Arg Lys Glu Ile Glu
            20                  25                  30

Trp Leu Arg Asn Glu Leu Leu Phe Ile Gln Ser Phe Leu Arg Asp Ala
        35                  40                  45

Glu Leu Lys Gln Tyr Gly Asp Gln Arg Val Gln Gln Trp Val Phe Glu
    50                  55                  60

Ile Asn Ser Ile Ala Asn Asp Val Val Ala Ile Leu Glu Thr Tyr Thr
65                  70                  75                  80

Phe Glu Ala Gly Lys Gly Ala Ser Arg Leu Lys Ala Cys Ala Cys Ile
                85                  90                  95

Tyr Thr Lys Glu Lys Lys Phe Tyr Asn Val Ala Glu Glu Ile Gln Ser
            100                 105                 110

Leu Lys Gln Arg Ile Met Asp Ile Ser Arg Lys Arg Glu Thr Tyr Gly
        115                 120                 125

Ile Thr Asn Ile Asn Asn Asn Ser Gly Glu Gly Pro Ser Asn Gln Val
    130                 135                 140

Arg Thr Leu Arg Arg Thr Thr Ser Tyr Val Asp Asp Gln Asp Tyr Ile
145                 150                 155                 160

Phe Val Gly Leu Gln Asp Val Val Gln Lys Leu Leu Ala Gln Leu Leu
                165                 170                 175

Lys Ala Glu Pro Arg Arg Thr Val Leu Ser Ile His Gly Met Gly Gly
            180                 185                 190

Leu Gly Lys Thr Thr Leu Ala Arg Lys Leu Tyr Asn Ser Ser Ala Ile
        195                 200                 205

Leu Asn Ser Phe Pro Thr Arg Ala Trp Ile Cys Val Ser Gln Glu Tyr
    210                 215                 220

Asn Thr Met Asp Leu Leu Arg Asn Ile Ile Lys Ser Val Gln Gly Arg
225                 230                 235                 240

Thr Lys Glu Thr Leu Asp Leu Leu Glu Arg Met Thr Glu Gly Asp Leu
                245                 250                 255

Glu Ile Tyr Leu Arg Asp Leu Leu Lys Glu Arg Lys Tyr Leu Val Met
            260                 265                 270

Val Asp Asp Val Trp Gln Lys Glu Ala Trp Ser Leu Lys Arg Ala
        275                 280                 285

Phe Pro Asp Ser Lys Asn Gly Ser Arg Val Ile Ile Thr Thr Arg Lys
    290                 295                 300

Gln Asp Val Ala Glu Arg Ala Asp Ile Gly Phe Val His Lys Leu
305                 310                 315                 320
```

-continued

```
Arg Phe Leu Ser Gln Glu Ser Trp Asp Leu Phe Arg Lys Lys Leu
            325                 330                 335

Leu Asp Val Arg Ser Met Val Pro Glu Met Glu Asn Leu Ala Lys Asp
        340                 345                 350

Met Val Glu Lys Cys Arg Gly Leu Pro Leu Ala Ile Val Val Leu Ser
            355                 360                 365

Gly Leu Leu Ser His Lys Lys Gly Leu Asn Gln Trp Gln Lys Val Lys
    370                 375                 380

Asp His Leu Trp Lys Asn Ile Lys Glu Asp Lys Ser Ile Glu Ile Ser
385                 390                 395                 400

Asn Ile Leu Ser Leu Ser Tyr Asn Asp Leu Ser Thr Ala Leu Lys Gln
            405                 410                 415

Cys Phe Leu Tyr Phe Gly Ile Phe Pro Glu Asp Gln Val Val Lys Ala
            420                 425                 430

Asp Asp Ile Ile Arg Leu Trp Met Ala Glu Gly Phe Ile Pro Arg Gly
            435                 440                 445

Glu Glu Arg Met Glu Asp Val Ala Asp Gly Phe Leu Asn Glu Leu Ile
    450                 455                 460

Arg Arg Ser Leu Val Gln Val Ala Lys Thr Phe Trp Glu Lys Val Thr
465                 470                 475                 480

Asp Cys Arg Val His Asp Leu Leu Arg Asp Leu Ala Ile Gln Lys Val
            485                 490                 495

Leu Glu Val Asn Phe Phe Asp Ile Tyr Asp Pro Arg Ser His Ser Ile
            500                 505                 510

Ser Ser Leu Cys Ile Arg His Gly Ile His Ser Glu Gly Glu Arg Tyr
            515                 520                 525

Leu Ser Ser Leu Asp Leu Ser Asn Leu Lys Leu Arg Ser Ile Met Phe
    530                 535                 540

Phe Asp Pro Tyr Ile Cys Asn Val Phe Gln His Ile Asp Val Phe Arg
545                 550                 555                 560

His Leu Tyr Val Leu Tyr Leu Asp Thr Asn Phe Gly Tyr Val Ser Met
            565                 570                 575

Val Pro Asp Ala Ile Gly Ser Leu Tyr His Leu Lys Leu Leu Arg Leu
            580                 585                 590

Arg Gly Ile His Asp Ile Pro Ser Ser Ile Gly Asn Leu Lys Asn Leu
    595                 600                 605

Gln Thr Leu Val Val Val Asn Gly Tyr Thr Phe Phe Cys Glu Leu Pro
    610                 615                 620

Cys Lys Thr Ala Asp Leu Ile Asn Leu Arg His Leu Val Val Gln Tyr
625                 630                 635                 640

Thr Glu Pro Leu Lys Cys Ile Asn Lys Leu Thr Ser Leu Gln Val Leu
            645                 650                 655

Asp Gly Val Ala Cys Asp Gln Trp Lys Asp Val Asp Pro Val Asp Leu
        660                 665                 670

Val Asn Leu Arg Glu Leu Ser Met Asp Arg Ile Arg Ser Ser Tyr Ser
    675                 680                 685

Leu Asn Asn Ile Ser Ser Leu Lys Asn Leu Ser Thr Leu Lys Leu Ile
    690                 695                 700

Cys Gly Glu Arg Gln Ser Phe Ala Ser Leu Glu Phe Val Asn Cys Cys
705                 710                 715                 720

Glu Lys Leu Gln Lys Leu Trp Leu Gln Gly Arg Ile Glu Glu Leu Pro
            725                 730                 735

His Leu Phe Ser Asn Ser Ile Thr Met Met Val Leu Ser Phe Ser Glu
            740                 745                 750
```

| | | | | | | | | | | | | |
|---|---|---|---|---|---|---|---|---|---|---|---|---|
| Leu | Thr | Glu | Asp | Pro | Met | Pro | Ile | Leu | Gly | Arg | Phe | Pro | Asn | Leu | Arg |
| | | 755 | | | 760 | | | | | 765 | | | | | |
| Asn | Leu | Lys | Leu | Asp | Gly | Ala | Tyr | Glu | Gly | Lys | Glu | Ile | Met | Cys | Ser |
| 770 | | | | | 775 | | | | | 780 | | | | | |
| Asp | Asn | Ser | Phe | Ser | Gln | Leu | Glu | Phe | Leu | His | Leu | Arg | Asp | Leu | Trp |
| 785 | | | | | 790 | | | | | 795 | | | | | 800 |
| Lys | Leu | Glu | Arg | Trp | Asp | Leu | Gly | Thr | Ser | Ala | Met | Pro | Leu | Ile | Lys |
| | | | | 805 | | | | | 810 | | | | | 815 | |
| Gly | Leu | Gly | Ile | His | Asn | Cys | Pro | Asn | Leu | Lys | Glu | Ile | Pro | Glu | Arg |
| | | | | 820 | | | | | 825 | | | | | 830 | |
| Met | Lys | Asp | Val | Glu | Leu | Leu | Lys | Arg | Asn | Tyr | Met | Leu | | | |
| | | | 835 | | | | | 840 | | | | 845 | | | |

<210> SEQ ID NO 40
<211> LENGTH: 2544
<212> TYPE: DNA
<213> ORGANISM: Solanum bulbocastanum
<220> FEATURE:
<221> NAME/KEY: CDS
<222> LOCATION: (1)..(2544)

<400> SEQUENCE: 40

| | | | | | | | | | | | | | | | | |
|---|---|---|---|---|---|---|---|---|---|---|---|---|---|---|---|---|
| atg | gct | gat | gcc | ttt | cta | tca | ttt | gca | gtt | caa | aaa | ttg | ggt | gat | ttc | 48 |
| Met | Ala | Asp | Ala | Phe | Leu | Ser | Phe | Ala | Val | Gln | Lys | Leu | Gly | Asp | Phe | |
| 1 | | | | 5 | | | | | 10 | | | | | 15 | | |
| cta | ata | cag | aaa | gtt | tcc | ctg | cgt | aaa | agt | ctc | aga | gat | gaa | att | aga | 96 |
| Leu | Ile | Gln | Lys | Val | Ser | Leu | Arg | Lys | Ser | Leu | Arg | Asp | Glu | Ile | Arg | |
| | | 20 | | | | | 25 | | | | | 30 | | | | |
| tgg | ctg | atc | aat | gag | cta | ctc | ttc | ata | cgg | tct | ttc | ctc | aga | gat | gca | 144 |
| Trp | Leu | Ile | Asn | Glu | Leu | Leu | Phe | Ile | Arg | Ser | Phe | Leu | Arg | Asp | Ala | |
| | | | 35 | | | | | 40 | | | | | 45 | | | |
| gaa | caa | aag | cag | tgc | gga | gat | caa | aga | gtt | caa | caa | tgg | gtg | ttt | gag | 192 |
| Glu | Gln | Lys | Gln | Cys | Gly | Asp | Gln | Arg | Val | Gln | Gln | Trp | Val | Phe | Glu | |
| | 50 | | | | | 55 | | | | | 60 | | | | | |
| atc | aac | tct | att | gct | aat | gat | gct | gtt | gct | ata | ctc | gag | act | tat | agc | 240 |
| Ile | Asn | Ser | Ile | Ala | Asn | Asp | Ala | Val | Ala | Ile | Leu | Glu | Thr | Tyr | Ser | |
| 65 | | | | | 70 | | | | | 75 | | | | | 80 | |
| ttt | gag | gct | ggt | aaa | ggt | gct | agt | cgt | ctc | aag | gct | tgc | act | tgc | ata | 288 |
| Phe | Glu | Ala | Gly | Lys | Gly | Ala | Ser | Arg | Leu | Lys | Ala | Cys | Thr | Cys | Ile | |
| | | | | 85 | | | | | 90 | | | | | 95 | | |
| tgt | agg | aag | gag | aag | aaa | ttc | tac | aat | gtt | gcc | gag | gag | att | caa | tca | 336 |
| Cys | Arg | Lys | Glu | Lys | Lys | Phe | Tyr | Asn | Val | Ala | Glu | Glu | Ile | Gln | Ser | |
| | | | 100 | | | | | 105 | | | | | 110 | | | |
| ctc | aag | caa | cga | atc | atg | gat | atc | tct | cgc | aaa | cga | gag | act | tat | ggt | 384 |
| Leu | Lys | Gln | Arg | Ile | Met | Asp | Ile | Ser | Arg | Lys | Arg | Glu | Thr | Tyr | Gly | |
| | | 115 | | | | | 120 | | | | | 125 | | | | |
| att | aca | aat | atc | aat | aat | aat | gca | gga | gaa | ggg | cca | agt | aat | cag | gtt | 432 |
| Ile | Thr | Asn | Ile | Asn | Asn | Asn | Ala | Gly | Glu | Gly | Pro | Ser | Asn | Gln | Val | |
| | 130 | | | | | 135 | | | | | 140 | | | | | |
| aca | aaa | ttg | agg | aga | act | acc | tca | tat | gta | gat | gaa | cag | gat | tac | att | 480 |
| Thr | Lys | Leu | Arg | Arg | Thr | Thr | Ser | Tyr | Val | Asp | Glu | Gln | Asp | Tyr | Ile | |
| 145 | | | | | 150 | | | | | 155 | | | | | 160 | |
| ttt | gtt | ggc | ttt | cag | gat | gtt | gta | caa | aca | ttt | cta | gct | caa | ctt | ctg | 528 |
| Phe | Val | Gly | Phe | Gln | Asp | Val | Val | Gln | Thr | Phe | Leu | Ala | Gln | Leu | Leu | |
| | | | | 165 | | | | | 170 | | | | | 175 | | |
| aaa | gca | gag | cct | cgt | cga | agc | gtc | ctc | tcc | att | tat | gga | atg | ggg | ggt | 576 |
| Lys | Ala | Glu | Pro | Arg | Arg | Ser | Val | Leu | Ser | Ile | Tyr | Gly | Met | Gly | Gly | |
| | | | 180 | | | | | 185 | | | | | 190 | | | |
| tta | ggc | aag | acc | act | ctt | gcc | aga | aaa | ctt | tac | acc | agt | cct | gat | ata | 624 |
| Leu | Gly | Lys | Thr | Thr | Leu | Ala | Arg | Lys | Leu | Tyr | Thr | Ser | Pro | Asp | Ile | |
| | | 195 | | | | | 200 | | | | | 205 | | | | |

```
ctc aat agc ttc cgt aca cgc gct tgg ata tgt gtc tct caa gag tac      672
Leu Asn Ser Phe Arg Thr Arg Ala Trp Ile Cys Val Ser Gln Glu Tyr
    210                 215                 220 aac aca atg gat ctt ctt agg aat atc ata aaa tcc atc caa ggt cgc      720
Asn Thr Met Asp Leu Leu Arg Asn Ile Ile Lys Ser Ile Gln Gly Arg
225                 230                 235                 240 acc aag gaa act cta gat ttg ttg gaa agg atg aca gaa gga gat ctt      768
Thr Lys Glu Thr Leu Asp Leu Leu Glu Arg Met Thr Glu Gly Asp Leu
            245                 250                 255 gaa att tat ctt cgt gat tta ttg aaa gaa cgc aaa tac ctt gtg gtg      816
Glu Ile Tyr Leu Arg Asp Leu Leu Lys Glu Arg Lys Tyr Leu Val Val
        260                 265                 270 gtt gat gat gta tgg cag aga gaa gca tgg gag agt ttg aaa aga tca      864
Val Asp Asp Val Trp Gln Arg Glu Ala Trp Glu Ser Leu Lys Arg Ser
    275                 280                 285 ttc ccg gat ggc aag aat ggc agc aga gtc att att acc acg cgc aaa      912
Phe Pro Asp Gly Lys Asn Gly Ser Arg Val Ile Ile Thr Thr Arg Lys
290                 295                 300 gag gat gtc gct gaa aga gca gac gac aga ggt ttt gtt cat aaa ctt      960
Glu Asp Val Ala Glu Arg Ala Asp Asp Arg Gly Phe Val His Lys Leu
305                 310                 315                 320 cgt ttc cta agc caa gaa gaa agt tgg gat ctc ttt cgt agg aaa cta     1008
Arg Phe Leu Ser Gln Glu Glu Ser Trp Asp Leu Phe Arg Arg Lys Leu
            325                 330                 335 ctt gat gtt cga gca atg gtt cca gaa atg gaa agt cta gct aag gat     1056
Leu Asp Val Arg Ala Met Val Pro Glu Met Glu Ser Leu Ala Lys Asp
        340                 345                 350 atg gtg gaa aag tgt aga ggc tta cct ctt gca att gtt gta ttg agc     1104
Met Val Glu Lys Cys Arg Gly Leu Pro Leu Ala Ile Val Val Leu Ser
    355                 360                 365 gga cta ctt tcg cat aaa aag ggg cta aac caa tgg caa aag gtg aaa     1152
Gly Leu Leu Ser His Lys Lys Gly Leu Asn Gln Trp Gln Lys Val Lys
370                 375                 380 gat cac ctt tgg aag aac att aaa gaa gat aaa tct att gaa atc tct     1200
Asp His Leu Trp Lys Asn Ile Lys Glu Asp Lys Ser Ile Glu Ile Ser
385                 390                 395                 400 aac ata cta tcc tta agc tac aat gat ttg tca act gcg ctc aag cag     1248
Asn Ile Leu Ser Leu Ser Tyr Asn Asp Leu Ser Thr Ala Leu Lys Gln
            405                 410                 415 tgt ttt ctc tac ttt ggt att ttt cca gaa gat caa gtg gta aag gct     1296
Cys Phe Leu Tyr Phe Gly Ile Phe Pro Glu Asp Gln Val Val Lys Ala
        420                 425                 430 gat gac ata ata cgg ttg tgg atg gcg gag ggt ttc ata ccc aga gga     1344
Asp Asp Ile Ile Arg Leu Trp Met Ala Glu Gly Phe Ile Pro Arg Gly
    435                 440                 445 gaa gaa aga atg gag gat gtg gct gac ggc ttc ttg aat gaa ctg ata     1392
Glu Glu Arg Met Glu Asp Val Ala Asp Gly Phe Leu Asn Glu Leu Ile
450                 455                 460 aga cga agc ttg gtt caa gta gct aaa aca ttt tgg gaa aaa gtt act     1440
Arg Arg Ser Leu Val Gln Val Ala Lys Thr Phe Trp Glu Lys Val Thr
465                 470                 475                 480 gac tgt agg gtt cat gat tta ctt cgt gat ctt gcg ata caa aag gca     1488
Asp Cys Arg Val His Asp Leu Leu Arg Asp Leu Ala Ile Gln Lys Ala
            485                 490                 495 ttg gag gta aac ttc ttt gac att tat gat cca aga agc cac tcc ata     1536
Leu Glu Val Asn Phe Phe Asp Ile Tyr Asp Pro Arg Ser His Ser Ile
        500                 505                 510 tcc tct tta tgt atc aga cat ggc att cat agt gaa gga gaa agg tac     1584
Ser Ser Leu Cys Ile Arg His Gly Ile His Ser Glu Gly Glu Arg Tyr
    515                 520                 525
```

```
ctc tca tca ctt gat ctt tct aac ttg aag ttg agg tca att atg ttc      1632
Leu Ser Ser Leu Asp Leu Ser Asn Leu Lys Leu Arg Ser Ile Met Phe
    530                 535                 540 ttc gat cca gat ttt cgt aag atg agt cat ata aac ctc agg agt gag      1680
Phe Asp Pro Asp Phe Arg Lys Met Ser His Ile Asn Leu Arg Ser Glu
545                 550                 555                 560 ttc caa cat cta tat gtg ttg tac ttg gat acg aat ttt ggg tat gtg      1728
Phe Gln His Leu Tyr Val Leu Tyr Leu Asp Thr Asn Phe Gly Tyr Val
                565                 570                 575 tct atg gta cct gat gcc ata gga agt ttg tac cac ctc aag ttg tta      1776
Ser Met Val Pro Asp Ala Ile Gly Ser Leu Tyr His Leu Lys Leu Leu
            580                 585                 590 aga ttg aga ggt atc cat gat att ccg tct tcc att ggc aac ctc aag      1824
Arg Leu Arg Gly Ile His Asp Ile Pro Ser Ser Ile Gly Asn Leu Lys
        595                 600                 605 aat tta caa aca ctt gtc gtt gta aat ggt tac aca ttt ttt tgc gaa      1872
Asn Leu Gln Thr Leu Val Val Val Asn Gly Tyr Thr Phe Phe Cys Glu
    610                 615                 620 cta ccc tgc aag aca gct gac cta ata aat cta aga cat tta gtt gtt      1920
Leu Pro Cys Lys Thr Ala Asp Leu Ile Asn Leu Arg His Leu Val Val
625                 630                 635                 640 caa tat aca gag cct tta aaa tgt ata aac aaa ctc act agt ctt caa      1968
Gln Tyr Thr Glu Pro Leu Lys Cys Ile Asn Lys Leu Thr Ser Leu Gln
                645                 650                 655 gtt ctt gat ggt gtt gct tgt gat cag tgg aaa gat gtt gac cct gtt      2016
Val Leu Asp Gly Val Ala Cys Asp Gln Trp Lys Asp Val Asp Pro Val
            660                 665                 670 gat tta gtc aat ctt cga gaa tta agc atg gat cgt atc agg agc tct      2064
Asp Leu Val Asn Leu Arg Glu Leu Ser Met Asp Arg Ile Arg Ser Ser
        675                 680                 685 tac tcc cta aac aac att agc agc ttg aaa aac ctt agc act ctc aaa      2112
Tyr Ser Leu Asn Asn Ile Ser Ser Leu Lys Asn Leu Ser Thr Leu Lys
    690                 695                 700 ttg att tgt gga gaa cgt caa tca ttt gca tcc ctt gaa ttt gtt aat      2160
Leu Ile Cys Gly Glu Arg Gln Ser Phe Ala Ser Leu Glu Phe Val Asn
705                 710                 715                 720 tgt tgt gaa aag ctc cag aaa ttg tgg tta caa ggg aga ata gag gaa      2208
Cys Cys Glu Lys Leu Gln Lys Leu Trp Leu Gln Gly Arg Ile Glu Glu
                725                 730                 735 ctg cct cat ctg ttt tca aac tcc atc aca atg atg gtt ctg agt ttc      2256
Leu Pro His Leu Phe Ser Asn Ser Ile Thr Met Met Val Leu Ser Phe
            740                 745                 750 tca gaa ctg aca gaa gat ccg atg cct att ttg gga agg ttt cca aac      2304
Ser Glu Leu Thr Glu Asp Pro Met Pro Ile Leu Gly Arg Phe Pro Asn
        755                 760                 765 cta agg aat ctc aaa tta gat gga gct tac gaa gga aaa gaa ata atg      2352
Leu Arg Asn Leu Lys Leu Asp Gly Ala Tyr Glu Gly Lys Glu Ile Met
    770                 775                 780 tgc agt gat aac agc ttc agt caa cta gag ttc ctt cat ctt cgt gat      2400
Cys Ser Asp Asn Ser Phe Ser Gln Leu Glu Phe Leu His Leu Arg Asp
785                 790                 795                 800 ctt tgg aag cta gaa aga tgg gat tta ggc aca agt gcg atg cct ctg      2448
Leu Trp Lys Leu Glu Arg Trp Asp Leu Gly Thr Ser Ala Met Pro Leu
                805                 810                 815 att aaa ggt ctt ggt atc cat aac tgt cca aat tta aag gag att cct      2496
Ile Lys Gly Leu Gly Ile His Asn Cys Pro Asn Leu Lys Glu Ile Pro
            820                 825                 830 gag aga atg aaa gac gtg gag ctg ttg aag cgg aat tat atg ttg tga      2544
Glu Arg Met Lys Asp Val Glu Leu Leu Lys Arg Asn Tyr Met Leu
        835                 840                 845
```

-continued

```
<210> SEQ ID NO 41
<211> LENGTH: 847
<212> TYPE: PRT
<213> ORGANISM: Solanum bulbocastanum

<400> SEQUENCE: 41
```

| | | | | | | | | | | | | | | |
|---|---|---|---|---|---|---|---|---|---|---|---|---|---|---|
| Met | Ala | Asp | Ala | Phe | Leu | Ser | Phe | Ala | Val | Gln | Lys | Leu | Gly | Asp | Phe |
| 1 | | | | 5 | | | | | 10 | | | | | 15 | |
| Leu | Ile | Gln | Lys | Val | Ser | Leu | Arg | Lys | Ser | Leu | Arg | Asp | Glu | Ile | Arg |
| | | | 20 | | | | | 25 | | | | | 30 | | |
| Trp | Leu | Ile | Asn | Glu | Leu | Leu | Phe | Ile | Arg | Ser | Phe | Leu | Arg | Asp | Ala |
| | | 35 | | | | | 40 | | | | | 45 | | | |
| Glu | Gln | Lys | Gln | Cys | Gly | Asp | Gln | Arg | Val | Gln | Gln | Trp | Val | Phe | Glu |
| | 50 | | | | | 55 | | | | | 60 | | | | |
| Ile | Asn | Ser | Ile | Ala | Asn | Asp | Ala | Val | Ala | Ile | Leu | Glu | Thr | Tyr | Ser |
| 65 | | | | | 70 | | | | | 75 | | | | | 80 |
| Phe | Glu | Ala | Gly | Lys | Gly | Ala | Ser | Arg | Leu | Lys | Ala | Cys | Thr | Cys | Ile |
| | | | | 85 | | | | | 90 | | | | | 95 | |
| Cys | Arg | Lys | Glu | Lys | Lys | Phe | Tyr | Asn | Val | Ala | Glu | Glu | Ile | Gln | Ser |
| | | | 100 | | | | | 105 | | | | | 110 | | |
| Leu | Lys | Gln | Arg | Ile | Met | Asp | Ile | Ser | Arg | Lys | Arg | Glu | Thr | Tyr | Gly |
| | | | 115 | | | | | 120 | | | | | 125 | | |
| Ile | Thr | Asn | Ile | Asn | Asn | Asn | Ala | Gly | Glu | Gly | Pro | Ser | Asn | Gln | Val |
| 130 | | | | | 135 | | | | | 140 | | | | | |
| Thr | Lys | Leu | Arg | Arg | Thr | Thr | Ser | Tyr | Val | Asp | Glu | Gln | Asp | Tyr | Ile |
| 145 | | | | | 150 | | | | | 155 | | | | | 160 |
| Phe | Val | Gly | Phe | Gln | Asp | Val | Val | Gln | Thr | Phe | Leu | Ala | Gln | Leu | Leu |
| | | | | 165 | | | | | 170 | | | | | 175 | |
| Lys | Ala | Glu | Pro | Arg | Arg | Ser | Val | Leu | Ser | Ile | Tyr | Gly | Met | Gly | Gly |
| | | | 180 | | | | | 185 | | | | | 190 | | |
| Leu | Gly | Lys | Thr | Thr | Leu | Ala | Arg | Lys | Leu | Tyr | Thr | Ser | Pro | Asp | Ile |
| | | 195 | | | | | 200 | | | | | 205 | | | |
| Leu | Asn | Ser | Phe | Arg | Thr | Arg | Ala | Trp | Ile | Cys | Val | Ser | Gln | Glu | Tyr |
| | 210 | | | | | 215 | | | | | 220 | | | | |
| Asn | Thr | Met | Asp | Leu | Leu | Arg | Asn | Ile | Ile | Lys | Ser | Ile | Gln | Gly | Arg |
| 225 | | | | | 230 | | | | | 235 | | | | | 240 |
| Thr | Lys | Glu | Thr | Leu | Asp | Leu | Leu | Glu | Arg | Met | Thr | Glu | Gly | Asp | Leu |
| | | | | 245 | | | | | 250 | | | | | 255 | |
| Glu | Ile | Tyr | Leu | Arg | Asp | Leu | Leu | Lys | Glu | Arg | Lys | Tyr | Leu | Val | Val |
| | | | 260 | | | | | 265 | | | | | 270 | | |
| Val | Asp | Asp | Val | Trp | Gln | Arg | Glu | Ala | Trp | Glu | Ser | Leu | Lys | Arg | Ser |
| | | 275 | | | | | 280 | | | | | 285 | | | |
| Phe | Pro | Asp | Gly | Lys | Asn | Gly | Ser | Arg | Val | Ile | Ile | Thr | Thr | Arg | Lys |
| | 290 | | | | | 295 | | | | | 300 | | | | |
| Glu | Asp | Val | Ala | Glu | Arg | Ala | Asp | Asp | Arg | Gly | Phe | Val | His | Lys | Leu |
| 305 | | | | | 310 | | | | | 315 | | | | | 320 |
| Arg | Phe | Leu | Ser | Gln | Glu | Ser | Trp | Asp | Leu | Phe | Arg | Arg | Lys | Leu |
| | | | | 325 | | | | | 330 | | | | | 335 | |
| Leu | Asp | Val | Arg | Ala | Met | Val | Pro | Glu | Met | Gly | Ser | Leu | Ala | Lys | Asp |
| | | | 340 | | | | | 345 | | | | | 350 | | |
| Met | Val | Glu | Lys | Cys | Arg | Gly | Leu | Pro | Leu | Ala | Ile | Val | Val | Leu | Ser |
| | | 355 | | | | | 360 | | | | | 365 | | | |
| Gly | Leu | Leu | Ser | His | Lys | Lys | Gly | Leu | Asn | Gln | Trp | Gln | Lys | Val | Lys |
| | 370 | | | | | 375 | | | | | 380 | | | | |

```
Asp His Leu Trp Lys Asn Ile Lys Glu Asp Lys Ser Ile Glu Ile Ser
385                 390                 395                 400

Asn Ile Leu Ser Leu Ser Tyr Asn Asp Leu Ser Thr Ala Leu Lys Gln
            405                 410                 415

Cys Phe Leu Tyr Phe Gly Ile Phe Pro Glu Asp Gln Val Val Lys Ala
            420                 425                 430

Asp Asp Ile Ile Arg Leu Trp Met Ala Glu Gly Phe Ile Pro Arg Gly
            435                 440                 445

Glu Glu Arg Met Glu Asp Val Ala Asp Gly Phe Leu Asn Glu Leu Ile
            450                 455                 460

Arg Arg Ser Leu Val Gln Val Ala Lys Thr Phe Trp Glu Lys Val Thr
465                 470                 475                 480

Asp Cys Arg Val His Asp Leu Leu Arg Asp Leu Ala Ile Gln Lys Ala
            485                 490                 495

Leu Glu Val Asn Phe Phe Asp Ile Tyr Asp Pro Arg Ser His Ser Ile
            500                 505                 510

Ser Ser Leu Cys Ile Arg His Gly Ile His Ser Gly Glu Arg Tyr
            515                 520                 525

Leu Ser Ser Leu Asp Leu Ser Asn Leu Lys Leu Arg Ser Ile Met Phe
            530                 535                 540

Phe Asp Pro Asp Phe Arg Lys Met Ser His Ile Asn Leu Arg Ser Glu
545                 550                 555                 560

Phe Gln His Leu Tyr Val Leu Tyr Leu Asp Thr Asn Phe Gly Tyr Val
            565                 570                 575

Ser Met Val Pro Asp Ala Ile Gly Ser Leu Tyr His Leu Lys Leu Leu
            580                 585                 590

Arg Leu Arg Gly Ile His Asp Ile Pro Ser Ser Ile Gly Asn Leu Lys
            595                 600                 605

Asn Leu Gln Thr Leu Val Val Val Asn Gly Tyr Thr Phe Phe Cys Glu
            610                 615                 620

Leu Pro Cys Lys Thr Ala Asp Leu Ile Asn Leu Arg His Leu Val Val
625                 630                 635                 640

Gln Tyr Thr Glu Pro Leu Lys Cys Ile Asn Lys Leu Thr Ser Leu Gln
            645                 650                 655

Val Leu Asp Gly Val Ala Cys Asp Gln Trp Lys Asp Val Asp Pro Val
            660                 665                 670

Asp Leu Val Asn Leu Arg Glu Leu Ser Met Asp Arg Ile Arg Ser Ser
            675                 680                 685

Tyr Ser Leu Asn Asn Ile Ser Ser Leu Lys Asn Leu Ser Thr Leu Lys
            690                 695                 700

Leu Ile Cys Gly Glu Arg Gln Ser Phe Ala Ser Leu Glu Phe Val Asn
705                 710                 715                 720

Cys Cys Glu Lys Leu Gln Lys Leu Trp Leu Gln Gly Arg Ile Glu Glu
            725                 730                 735

Leu Pro His Leu Phe Ser Asn Ser Ile Thr Met Met Val Leu Ser Phe
            740                 745                 750

Ser Glu Leu Thr Glu Asp Pro Met Pro Ile Leu Gly Arg Phe Pro Asn
            755                 760                 765

Leu Arg Asn Leu Lys Leu Asp Gly Ala Tyr Glu Gly Lys Glu Ile Met
770                 775                 780

Cys Ser Asp Asn Ser Phe Ser Gln Leu Glu Phe Leu His Leu Arg Asp
785                 790                 795                 800

Leu Trp Lys Leu Glu Arg Trp Asp Leu Gly Thr Ser Ala Met Pro Leu
            805                 810                 815
```

```
Ile Lys Gly Leu Gly Ile His Asn Cys Pro Asn Leu Lys Glu Ile Pro
                820                 825                 830

Glu Arg Met Lys Asp Val Glu Leu Leu Lys Arg Asn Tyr Met Leu
            835                 840                 845

<210> SEQ ID NO 42
<211> LENGTH: 846
<212> TYPE: PRT
<213> ORGANISM: solanum bulbocastanum

<400> SEQUENCE: 42

Met Ala Asp Ala Phe Leu Ser Phe Ala Val Gln Lys Leu Gly Asp Phe
1               5                   10                  15

Leu Ile Gln Lys Val Ser Leu Arg Lys Ser Leu Arg Asp Glu Ile Arg
                20                  25                  30

Trp Leu Ile Asn Glu Leu Leu Phe Ile Arg Ser Phe Leu Arg Asp Ala
            35                  40                  45

Glu Gln Lys Gln Cys Gly Asp Gln Arg Val Gln Trp Val Phe Glu
    50                  55                  60

Ile Asn Ser Ile Ala Asn Asp Ala Val Ala Ile Leu Glu Thr Tyr Ser
65                  70                  75                  80

Phe Glu Ala Gly Lys Gly Ala Ser Arg Leu Lys Ala Cys Thr Cys Ile
                85                  90                  95

Cys Arg Lys Glu Lys Lys Phe Tyr Asn Val Ala Glu Glu Ile Gln Ser
            100                 105                 110

Leu Lys Gln Arg Ile Met Asp Ile Ser Arg Lys Arg Gly Thr Tyr Gly
        115                 120                 125

Ile Thr Asn Ile Asn Asn Asn Ala Gly Glu Gly Pro Ser Asn Gln Val
    130                 135                 140

Thr Lys Leu Arg Arg Thr Thr Ser Tyr Val Asp Glu Gln Asp Tyr Ile
145                 150                 155                 160

Phe Val Gly Phe Gln Asp Val Ile Gln Thr Phe Leu Ala Gln Leu Leu
                165                 170                 175

Lys Ala Glu Pro Arg Arg Ser Val Leu Ser Ile Tyr Gly Met Gly Gly
            180                 185                 190

Leu Gly Lys Thr Thr Leu Ala Arg Lys Leu Tyr Thr Ser Pro Asp Ile
        195                 200                 205

Leu Asn Ser Phe Pro Thr Arg Ala Trp Ile Cys Val Ser Gln Glu Tyr
    210                 215                 220

Asn Thr Met Asp Leu Leu Arg Asn Ile Ile Lys Ser Val Gln Gly Arg
225                 230                 235                 240

Thr Lys Glu Thr Leu Asp Leu Leu Glu Arg Met Thr Glu Gly Asp Leu
                245                 250                 255

Glu Ile Tyr Leu Arg Asp Leu Leu Lys Glu Arg Lys Tyr Leu Val Val
            260                 265                 270

Val Asp Asp Val Trp Gln Arg Glu Ala Trp Glu Ser Leu Lys Arg Ser
        275                 280                 285

Phe Pro Asp Gly Lys Asn Gly Ser Arg Val Ile Ile Thr Thr Arg Lys
    290                 295                 300

Glu Asp Val Ala Glu Arg Ala Asp Arg Gly Phe His Lys Leu
305                 310                 315                 320

Arg Phe Leu Ser Gln Glu Glu Ser Trp Asp Leu Phe Arg Arg Lys Leu
                325                 330                 335

Leu Asp Val Arg Ala Met Val Pro Glu Met Glu Ser Leu Ala Lys Asp
            340                 345                 350
```

```
Met Val Glu Lys Cys Arg Gly Leu Pro Leu Ala Ile Val Val Leu Ser
        355                 360                 365

Gly Leu Leu Ser His Lys Lys Gly Leu Asn Gln Trp Gln Lys Val Lys
        370                 375                 380

Asp His Leu Trp Lys Asn Ile Lys Glu Asp Lys Ser Ile Glu Ile Ser
385                 390                 395                 400

Asn Ile Leu Ser Leu Ser Tyr Asn Asp Leu Ser Thr Ala Leu Lys Gln
                405                 410                 415

Cys Phe Leu Tyr Phe Gly Ile Phe Pro Glu Asp Gln Val Val Lys Ala
                420                 425                 430

Asp Asp Ile Ile Arg Leu Trp Met Ala Glu Gly Phe Ile Pro Arg Gly
                435                 440                 445

Glu Glu Arg Met Glu Asp Val Ala Glu Gly Phe Leu Asn Glu Leu Ile
        450                 455                 460

Arg Arg Ser Leu Val Gln Val Ala Lys Thr Phe Trp Glu Lys Val Thr
465                 470                 475                 480

Asp Cys Arg Val His Asp Leu Leu Arg Asp Leu Ala Ile Gln Lys Ala
                485                 490                 495

Leu Glu Val Asn Phe Phe Asp Ile Tyr Gly Pro Arg Ser His Ser Ile
                500                 505                 510

Ser Ser Leu Cys Ile Arg His Gly Ile His Ser Glu Gly Glu Arg Tyr
        515                 520                 525

Leu Ser Ser Leu Asp Leu Ser Asn Leu Lys Leu Arg Ser Ile Met Phe
        530                 535                 540

Phe Asp Pro Tyr Ile Cys Asn Val Phe Gln His Ile Asp Val Phe Arg
545                 550                 555                 560

His Leu Tyr Val Leu Tyr Leu Asp Thr Asn Phe Gly Tyr Val Ser Met
                565                 570                 575

Val Pro Asp Ala Ile Gly Ser Leu Tyr His Leu Lys Leu Leu Arg Leu
                580                 585                 590

Arg Gly Ile His Asp Ile Pro Ser Ser Ile Gly Asn Leu Lys Asn Leu
        595                 600                 605

Gln Thr Leu Val Val Val Asn Gly Tyr Thr Phe Phe Cys Gln Leu Pro
        610                 615                 620

Cys Lys Thr Ala Asp Leu Ile Asn Leu Arg His Leu Val Val Gln Tyr
625                 630                 635                 640

Thr Glu Pro Leu Lys Cys Ile Asn Lys Leu Thr Ser Leu Gln Val Leu
                645                 650                 655

Asp Gly Val Ala Cys Asp Gln Trp Lys Asp Val Asp Pro Val Asp Leu
                660                 665                 670

Val Asn Leu Arg Glu Leu Ser Met Asp Arg Ile Arg Ser Ser Tyr Ser
                675                 680                 685

Leu Asn Asn Ile Ser Ser Leu Lys Asn Leu Ser Thr Leu Lys Leu Ile
        690                 695                 700

Cys Gly Glu Arg Gln Ser Phe Ala Ser Leu Glu Phe Val Asn Cys Cys
705                 710                 715                 720

Glu Lys Leu Gln Lys Leu Trp Leu Gln Gly Arg Ile Glu Glu Leu Pro
                725                 730                 735

His Leu Phe Ser Asn Ser Ile Thr Met Met Val Leu Ser Leu Ser Val
                740                 745                 750

Leu Thr Glu Asp Pro Met Pro Ile Leu Gly Ile Leu Pro Asn Leu Arg
        755                 760                 765

Asn Leu Val Leu Phe Arg Ala Ser Tyr Glu Gly Lys Glu Ile Met Cys
770                 775                 780
```

-continued

```
Ser Asp Asn Ser Phe Ser Gln Leu Glu Phe Leu Ile Leu Arg Asp Leu
785                 790                 795                 800

Glu Lys Leu Glu Arg Trp Asp Leu Gly Thr Ser Ala Met Pro Leu Ile
                805                 810                 815

Lys Gly Leu Gly Ile His Asn Cys Pro Asn Leu Lys Glu Ile Pro Glu
                820             825                 830

Arg Met Lys Asp Val Glu Leu Leu Lys Arg Asn Tyr Met Leu
            835             840                 845
```